(12) United States Patent
Okano et al.

(10) Patent No.: US 8,835,446 B2
(45) Date of Patent: Sep. 16, 2014

(54) QUINAZOLINE DERIVATIVES AND PHARMACEUTICAL COMPOSITIONS THEREOF

(71) Applicant: Nippon Shinyaku Co., Ltd., Kyoto (JP)

(72) Inventors: Masahiko Okano, Kyoto (JP); Tatsuya Oyama, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 13/855,096

(22) Filed: Apr. 2, 2013

(65) Prior Publication Data

US 2013/0225613 A1  Aug. 29, 2013

Related U.S. Application Data

(63) Continuation of application No. 12/089,087, filed as application No. PCT/JP2006/319803 on Oct. 3, 2006, now Pat. No. 8,431,586.

(30) Foreign Application Priority Data

Oct. 3, 2005 (JP) ................................. 2005-290416

(51) Int. Cl.
*C07D 239/94* (2006.01)
(52) U.S. Cl.
USPC ....................................... 514/266.4; 544/293
(58) Field of Classification Search
CPC .................................................... C07D 239/94
USPC ......................................................... 544/293
See application file for complete search history.

(56) References Cited

U.S. PATENT DOCUMENTS

| 6,794,389 | B2 | 9/2004 | Okana et al. |
| 2003/0119855 | A1 | 6/2003 | Okano et al. |
| 2004/0116450 | A1 | 6/2004 | Oyama |
| 2005/0009902 | A1 | 1/2005 | Miyaji et al. |
| 2005/0009917 | A1 | 1/2005 | Sato et al. |
| 2005/0176741 | A1 | 8/2005 | Okano et al. |
| 2005/0192357 | A1 | 9/2005 | Arai et al. |
| 2006/0258703 | A1 | 11/2006 | Shii et al. |

FOREIGN PATENT DOCUMENTS

| JP | 2002-138052 A | 5/2002 |
| JP | 2003-201250 A | 7/2003 |
| JP | 2004-107209 A | 4/2004 |
| JP | 2005-047909 A | 2/2005 |
| JP | 2005-139194 A | 6/2005 |
| WO | 01/72710 A1 | 10/2001 |
| WO | 02/074341 A1 | 9/2002 |
| WO | 03/091224 A1 | 11/2003 |

OTHER PUBLICATIONS

M. F. Semmelhack, et al., Total Synthesis of the Cephalotaxus Alkaloids. A Problem in Nucleophilic Aromatic Substitution, Journal of the American Chemical Society, vol. 97, Apr. 30, 1975, pp. 2507-2516.
S. M. McElvain, et al., The Preparation of Orthoesters, Journal of the American Chemical Society, vol. 64, Aug. 1942, pp. 1825-1827.
King, isoOxazolidine and Tetrahydro-1: 2-isooxazine., J. Chem. Soc., 1942, pp. 432-433.
J. Ishwara Bhat, et al., N-Nitroso-N,O-dialkylhydroxylamines: preparation, structure, and mechanism of the hydronium ion catalysed solvolytic nitrous oxide extrusion reaction, J. Chem Soc., Perkin Trans, 2, 2000, pp. 1435-1446.
Dae-Kee Kim, et al., Synthesis and Anti-HIV-1 Activity of a Series of 1-Alkoxy-5-alkyl-6-(arylthio)uracils, J. Med. Chem., 1997, 40, pp. 2363-2373.

*Primary Examiner* — Brian McDowell
(74) *Attorney, Agent, or Firm* — McDermott Will & Emery LLP

(57) ABSTRACT

The present invention relates to novel quinazoline derivatives with less skin irritation and an excellent action of strongly suppressing scratching behavior, and pharmaceutical compositions containing a quinazoline derivative as an active ingredient. The present invention is directed to the quinazoline derivatives represented by the general formula [1] or pharmaceutically acceptable salts thereof. In the general formula [1], $R^1$ represents hydrogen or the like; $R^2$ represents hydrogen or the like; $R^3$ and $R^4$ are the same or different and represent hydrogen, alkyl, alkoxy or halogen; $R^5$ is combined with $R^6$ to represent alkylene or represents hydrogen, hydroxy, alkyl, phenyl or alkoxy; $R^6$ represents alkyl, cycloalkyl, phenyl, a 5- to 10-membered aromatic heterocyclic group containing one to three heteroatoms selected from the group consisting of a nitrogen atom, an oxygen atom and a sulfur atom, or $—N(R^{6-1})(R^{6-2})$.

6 Claims, No Drawings

QUINAZOLINE DERIVATIVES AND PHARMACEUTICAL COMPOSITIONS THEREOF

CROSS-REFERENCE TO PRIOR APPLICATIONS

This application is a continuation of U.S. patent application Ser. No. 12/089,087 filed Sep. 25, 2009, which is a U.S. national phase application under 35 U.S.C. §371 of International Patent Application No, PCT/JP2006/319803 filed Oct. 3, 2006, which claims the benefit of priority to Japanese Patent Application No. 2005-290416 filed Oct. 3, 2005, the disclosures of all of which are hereby incorporated by reference in their entireties. The International Application was published in Japanese on Apr. 12, 2007 as WO 2007/040231 A1.

FIELD OF THE INVENTION

The present invention relates to quinazoline derivatives, which are useful as a pharmaceutical agents, particularly antipruritic agents, and pharmaceutically acceptable salts thereof, and a pharmaceutical composition thereof.

BACKGROUND OF THE INVENTION

Itching is a sensation, i.e., pruritic sensation, which takes place at the superficial layer of the skin and the mucosa. The pruritic sensation is a sensation, which senses a parasite or an irritant on the superficial layer of the skin and is for removing an invading substance or an irritant by scratching or related behavior. Itching can be easily understood as a sensation to cause an impulse to scratch, but its mechanism has not been elucidated completely yet.

Diseases accompanied by itching are roughly classified into pruritic dermatosis accompanied by skin lesion (for example, atopic dermatitis, urticaria, psoriasis, xeroderma and tinea) and pruritus cutaneous, which is not accompanied by skin lesions, but causes itching due to kidney dialysis and visceral diseases [for example, diabetes, blood diseases, cholestatic liver injury (primary biliary liver cirrhosis) and kidney diseases], hyperthyroidism, multiple sclerosis or the like. In addition, as a disease accompanied by severe itching, diseases of cornea and conjunctiva such as allergic conjunctivitis can be exemplified. Recently, such diseases have rapidly increased to constitute a large problem in view of QOL (quality of life). Most itching diseases are common in the fact that they cause a vicious cycle of scratching the skin. Histamine is known as a typical itch-causing substance and induces itching in the case where it is externally added and is internally released from mastocytes.

An antihistaminic agent, an antiallergic agent, a steroid external preparation and the like are used for the treatment of pruritic dermatosis. However, there is no drug that is satisfactory for the treatment of itching due to pruritic dermatosis. Further, it has recently been reported that factors other than histamine take part in itching due to atopic dermatitis. In fact, also in many clinical cases, an antihistaminic agent or an antiallergic agent does not exert a remarkable effect on itching due to atopic dermatitis. In the treatment of pruritus cutaneous, antihistaminic agents or steroid external preparations are prescribed in some cases. However, almost no effect is seen, and thus an effective therapy does not exist at present. As described above, there is no satisfactory drug for diseases accompanied by itching and a medicament which effectively suppresses itching regardless of causative diseases has been eagerly desired from a clinical point of view.

In order to solve this problem, several antipruritic agents have been identified, including quinazoline derivatives (WO 03/091224), neuronal nitric oxide synthase inhibitors (JP-A-2002-138052), cannabinoid receptor agonists (JP-A-2003-201250), glutamate receptor inhibitors (JP-A-2004-107209), piperidine derivatives (JP-A-2005-047909), prostaglandin derivatives (JP-A-2005-139194) and the like have been reported. Among these, quinazoline derivatives disclosed in WO 03/091224 strongly suppress scratching behavior spontaneously occurring in a mouse model with disruption of the horny layer barrier and is useful as a drug for effectively suppressing itching regardless of causative disease.

The skin of pruritic diseases, especially of atopic dermatitis or the like accompanied by skin lesion develops disruption of the horny layer barrier or hypersensitivity of the sensory nerves in comparison with the normal skin, and the skin is recognized to be sensitive to stimulation. When an external preparation is applied to such pruritic diseases, the external preparation is required to have an extremely low skin irritation. However, when the quinazoline derivative described in WO 03/091224 which has a guanidino group in the side chain at the 4-position of the quinazoline skeleton is used as an external preparation for a patient with atopic dermatitis, there is a possibility of causing skin irritation.

DESCRIPTION OF THE INVENTION

An object of the present invention is chiefly to provide a novel quinazoline derivative with less skin irritation and an excellent action of strongly suppressing scratching behavior and to provide an antipruritic agent comprising the quinazoline derivative as an active ingredient.

The present inventors made intensive studies and as a result, they found that the following quinazoline derivative, which is a novel compound, and a pharmaceutically acceptable salt thereof can achieve the above object, and thus, the present invention has been completed.

The present invention is directed to quinazoline derivatives represented by the following general formula [1] or a pharmaceutically acceptable salt thereof (hereinafter referred to as the "inventive compound").

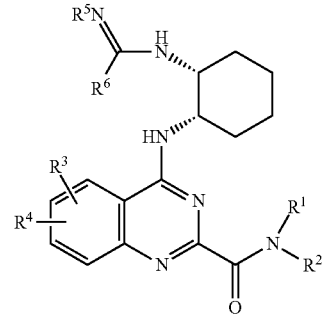

[1]

$R^1$ represents hydrogen or alkyl.

$R^2$ represents hydrogen, alkoxy, tetrahydropyranyl, phenyl, cycloalkyl, (cycloalkyl)alkyl or alkyl. The alkoxy, tetrahydropyranyl, phenyl, cycloalkyl, (cycloalkyl)alkyl and alkyl may be substituted with one to three groups selected from the group consisting of alkoxy, halogen, alkoxyalkyl, hydroxy, alkylthio, a 5- to 10-membered aromatic heterocyclic group containing one to three heteroatoms selected from the group consisting of a nitrogen atom, an oxygen atom and a sulfur atom, a 5- to 7-membered saturated aliphatic heterocyclic group which may be substituted with acyl and contains one to three nitrogen atoms, and phenyl which may be substituted with halogen or alkoxy.

$R^3$ and $R^4$ are the same or different and each represents hydrogen, alkyl, alkoxy or halogen.

$R^5$ is combined with $R^6$ to represent alkylene, or represents hydrogen, hydroxy, alkyl, phenyl or alkoxy. The alkylene may be substituted with hydroxy or oxo, and may be condensed with a benzene ring. The alkyl, phenyl and alkoxy represented by $R^5$ may be substituted with one to three groups selected from the group consisting of alkoxy, alkylthio and halogen.

$R^6$ represents alkyl, cycloalkyl, phenyl, a 5- to 10-membered aromatic heterocyclic group containing one to three heteroatoms selected from the group consisting of a nitrogen atom, an oxygen atom and a sulfur atom or —$N(R^{6-1})(R^{6-2})$. The alkyl, cycloalkyl, phenyl and aromatic heterocyclic group may be substituted with one to three groups selected from the group consisting of alkoxy, hydroxy, phenyl, pyridyl, furyl, halogen and N,N-dialkylamino. $R^{6-1}$ is combined with $R^{6-2}$ to represent —O—$(CH_2)_n$—, or represents hydrogen or alkyl. $R^{6-2}$ represents hydrogen or alkoxy which may be substituted with one to three groups selected from the group consisting of alkoxy, alkylthio and halogen.

Here, n represents an integer of 3 to 5.

Compounds wherein $R^5$ is hydrogen and $R^6$ is —$NH_2$ are excluded from Formula [1].

A preferred compound in the present invention, may include the following (1) to (29) quinazoline derivatives and pharmaceutically acceptable salts thereof. (1) 4-{[(1S,2R)-2-(ethanimidoylamino)cyclohexyl]amino}-N-(2-methoxyethyl)-6-methylquinazolin-2-carboxamide (2) N-(2,2-dimethylpropyl)-4-({(1S,2R)-2-[(2-methoxy-2-methylpropanimidoyl)amino]cyclohexyl}amino)-6-methylquinazolin-2-carboxamide (3) 4-({(1S,2R)-2-[(3-methoxypropanimidoyl)amino]cyclohexyl}amino)-N-(3-methoxypropyl)-6-methylquinazolin-2-carboxamide (4) 4-({(1S,2R)-2-[(3-hydroxypropanimidoyl)amino]cyclohexyl}amino)-N-isopropyl-6-methylquinazolin-2-carboxamide (5) 4-({(1S,2R)-2-[(3-hydroxypropanimidoyl)amino]cyclohexyl}amino)-N-(3-methoxypropyl)-6-methylquinazolin-2-carboxamide (6) 4-({(1S,2R)-2-[(2-hydroxy-2-methylpropanimidoyl)amino]cyclohexyl}amino)-N-isobutyl-6-methylquinazolin-2-carboxamide (7) N-(2-ethoxyethyl)-4-({(1S,2R)-2-[(3-hydroxy propanimidoyl)amino]cyclohexyl}amino)-6-methylquinazolin-2-carboxamide (8) 4-({(1S,2R)-2-[(2-hydroxy-2-methylpropanimidoyl)amino]cyclohexyl}amino)-N-isopropyl-6-methylquinazolin-2-carboxamide (9) 4-({(1S,2R)-2-[(2-hydroxy-2-methylpropanimidoyl)amino]cyclohexyl}amino)-N-(2-methoxyethyl)-6-methylquinazolin-2-carboxamide

(10) 4-({(1S,2R)-2-[(2-methoxyethanimidoyl)amino]cyclohexyl}amino)-N-(2-methoxyethyl)-6-methylquinazolin-2-carboxamide

(11) 4-{[(1S,2R)-2-(ethanimidoylamino)cyclohexyl]amino}-N-(3-methoxypropyl)-6-methylquinazolin-2-carboxamide

(12) 4-({(1S,2R)-2-[(2-methoxyethanimidoyl)amino]cyclohexyl}amino)-N-(3-methoxypropyl)-6-methylquinazolin-2-carboxamide

(13) 4-{[(1S,2R)-2-(ethanimidoylamino)cyclohexyl]amino}-N-(2-ethoxyethyl)-6-methylquinazolin-2-carboxamide

(14) N-(2-ethoxyethyl)-4-({(1S,2R)-2-[(2-methoxy ethanimidoyl)amino]cyclohexyl}amino)-6-methylquinazolin-2-carboxamide

(15) 4-{[(1S,2R)-2-(ethanimidoylamino)cyclohexyl]amino}-N-isopropyl-6-methylquinazolin-2-carboxamide

(16) 4-[((1S,2R)-2-{[amino(methoxyimino)methyl]amino}cyclohexyl)amino]-N-(2-methoxyethyl)-6-methylquinazolin-2-carboxamide

(17) 4-[((1S,2R)-2-{[amino(methoxyimino)methyl]amino}cyclohexyl)amino]-N-isobutyl-6-methylquinazolin-2-carboxamide

(18) 4-[((1S,2R)-2-{[amino(hydroxyimino)methyl]amino}cyclohexyl)amino]-N-isobutyl-6-methylquinazolin-2-carboxamide

(19) 4-[((1S,2R)-2-{[amino(methoxyimino)methyl]amino}cyclohexyl)amino]-N-(cyclopropylmethyl)-6-methylquinazolin-2-carboxamide

(20) 4-[((1S,2R)-2-{[amino(methoxyimino)methyl]amino}cyclohexyl)amino]-N-isopropyl-6-methylquinazolin-2-carboxamide

(21) 4-{[(1S,2R)-2-({imino[methoxy(methyl)amino]methyl}amino)cyclohexyl]amino}-N-isobutyl-6-methylquinazolin-2-carboxamide

(22) 4-[((1S,2R)-2-{[amino(methoxyimino)methyl]amino}cyclohexyl)amino]-N-(3-methoxypropyl)-6-methylquinazolin-2-carboxamide

(23) 4-[((1S,2R)-2-{[amino(hydroxyimino)methyl]amino}cyclohexyl)amino]-N-(3-methoxypropyl)-6-methylquinazolin-2-carboxamide

(24) 4-[((1S,2R)-2-{[amino(methoxyimino)methyl]amino}cyclohexyl)amino]-N-(2-ethoxyethyl)-6-methylquinazolin-2-carboxamide

(25) 4-[((1S,2R)-2-{[amino(ethoxyimino)methyl]amino}cyclohexyl)amino]-N-(2-methoxyethyl)-6-methylquinazolin-2-carboxamide

(26) 4-{[(1S,2R)-2-({amino[(2-methoxyethoxy)imino]methyl}amino)cyclohexyl]amino}-N-(2-methoxyethyl)-6-methylquinazolin-2-carboxamide

(27) 4-{[(1S,2R)-2-({amino[(2-fluoroethoxy)imino]methyl}amino)cyclohexyl]amino}-N-(2-methoxyethyl)-6-methyl quinazolin-2-carboxamide

(28) 4-({(1S,2R)-2-[(amino{[2-(methylthio)ethoxy]imino}methyl)amino]cyclohexyl}amino)-N-(2-methoxyethyl)-6-methylquinazolin-2-carboxamide

(29) 4-[((1S,2R)-2-{[amino(methoxyimino)methyl]amino}cyclohexyl)amino]-N-(2-methoxyethyl)-6-methylquinazolin-2-carboxamide Further, the present invention is also directed to a pharmaceutical composition comprising the inventive compound as an active ingredient, for example, a pharmaceutical composition for suppressing itching, which comprises the inventive compound as an active ingredient.

Hereinafter, the present invention will be described in detail.

Examples of the "alkyl" may include a linear or branched alkyl having 1 to 10 carbon atoms, and specific examples thereof may include methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl, n-nonyl, and n-decyl. Preferred is alkyl having 1 to 8 carbon atoms and more preferred is alkyl having 1 to 6 carbon atoms.

Examples of the alkyl moiety of the "alkoxy", "(cycloalkyl)alkyl", "alkoxyalkyl", "alkylthio" and "N,N-dialkylamino" may include the same alkyl as those described above.

Examples of the "tetrahydropyranyl" may include 2-tetrahydropyranyl, 3-tetrahydropyranyl and 4-tetrahydropyranyl.

Examples of the "cycloalkyl" may include cyclic alkyl having 3 to 10 carbon atoms which is monocyclic to tricyclic, and specific examples thereof may include cyclopropyl, cyclobutyl, cyclopentyl, cyclohexyl, cycloheptyl, cyclooctyl, cyclononyl, cyclodecanyl, adamanthyl (1-adamanthyl, 2-adamanthyl, and the like), 2-bicyclo[3.1.1]heptyl and 2-bicyclo[2.2.1]heptyl. Preferred is the cyclic alkyl having 4 to 9 carbon atoms, and more preferred is the cyclic alkyl having 5 to 8 carbon atoms.

Examples of the cycloalkyl moiety of the "(cycloalkyl)alkyl" may include the same cycloalkyl as those described above.

Examples of the "halogen" may include fluorine, chlorine, bromine and iodine.

Examples of the "aromatic heterocyclic group" may include a 5- to 10-membered aromatic heterocyclic group containing one to three heteroatoms selected from the group consisting of a nitrogen atom, an oxygen atom and a sulfur atom, and specific examples thereof may include pyridyl (2-pyridyl, 3-pyridyl, 4-pyridyl), pyrimidinyl (2-pyrimidinyl, 4-pyrimidinyl, 5-pyrimidinyl), pyrazinyl (2-pyrazinyl, and the like), pyridazinyl (3-pyridazinyl, 4-pyridazinolyl), pyrrolyl (2-pyrrolyl, and the like), furyl (2-furyl, 3-furyl), thienyl (2-thienyl, 3-thienyl), imidazolyl (1-imidazolyl, 4-imidazolyl, and the like), pyrazolyl (3-pyrazolyl, 5-pyrazolyl, and the like), oxazolyl (4-oxazolyl, 5-oxazolyl, and the like), thiazolyl (1,3-thiazol-2-yl, 1,3-thiazol-5-yl, and the like), isoxazolyl(isoxazol-4-yl, isoxazol-5-yl, and the like), and 1,3,4-thiadiazol-2-yl.

Examples of the "acyl" may include acyl having 1 to 11 carbon atoms, and specific examples thereof may include formyl, acetyl, propyonyl, butyryl, isobutyryl, benzoyl, 1-naphthoyl and 2-naphthoyl.

Examples of the "saturated aliphatic heterocyclic group" may include a 5- to 7-membered saturated aliphatic heterocyclic group containing one to three nitrogen atoms, and specific examples thereof may include pyrrolidinyl (1-pyrrolidinyl, 2-pyrrolidinyl, 3-pyrrolidinyl), piperidinyl (1-piperidinyl, 2-piperidinyl, 3-piperidinyl, 4-piperidinyl), piperazinyl (1-piperazinyl, 2-piperazinyl), homopiperazinyl (1-homopiperazinyl, 2-homopiperazinyl, 3-homopiperazinyl, 6-homopiperazinyl), morpholinyl (2-morpholinyl, 3-morpholinyl, 4-morpholinyl), and thiomorpholinyl (2-thiomorpholinyl, 3-thiomorpholinyl, 4-thiomorpholinyl).

Examples of the "pyridyl" may include 2-pyridyl, 3-pyridyl and 4-pyridyl.

Examples of the "furyl" may include 2-furyl and 3-furyl.

Examples of the "alkylene" may include linear or branched alkylene having 1 to 6 carbon atoms, and specific examples thereof may include methylene, ethylene, trimethylene, tetramethylene, pentamethylene and hexamethylene. Among these, preferred is alkylene having 2 to 5 carbon atoms, and more preferred is alkylene having 3 to 5 carbon atoms.

Examples of the "itching" may include itching accompanying atopic dermatitis, urticaria, psoriasis, xeroderma, tinea, vitiligo, local pruritus cutaneous caused by insect excretion or secretion, nodular prurigo, kidney dialysis, diabetes, blood diseases, cholestatic liver injury (primary biliary liver cirrhosis), liver diseases, kidney diseases, endocrine and metabolic disorders, visceral malignancy, hyperthyroidism, autoimmune diseases, multiple sclerosis, neurological diseases, psychoneurosis, allergic conjunctivitis, spring catarrh, atopic keratoconjunctivitis, or excess use of articles of taste and drugs.

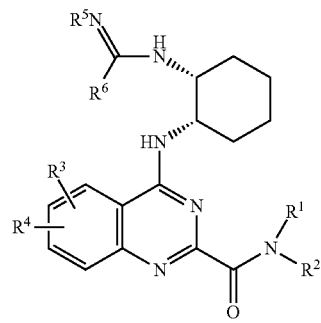

The inventive compound [1] can be produced according to, for example, the following method from a known compound or an intermediate which can be easily synthesized. In the production of the inventive compound [1], in the case where a raw material has a substituent which has an influence on a reaction, it is general that the reaction is carried out after the raw material is protected with a suitable protecting group by a known method in advance. It may be easily understood that the protecting group is detached by a known method after the reaction.

Production Method 1

The inventive compound [1] can be produced according to, for example, the following reaction step.

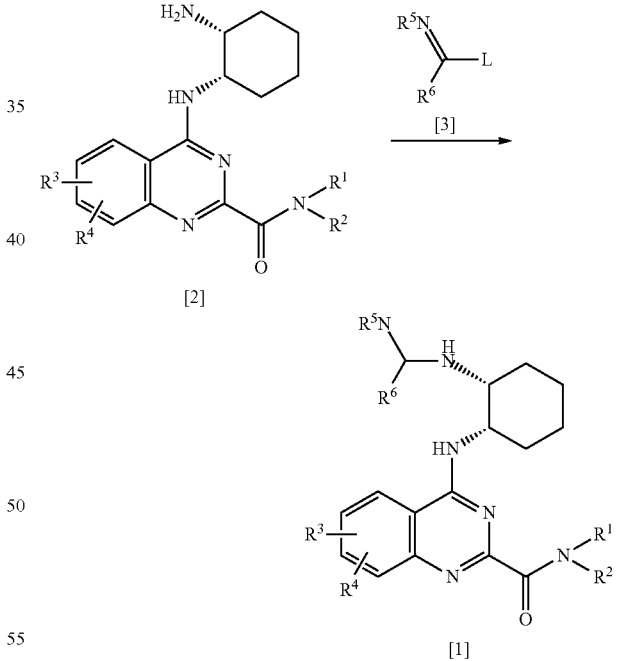

In the formulae, $R^1$ to $R^6$ have the same meanings as defined above. L represents a leaving group (for example, alkoxy, halogen, pyrazole-1-yl or methylthio).

The inventive compound [1] can be obtained by reacting a compound [2] with one equivalent to an excess amount of a compound [3] in a solvent, for example, an alcohol-based solvent such as methanol or ethanol, a hydrocarbon-based solvent such as benzene or toluene, an ether-based solvent such as dioxane or tetrahydrofuran, a halogen-based solvent such as chloroform or 1,2-dichloroethane, dimethylformamide, or the like in the presence or absence of a base such as triethylamine or N,N-diisopropylethylamine at a temperature of 0° C. to the boiling point of the solvent employed for several hours to several days. It is preferred that the reaction is carried out in the presence of triethylamine by using ethoxy as the leaving group L of the compound [3] and ethanol as the solvent at 80° C. for 1 to 48 hours.

The compound [2], which is a raw compound, can be produced by a known method (see, for example, WO 03/091224).

The compound [3], which is a raw compound, is commercially available, but can also be produced by a known method (see, for example, J. Am. Chem. Soc., 1975, 97, 2512 and J. Am. Chem. Soc., 1942, 64, 1827)).

Production Method 2

The inventive compound [1a] wherein $R^5$ is alkoxy, $R^6$ is —N($R^{61}$)($R^{62}$), and $R^{61}$ and $R^{62}$ are both hydrogen, can also be produced according to the following reaction step:

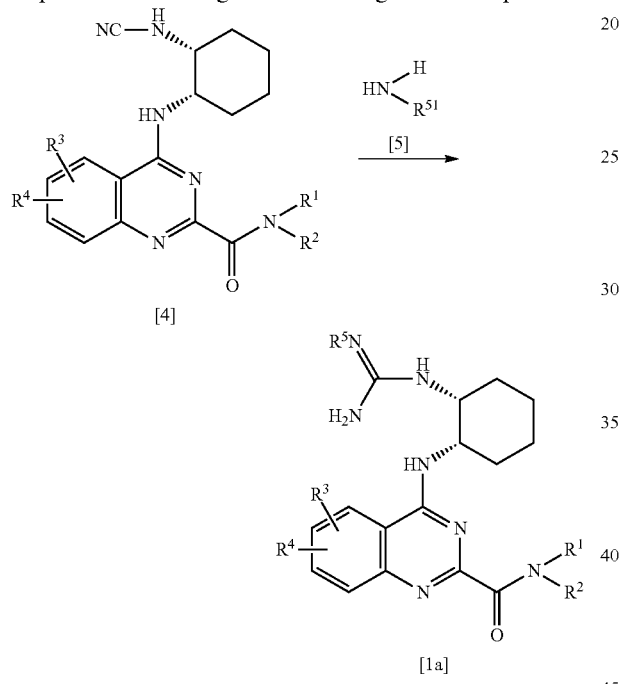

In the formulae, $R^1$ to $R^4$ have the same meanings as defined above. $R^{5-1}$ represents alkoxy which may be substituted with one to three groups selected from the group consisting of alkoxy, alkylthio and halogen.

Production Method 3

The inventive compound [1b] wherein $R^5$ is hydrogen and $R^6$ is —N($R^{6-1}$)($R^{6-2}$), can also be produced according to the following reaction step:

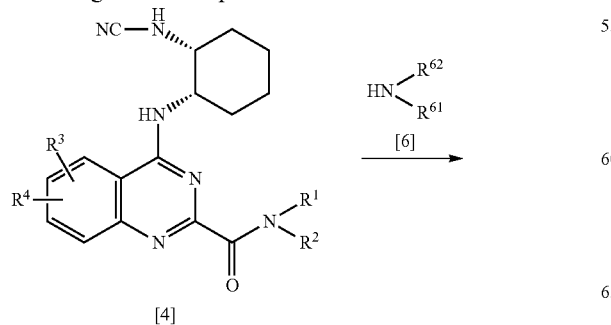

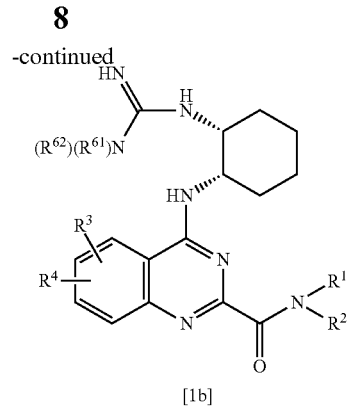

In the formulae, $R^1$ to $R^4$, $R^{6-1}$ and $R^{6-2}$ have the same meanings as defined above.

The inventive compound [1a] or [1b] can be obtained by reacting a compound [4] with one equivalent to an excess amount of a compound [5] or [6] in a solvent, for example, an alcohol-based solvent such as methanol or ethanol, a hydrocarbon-based solvent such as benzene or toluene, an ether-based solvent such as dioxane or tetrahydrofuran, a halogen-based solvent such as chloroform or 1,2-dichloroethane, dimethylformamide, or the like in the presence or absence of an inorganic base such as sodium carbonate or potassium carbonate, or an organic base such as triethylamine or N,N-diisopropylethylamine at a temperature of 0° C. to the boiling point of the solvent employed for several hours to several days. It is preferred that the reaction is carried out in the presence of sodium carbonate by using ethanol or dioxane as the solvent at 50° C. to 80° C. for 1 hour to 24 hours.

The compound [4], which is a raw compound, can be produced according to the following reaction step:

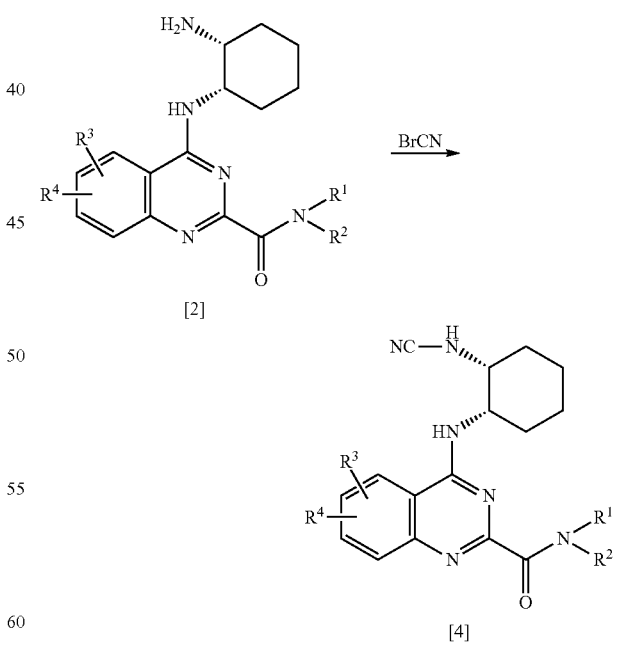

In the formulae, $R^1$ to $R^4$ have the same meanings as defined above.

The compound [4] can be obtained by reacting the compound [2] with one equivalent to an excess amount of BrCN in a solvent, for example, a hydrocarbon-based solvent such as benzene or toluene, an ether-based solvent such as dioxane or tetrahydrofuran, a halogen-based solvent such as chloroform or 1,2-dichloroethane, dimethylformamide, or the like in the presence of an inorganic base such as sodium carbonate or potassium carbonate, or an organic base such as triethylamine or N,N-diisopropylethylamine at a temperature of −78° C. to the boiling point of the solvent employed for several minutes to several days. It is preferred that the reaction is carried out in the presence of triethylamine by using tetrahydrofuran as the solvent at −50° C. to 0° C. for 10 minutes to 1 hour.

Further, the compound [4], which is a raw compound, can also be produced according to the following reaction step:

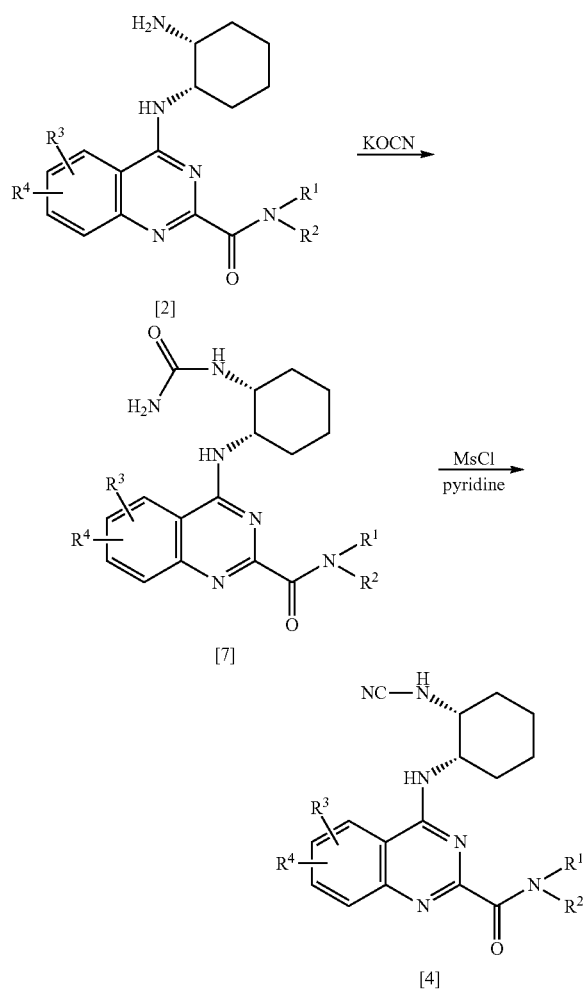

A compound [7] can be obtained by reacting the compound [2] with one equivalent to an excess amount of potassium cyanate in a solvent, for example, water, an alcohol-based solvent such as methanol or ethanol, or the like in the presence or absence of an acid such as hydrochloric acid or sulfuric acid, or a base such as triethylamine, N,N-diisopropylethylamine, sodium hydroxide or potassium hydroxide at a temperature of 0° C. to the boiling point of the solvent employed for several hours to several days. It is preferred that the reaction is carried out in the presence of triethylamine by using hydrous ethanol as the solvent at 50° C. to 100° C. for 1 hour to 5 hours. The compound [4] can be obtained by reacting the compound [7] with methane sulfonyl chloride (MsCl) in pyridine at −10° C. to 50° C. for 30 minutes to 5 hours.

The compounds [5] and [6], which are raw compounds, are commercially available, but can also be produced by a known method (see, for example, J. Org. Chem., 1942, 432, J. Chem. Soc. Perkin Trans 2, 2000, 1435 and J. Med. Chem., 1997, 40, 2363).

The quinazoline derivatives according to the present invention can be used as a pharmaceutical in the form of a free base itself, or can be used by formulating it in the form of a pharmaceutically acceptable salt by a known method. Examples of such salts include those with a mineral acid such as hydrochloric acid, hydrobromic acid, sulfuric acid or phosphoric acid, these with an organic acid such as acetic acid, citric acid, tartaric acid, maleic acid, succinic acid, fumaric acid, p-toluenesulfonic acid, benzenesulfonic acid or methanesulfonic acid, and the like.

For example, a hydrochloride salt of the quinazoline derivative according to the present invention can be obtained by dissolving a quinazoline derivative according to the present invention in a suitable solvent and adding an alcohol solution, an ethyl acetate solution or an ether solution of hydrogen chloride thereto, followed by concentration to dryness.

Among the inventive compounds [1], some compounds may have an asymmetric carbon, and all of the optical isomers and mixtures thereof are also included in the present invention. Such an optical isomer can be produced by, for example, starting from a racemate obtained as described above, utilizing the basicity thereof and using an optically active acid (tartaric acid, dibenzoyltartaric acid, mandelic acid, 10-camphorsulfonic acid or the like) through a known method for optical resolution, or by using a previously prepared optically active compound as a starting material. In addition to this, it can also be produced by optical resolution or asymmetric synthesis using a chiral column.

Further, in the inventive compounds [1], there are also those compounds which may exist in the cis form, trans form, Z form or E form, and each isomer and mixtures thereof are also included in the present invention.

When the inventive compound is administered as a pharmaceutical, the inventive compound is administered to mammals including humans as it is or in a pharmaceutically acceptable non-toxic inert carrier, for example, as a pharmaceutical composition comprising the inventive compound in an amount of 0.001% to 99.5%, preferably 0.1% to 90%.

As the carrier, one or more types of auxiliary agents for a formulation such as solid, semi-solid or liquid diluents, fillers and other auxiliary agents for a drug formulation may be used. It is preferred that a pharmaceutical composition according to the present invention is administered in a unit dosage form. The administration of the pharmaceutical composition can be carried out by intra-tissue administration, oral administration, intravenous administration, local administration (transdermal administration, instillation, or the like) or transrectal administration. It may be easily understood that a dosage form suitable for any of these administration routes is employed. For example, oral administration or local administration (transdermal administration or instillation) is preferred.

While it is preferred that the dose as an antipruritic agent is adjusted depending on the conditions of the patient such as the age, body weight, nature and degree of the disease as well as the administration route, a daily dose as an active ingredient of the inventive compound in an adult is usually in the range from 0.1 mg to 5 g per adult, preferably from 1 mg to 500 mg per adult in the case of oral administration. In the case of transdermal administration, it is in the range from 0.001% to 5%, preferably from 0.01% to 0.1%. In the case of instillation, it is in the range from 0.0001% to 0.5%, preferably from 0.001% to 0.01%. In some cases, a lower dose may be sufficient or a higher dose may be required. Usually, the dose is given once daily or several times daily as divided portions, or it can be given intravenously and continuously over a period of 1 to 24 hours a day.

Oral administration can be accomplished in a solid or liquid dosage unit such as a bulk powder, a powder, a tablet, a sugar-coated preparation, a capsule, a granule, a suspension, a liquid, a syrup, a drop, a sublingual tablet, a suppository or other dosage forms. A bulk powder is produced by pulverizing an active ingredient into a suitable size. A powder is produced by pulverizing an active ingredient into a suitable size followed by mixing with a pharmaceutical carrier such as an edible carbohydrate including starch or mannitol, which has been pulverized in a similar manner into a suitable size. If necessary, a flavor, a preservative, a dispersing agent, a colorant, a fragrance or other additive may be mixed therein.

A capsule is produced by filling a bulk powder or a powder which has previously been pulverized into a powder form as described above or a granule obtained as described in the section of a tablet, for example, in a capsule shell such as a gelatin capsule. It is also possible to perform such a filling operation after mixing a lubricant, a fluidizing agent such as colloidal silica, talc, magnesium stearate, calcium stearate or solid polyethylene glycol with the material in a powder form. If a disintegrant or a solubilizing agent such as carboxymethyl cellulose, carboxymethyl cellulose calcium, low substituted hydroxypropyl cellulose, croscarmellose sodium, carboxy starch sodium, calcium carbonate or sodium carbonate is added, the effectiveness of the pharmaceutical taken as a capsule can be enhanced.

The finely pulverized powder of the inventive compound can be suspended and dispersed in a vegetable oil, polyethylene glycol, glycerin or a surfactant, and then encapsulated in a gelatin sheet, thereby being prepared as a soft capsule. A tablet is produced by formulating a powder mixture, converting it into a granule or a slug, adding a disintegrant or a lubricant thereto and then compressing it into a tablet. The powder mixture is obtained by mixing an appropriately pulverized material with a diluent or a base described above, and if necessary, a binder (for example, sodium carboxymethyl cellulose, hydroxypropyl cellulose, methyl cellulose, hydroxypropylmethyl cellulose, gelatin, polyvinyl pyrrolidone, polyvinyl alcohol or the like), a dissolution retardant (for example, paraffin, wax, hydrogenated castor oil or the like), a resorption promoter (for example, a quaternary salt), or an adsorbent (for example, bentonite, kaolin, calcium diphosphate or the like) may also be mixed together. The powder mixture can be granulated by wetting it with a binder such as syrup, starch glue, gum arabic, a cellulose solution or a polymeric material solution and then passing it forcibly through a sieve. Instead of granulating the powder as described above, the powder can be subjected first to a tabletting machine to obtain an incompletely shaped slug which is then pulverized to obtain a granule. The components of the granule thus obtained can be prevented from adhering to one another by adding a lubricant such as stearic acid, a stearate, talc or mineral oil, or the like. The mixture thus lubricated is then compressed into a tablet. The tablet thus obtained can be film-coated or sugar-coated.

Further, the inventive compound may also be compressed directly into a tablet after mixing it with a fluidized inert carrier without being subjected to the granulating or slugging process as described above. A transparent or semi-transparent protective film made of a shellac sealing film, a film made of a sugar or a polymeric material and a glossy film made of a wax may also be employed.

Other oral dosage forms such as solutions, syrups and elixirs can also be formulated into a unit dosage form such that a certain amount of the preparation contains a certain amount of the inventive compound. A syrup is produced by dissolving the inventive compound in a suitable flavored aqueous solution, while an elixir is produced by using a non-toxic alcoholic carrier. A suspension is formulated by dispersing the inventive compound in a non-toxic carrier. A solubilizing agent, an emulsifying agent (for example, an ethoxylated isostearyl alcohol or a polyoxyethylene sorbitol ester), a preservative, a flavor-imparting agent (for example, peppermint oil or saccharin), or any other additive may also be added if necessary.

A unit dosage formulation for an oral administration may be formulated as a microcapsule if necessary. Such a formulation may be coated or embedded in a polymer, a wax or the like to achieve a prolonged action or a sustained release.

Rectal administration can be accomplished by using a suppository obtained by mixing the inventive compound with a water-soluble or water-insoluble solid having a low melting point such as polyethylene glycol, cocoa butter, a higher ester (for example, myristyl palmitate) and a mixture thereof.

Intra-tis sue administration can be accomplished by using a liquid unit dosage form, for example in the form of a solution or a suspension as a subcutaneous, intramuscular, intrabladder or intravenous injection formulation. Any of these formulations can be produced by suspending or dissolving a certain amount of the inventive compound in a non-toxic liquid carrier suitable for the purpose of the injection such as an aqueous or oily vehicle followed by sterilizing the resulting suspension or solution. Alternatively, a certain amount of the inventive compound may be placed in a vial, which is then sterilized together with its content and then sealed. An auxiliary vial and a carrier may be provided in combination with a powdered or lyophilized active ingredient for the purpose of dissolving or mixing just before administration. A non-toxic salt or salt solution may be added for the purpose of making an injection solution isotonic. It is also possible to use a stabilizer, a preservative, an emulsifying agent or the like in combination.

Transdermal administration can be accomplished in a solid or liquid dosage unit such as an aerosol, a liquid, a suspension, an emulsion, an adhesive preparation, anointment, a cataplasm, a liniment, a lotion or another dosage form.

An ointment is produced by, for example, mixing and kneading a certain amount of the inventive compound with a pharmaceutically acceptable solid base suitable for an ointment, for example, a water-soluble base or a lipid-soluble base described in the Japanese pharmacopoeia. It is also possible to use an additive such as a stabilizer, a preservative, an emulsifying agent or a suspending agent.

Instillation can be accomplished in a liquid unit dosage form, for example, in the form of a solution or a suspension. Any of these formulations can be produced by suspending or dissolving a certain amount of the inventive compound in a non-toxic liquid carrier suitable for instillation such as an aqueous or oily vehicle followed by sterilizing the resulting suspension or solution. Alternatively, a certain amount of the inventive compound may be placed in a vial, which is then sterilized together with its content and then sealed. An auxiliary vial and a carrier may be provided in combination with a powdered or lyophilized active ingredient for the purpose of dissolving or mixing just before administration. A pharmaceutically acceptable salt or salt solution may be added for the purpose of making an eye drop isotonic. It is also possible to use a stabilizer, a preservative, an emulsifying agent or the like in combination.

EXAMPLES

Hereinafter, the present invention will be described in more detail with reference to Reference examples, Examples, Test examples and Preparation examples. However, the invention is not limited only to these.

Reference Example 1

4-{[(1S,2R)-2-aminocyclohexyl]amino}-N-(2-methoxyethyl)-6-methylquinazolin-2-carboxamide Step 1: tert-butyl{(1R,2S)-2-[(2-{[(2-methoxyethyl)amino]carbonyl}-6-methylquinazolin-4-yl)amino]cyclohexyl}carbamate To a suspension of 15.0 g of ethyl 4-({(1S,2R)-2-[(tert-butoxycarbonyl)amino]cyclohexyl}amino-6-methylquinazolin-2-carboxylate in 15 ml of methanol, 7.89 g of 2-methoxyethylamine was added, and the mixture was stirred at 50° C. for 15 hours. After the reaction solution was cooled to room temperature, 45 ml of diisopropyl ether was added thereto, and the mixture was stirred at 0° C. for 30 minutes. The deposited crystal was collected by filtration, washed with diisopropyl ether and dried under reduced pressure, whereby 12.2 g of a desired compound was obtained as a white powder.

Step 2: 4-{[(1S,2R)-2-aminocyclohexyl]amino}-N-(2-methoxyethyl)-6-methylquinazolin-2-carboxamide To a suspension of 2.24 g of tert-butyl {(1R,2S)-2-[(2-{[(2-methoxyethyl)amino]carbonyl}-6-methylquinazolin-4-yl)amino]cyclohexyl}carbamate in 10 ml of ethyl acetate, 10 ml of a 4 N hydrogen chloride-ethyl acetate solution was added, and the mixture was stirred at room temperature for 48 hours. To the reaction solution, 20 ml of diethyl ether was added, and the mixture was stirred for 30 minutes. Then, the deposited substance was collected by filtration, washed with diethyl ether and dried under reduced pressure. The resulting powder was purified by Fuji Silysia NH silica gel column chromatography (chloroform:methanol=20:1), whereby 1.61 g of a desired compound was obtained as a colorless powder.

Example 1

4-{[(1S,2R)-2-(ethanimidoylamino)cyclohexyl]amino}-N-(2-methoxyethyl)-6-methylquinazolin-2-carboxamide dihydrochloride Step 1: 4-{[(1S,2R)-2-(ethanimidoylamino)cyclohexyl]amino}-N-(2-methoxyethyl)-6-methylquinazolin-2-carboxamide To a solution of 450 mg of 4-{[(1S,2R)-2-aminocyclohexyl]amino}-N-(2-methoxyethyl)-6-methylquinazolin-2-carboxamide and 467 mg of ethylacetoimidate hydrochloride in 10 ml of ethanol, 764 mg of triethylamine was added, and the mixture was stirred at 80° C. for 8 hours. After the reaction solution was concentrated, the residue was purified by silica gel column chromatography (chloroform:methanol=20:1), whereby 391 mg of a desired compound was obtained as a pale yellow powder.

Step 2: 4-{[(1S,2R)-2-(ethanimidoylamino)cyclohexyl]amino}-N-(2-methoxyethyl)-6-methylquinazolin-2-carboxamide dihydrochloride To a solution of 391 mg of 4-{[(1S,2R)-2-(ethanimidoylamino)cyclohexyl]amino}-N-(2-methoxyethyl)-6-methylquinazolin-2-carboxamide in 5 ml of ethyl acetate, 3 ml of a 4 N hydrogen chloride-ethyl acetate solution was added, and the mixture was stirred for 10 minutes. Then, to the reaction solution, 10 ml of diethyl ether was added, and the deposited substance was collected by filtration, washed with diethyl ether and dried under reduced pressure, whereby 405 mg of a desired compound was obtained as a white powder.

Elemental analysis value (as $C_{21}H_{30}N_6O_2/2HCl/2.5;H_2O$)
Calculated (%) C, 48.84; H, 7.22; N, 16.27.
Found (%) C, 48.69; H, 6.83; N, 16.04.
Positive ion FAB-MS m/z: 399 [M+H]$^+$
Specific rotation $[\alpha]^{20}_D$=+110.79 (c=0.500 methanol)

In the same manner as in Example 1, the following compounds of Examples 2 to 207 were produced.

Example 2

6-chloro-N-cycloheptyl-4-[((1S,2R)-2-{[2-(2-furyl)ethanimidoyl]amino}cyclohexyl)amino]quinazolin-2-carboxamide dihydrochloride Elemental analysis value (as $C_{28}H_{35}N_6O_2Cl/2HCl/1.3H_2O$)
Calculated (%) C, 54.29; H, 6.44; N, 13.57.
Found (%) C, 54.22; H, 6.37; N, 13.55.
Positive ion FAB-MS m/z: 523 [M+H]$^+$
Specific rotation $[\alpha]^{20}_D$=+108.73 (c=0.504 methanol)
Appearance: pale red powder

Example 3

6-chloro-N-cycloheptyl-4-({(1S,2R)-2-[(2-pyridin-2-ylethan imidoyl)amino]cyclohexyl}amino)quinazolin-2-carboxamide trihydrochloride Elemental analysis value (as $C_{29}H_{36}N_7OCl/3HCl/3.1H_2O$)
Calculated (%) C, 49.81; H, 6.52; N, 14.02.
Found (%) C, 49.81; H, 6.46; N, 13.80.
Positive ion FAB-MS m/z: 534 [M+H]$^+$
Specific rotation $[\alpha]^{20}_D$=+58.40 (c=0.565 methanol)
Appearance: pale brown powder

Example 4

4-{[(1S,2R)-2-(n-butanimidoylamino)cyclohexyl]amino}-6-chloro-N-cycloheptylquinazolin-2-carboxamide dihydrochloride Elemental analysis value (as $C_{26}H_{37}N_6OCl/2HCl/1.8H_2O$)
Calculated (%) C, 52.89; H, 7.27; N, 14.23.
Found (%) C, 52.90; H, 7.22; N, 13.98.
Positive ion FAB-MS m/z: 485 [M+H]$^+$
Specific rotation $[\alpha]^{20}_D$=+93.61 (c=0.517 methanol)
Appearance: white powder

Example 5

N-(2-ethylbutyl)-4-({(1S,2R)-2-[(2-methoxyethanimidoyl)amino]cyclohexyl}amino)-6-methylquinazolin-2-carboxamide dihydrochloride Elemental analysis value (as $C_{25}H_{38}N_6O_2/2HCl/0.9H_2O$)
Calculated (%) C, 55.22; H, 7.75; N, 15.46.
Found (%) C, 55.21; H, 7.62; N, 15.44.
Positive ion FAB-MS m/z: 387 [M+H]$^+$
Specific rotation $[\alpha]^{20}_D$=+96.52 (c=0.518 methanol)
Appearance: white powder

Example 6

N-(2-ethylbutyl)-4-({(1S,2R)-2-[(3-methoxypropanimidoyl)amino]cyclohexyl}amino)-6-methylquinazolin-2-carboxamide dihydrochloride Elemental analysis value (as $C_{26}H_{40}N_6O_2/2HCl/0.8H_2O$)
Calculated (%) C, 56.17; H, 7.90; N, 15.12.
Found (%) C, 56.22; H, 7.84; N, 14.96.
Positive ion FAB-MS m/z: 469 [M+H]$^+$
Specific rotation $[\alpha]^{20}_D$=+94.93 (c=0.533 methanol)
Appearance: white powder

Example 7

N-(3-methoxy-2,2-dimethylpropyl)-4-({(1S,2R)-2-[(3-methoxy propanimidoyl)amino]cyclohexyl}amino)-6-methylquinazolin-2-carboxamide dihydrochloride Elemental analysis value (as $C_{26}H_{40}N_6O_3/2HCl/0.8H_2O$)
Calculated (%) C, 54.60; H, 7.68; N, 14.69.
Found (%) C, 54.63; H, 7.59; N, 14.59.
Positive ion FAB-MS m/z: 485 [M+H]$^+$
Specific rotation $[\alpha]^{20}_D$=+84.57 (c=0.525 methanol)
Appearance: white powder

Example 8

N-(2,2-dimethylpropyl)-4-({(1S,2R)-2-[(2-methoxyethanimidoyl)amino]cyclohexyl}amino)-6-methylquinazolin-2-carboxamide dihydrochloride Positive ion FAB-MS m/z: 441 [M+H]$^+$
Specific rotation $[\alpha]^{20}_D$=+98.12 (c=0.534 methanol)
Appearance: white powder

Example 9

N-(2,2-dimethylpropyl)-4-[((1S,2R)-2-{[2-(2-furyl)ethanimidoyl]amino}cyclohexyl)amino]-6-methylquinazolin-2-carboxamide dihydrochloride Positive ion FAB-MS m/z: 477 [M+H]$^+$
Specific rotation $[\alpha]^{20}_D$=+89.57 (c=0.547 methanol)
Appearance: red-brown powder

Example 10

N-(2,2-dimethylpropyl)-4-({(1S,2R)-2-[(3-methoxypropanimidoyl)amino]cyclohexyl}amino)-6-methylquinazolin-2-carboxamide dihydrochloride Elemental analysis value (as $C_{25}H_{38}N_6O_2/2HCl/0.9H_2O$)
Calculated (%) C, 55.22; H, 7.75; N, 15.46.
Found (%) C, 55.28; H, 7.52; N, 15.15.
Positive ion FAB-MS m/z: 455 [M+H]$^+$
Specific rotation $[\alpha]^{20}_D$=+87.07 (c=0.526 methanol)
Appearance: white powder

Example 11

4-[((1S,2R)-2-{[3-(dimethylamino)propanimidoyl]amino}cyclohexyl)amino]-N-(2,2-dimethylpropyl)-6-methylquinazolin-2-carboxamide trihydrochloride Elemental analysis value (as $C_{26}H_{41}N_7O/3HCl/1.8H_2O$)
Calculated (%) C, 51.24; H, 7.87; N, 16.09.
Found (%) C, 51.48; H, 7.49; N, 15.68.
Positive ion FAB-MS m/z: 468 [M+H]$^+$
Specific rotation $[\alpha]^{20}_D$=+57.14 (c=0.469 methanol)
Appearance: white powder

Example 12

4-({(1S,2R)-2-[(2-methoxyethanimidoyl)amino]cyclohexyl}amino)-6-methyl-N-(2,2,2-trifluoroethyl)quinazolin-2-carboxamide dihydrochloride Positive ion FAB-MS m/z: 453 [M+H]$^+$
Specific rotation $[\alpha]^{20}_D$=+116.73 (c=0.514 methanol)
Appearance: pale brownish white powder

Example 13

N-(trans-4-methoxycyclohexyl)-4-({(1S,2R)-2-[(2-methoxyethanimidoyl)amino]cyclohexyl}amino)-6-methylquinazolin-2-carboxamide dihydrochloride Elemental analysis value (as $C_{26}H_{38}N_6O_3/2HCl/1.8H_2O$)
Calculated (%) C, 53.11; H, 7.47; N, 14.29.
Found (%) C, 53.24; H, 7.41; N, 13.92.
Positive ion FAB-MS m/z: 483 [M+H]$^+$
Specific rotation $[\alpha]^{20}_D$=+105.05 (c=0.495 methanol)
Appearance: white powder

Example 14

N-(2,2-dimethylpropyl)-6-fluoro-4-({(1S,2R)-2-[(2-methoxyethanimidoyl)amino]cyclohexyl}amino)quinazolin-2-carboxamide dihydrochloride Positive ion FAB-MS m/z: 445 [M+H]$^+$
Specific rotation $[\alpha]^{20}_D$=+63.03 (c=0.514 methanol)
Appearance: white powder

Example 15

N-(2,2-dimethylpropyl)-4-({(1S,2R)-2-[(2-ethoxyethanimidoyl)amino]cyclohexyl}amino)-6-methylquinazolin-2-carboxamide dihydrochloride Positive ion FAB-MS m/z: 455 [M+H]$^+$
Specific rotation $[\alpha]^{20}_D$=+92.51 (c=0.521 methanol)
Appearance: white powder

Example 16

N-(2,2-dimethylpropyl)-4-({(1S,2R)-2-[(2-ethoxyethanimidoyl)amino]cyclohexyl}amino)-6-fluoroquinazolin-2-carboxamide dihydrochloride Elemental analysis value (as $C_{24}H_{35}N_6O_2F/2HCl/0.9H_2O$)

Calculated (%) C, 52.63; H, 7.14; N, 15.34.
Found (%) C, 52.76; H, 7.15; N, 15.25.
Positive ion FAB-MS m/z: 459 [M+H]$^+$
Specific rotation $[\alpha]^{20}_D$=+55.25 (c=0.514 methanol)
Appearance: white powder

Example 17

N-(2-ethylbutyl)-6-fluoro-4-({(1S,2R)-2-[(2-methoxyethanimidoyl)amino]cyclohexyl}amino)quinazolin-2-carboxamide dihydrochloride Elemental analysis value (as $C_{24}H_{35}N_6O_2F$/2HCl/H$_2$O)
Calculated (%) C, 52.46; H, 7.15; N, 15.29.
Found (%) C, 52.65; H, 7.10; N, 15.21.
Positive ion FAB-MS m/z: 459 [M+H]$^+$
Specific rotation $[\alpha]^{20}_D$=+59.34 (c=0.492 methanol)
Appearance: white powder

Example 18

6-fluoro-N-(3-methoxy-2,2-dimethylpropyl)-4-({(1S,2R)-2-[(2-methoxyethanimidoyl)amino]cyclohexyl}amino)quinazolin-2-carboxamide dihydrochloride Positive ion FAB-MS m/z: 475 [M+H]$^+$
Specific rotation $[\alpha]^{20}_D$=+54.82 (c=0.518 methanol)
Appearance: white powder

Example 19

N-(2,2-dimethylpropyl)-4-({(1S,2R)-2-[(2-methoxy-2-methylpropanimidoyl)amino]cyclohexyl}amino)-6-methylquinazolin-2-carboxamide dihydrochloride Elemental analysis value (as $C_{26}H_{40}N_6O_2$/2HCl/0.9H$_2$O)
Calculated (%) C, 55.99; H, 7.92; N, 15.07.
Found (%) C, 55.94; H, 7.81; N, 15.07.
Positive ion FAB-MS m/z: 469 [M+H]$^+$
Specific rotation $[\alpha]^{20}_D$=+5.49 (c=0.510 methanol)
Appearance: white powder

Example 20

6-fluoro-N-isobutyl-4-({(1S,2R)-2-[(2-methoxyethanimidoyl)amino]cyclohexyl}amino)quinazolin-2-carboxamide dihydrochloride Elemental analysis value (as $C_{22}H_{31}N_6O_2F$/2HCl/1.1H$_2$O)
Calculated (%) C, 50.50; H, 6.78; N, 16.06.
Found (%) C, 50.48; H, 6.69; N, 16.03.
Positive ion FAB-MS m/z: 431 [M+H]$^+$
Specific rotation $[\alpha]^{20}_D$=+66.42 (c=0.557 methanol)
Appearance: white powder

Example 21

N-[(1-hydroxycyclohexyl)methyl]-4-({(1S,2R)-2-[(2-methoxyethanimidoyl)amino]cyclohexyl}amino)-6-methylquinazolin-2-carboxamide dihydrochloride Elemental analysis value (as $C_{26}H_{38}N_6O_3$/2HCl/2.1H$_2$O)
Calculated (%) C, 52.63; H, 7.51; N, 14.16.
Found (%) C, 52.57; H, 7.12; N, 14.15.
Positive ion FAB-MS m/z: 483 [M+H]$^+$
Specific rotation $[\alpha]^{20}_D$=+98.10 (c=0.581 methanol)
Appearance: white powder

Example 22

4-({(1S,2R)-2-[(2-methoxyethanimidoyl)amino]cyclohexyl}amino)-N-[2-methoxy-1-(methoxymethyl)-1-methylethyl]-6-methyl quinazolin-2-carboxamide dihydrochloride Elemental analysis value (as $C_{25}H_{38}N_6O_4$/2HCl/1.8H$_2$O)
Calculated (%) C, 50.73; H, 7.42; N, 14.20.
Found (%) C, 50.84; H, 7.17; N, 14.46.
Positive ion FAB-MS m/z: 487 [M+H]$^+$
Specific rotation $[\alpha]^{20}_D$=+99.62 (c=0.532 methanol)
Appearance: white powder

Example 23

4-({(1S,2R)-2-[(2-methoxyethanimidoyl)amino]cyclohexyl}amino)-N-(2-methoxy-2-methylpropyl)-6-methylquinazolin-2-carb oxamide dihydrochloride Positive ion FAB-MS m/z: 457 [M+H]$^+$
Specific rotation $[\alpha]^{20}_D$=+99.99 (c=0.542 methanol)
Appearance: white powder

Example 24

4-{[(1S,2R)-2-(ethanimidoylamino)cyclohexyl]amino}-N-(2-methoxy-2-methylpropyl)-6-methylquinazolin-2-carboxamide dihydrochloride Elemental analysis value (as $C_{23}H_{34}N_6O_2$/2HCl/3H$_2$O)
Calculated (%) C, 49.91; H, 7.65; N, 15.18.
Found (%) C, 49.94; H, 7.49; N, 15.09.
Positive ion FAB-MS m/z: 427 [M+H]$^+$
Specific rotation $[\alpha]^{20}_D$=+94.18 (c=0.516 methanol)
Appearance: white powder

Example 25

4-{[(1S,2R)-2-(ethanimidoylamino)cyclohexyl]amino}-N-(2-hydroxy-2-methylpropyl)-6-methylquinazolin-2-carboxamide dihydrochloride Elemental analysis value (as $C_{22}H_{32}N_6O_2$/2HCl/3.4H$_2$O)
Calculated (%) C, 48.33; H, 7.52; N, 15.37.
Found (%) C, 48.27; H, 7.22; N, 15.26.
Positive ion FAB-MS m/z: 413 [M+H]$^+$
Specific rotation $[\alpha]^{20}_D$=+92.24 (c=0.529 methanol)
Appearance: white powder

Example 26

4-{[(1S,2R)-2-(ethanimidoylamino)cyclohexyl]amino}-N-[(1-hydroxycyclohexyl)methyl]-6-methylquinazolin-2-carboxamide dihydrochloride Elemental analysis value (as $C_{25}H_{36}N_6O_2$/2HCl/2H$_2$O)
Calculated (%) C, 52.63; H, 7.60; N, 14.73.
Found (%) C, 52.45; H, 7.41; N, 14.83.
Positive ion FAB-MS m/z: 453 [M+H]$^+$
Specific rotation $[\alpha]^{20}_D$=+84.35 (c=0.569 methanol)
Appearance: white powder

Example 27

4-({(1S,2R)-2-[(2-methoxy-2-methylpropanimidoyl)amino]cyclohexyl}amino)-N-(2-methoxy-2-methylpropyl)-6-methylquinazolin-2-carboxamide dihydrochloride Elemental analysis value (as $C_{26}H_{40}N_6O_3/2HCl/H_2O$)
Calculated (%) C, 54.26; H, 7.71; N, 14.60.
Found (%) C, 54.38; H, 7.46; N, 14.24.
Positive ion FAB-MS m/z: 485 [M+H]$^+$
Specific rotation $[\alpha]^{20}_D$=+5.61 (c=0.534 methanol)
Appearance: white powder

Example 28

4-{[(1S,2R)-2-(ethanimidoylamino)cyclohexyl]amino}-N-[2-methoxy-1-(methoxymethyl)ethyl]-6-methylquinazolin-2-carboxamide dihydrochloride Elemental analysis value (as $C_{23}H_{34}N_6O_3/2HCl/2.1H_2O$)
Calculated (%) C, 49.93; H, 7.32; N, 15.19.
Found (%) C, 49.95; H, 7.19; N, 14.96.
Positive ion FAB-MS m/z: 443 [M+H]$^+$
Specific rotation $[\alpha]^{20}_D$=+106.37 (c=0.549 methanol)
Appearance: white powder

Example 29

4-[((1S,2R)-2-{[3-(dimethylamino)propanimidoyl]amino}cyclohexyl)amino]-N-(2-methoxy-2-methylpropyl)-6-methylquinazolin-2-carboxamide dihydrochloride Positive ion FAB-MS m/z: 484 [M+H]$^+$
Specific rotation $[\alpha]^{20}_D$=+61.43 (c=0.599 methanol)
Appearance: white powder

Example 30

4-({(1S,2R)-2-[(2-methoxy-2-methylpropanimidoyl)amino]cyclohexyl}amino)-N-(3-methoxypropyl)-6-methylquinazolin-2-carboxamide dihydrochloride Elemental analysis value (as $C_{25}H_{38}N_6O_3/2HCl/H_2O$)
Calculated (%) C, 53.47; H, 7.54; N, 14.97.
Found (%) C, 53.52; H, 7.24; N, 14.92.
Positive ion FAB-MS m/z: 471 [M+H]$^+$
Specific rotation $[\alpha]^{20}_D$=+9.52 (c=0.588 methanol)
Appearance: white powder

Example 31

N-(2-methoxy-2-methylpropyl)-4-({(1S,2R)-2-[(3-methoxypropanimidoyl)amino]cyclohexyl}amino)-6-methylquinazolin-2-carboxamide dihydrochloride Elemental analysis value (as $C_{25}H_{38}N_6O_3/2HCl/3.3H_2O$)
Calculated (%) C, 49.80; H, 7.79; N, 13.94.
Found (%) C, 49.48; H, 7.37; N, 13.75.
Positive ion FAB-MS m/z: 471 [M+H]$^+$
Specific rotation $[\alpha]^{20}_D$=+97.21 (c=0.574 methanol)
Appearance: white powder

Example 32

N-(2-methoxyethyl)-4-({(1S,2R)-2-[(2-methoxy-2-methylpropanimidoyl)amino]cyclohexyl}amino)-6-methylquinazolin-2-carb oxamide dihydrochloride Elemental analysis value (as $C_{24}H_{36}N_6O_3/2HCl/2.3H_2O$)
Calculated (%) C, 50.49; H, 7.52; N, 14.72.
Found (%) C, 50.59; H, 7.23; N, 14.78.
Positive ion FAB-MS m/z: 457 [M+H]$^+$
Specific rotation $[\alpha]^{20}_D$=+21.54 (c=0.557 methanol)
Appearance: white powder

Example 33

N-isobutyl-4-({(1S,2R)-2-[(2-methoxy-2-methylpropanimidoyl)amino]cyclohexyl}amino)-6-methylquinazolin-2-carboxamide dihydrochloride Elemental analysis value (as $C_{25}H_{38}N_6O_2/2HCl/2.3H_2O$)
Calculated (%) C, 52.77; H, 7.90; N, 14.77.
Found (%) C, 52.74; H, 7.53; N, 14.79.
Positive ion FAB-MS m/z: 455 [M+H]$^+$
Specific rotation $[\alpha]^{20}_D$=+5.92 (c=0.540 methanol)
Appearance: white powder

Example 34

N-(2-methoxyethyl)-4-({(1S,2R)-2-[(3-methoxypropanimidoyl)amino]cyclohexyl}amino)-6-methylquinazolin-2-carboxamide dihydrochloride Positive ion FAB-MS m/z: 443 [M+H]$^+$
Specific rotation $[\alpha]^{20}_D$=+113.09 (c=0.527 methanol)
Appearance: white powder

Example 35

4-({(1S,2R)-2-[(3-methoxypropanimidoyl)amino]cyclohexyl}amino)-N-(3-methoxypropyl)-6-methylquinazolin-2-carboxamide dihydrochloride Positive ion FAB-MS m/z: 457 [M+H]$^+$
Specific rotation $[\alpha]^{20}_D$=+107.53 (c=0.571 methanol)
Appearance: white powder

Example 36

N-ethyl-4-({(1S,2R)-2-[(3-methoxypropanimidoyl)amino]cyclo hexyl}amino)-6-methylquinazolin-2-carboxamide dihydrochloride Positive ion FAB-MS m/z: 413 [M+H]$^+$
Specific rotation $[\alpha]^{20}_D$=+122.56 (c=0.545 methanol)
Appearance: white powder

Example 37

4-{[(1S,2R)-2-(ethanimidoylamino)cyclohexyl]amino}-N-(4-methoxyphenyl)-6-methylquinazolin-2-carboxamide dihydrochloride Elemental analysis value (as $C_{25}H_{30}N_6O_2/2HCl/1.5H_2O$)
Calculated (%) C, 54.95; H, 6.46; N, 15.38.
Found (%) C, 55.26; H, 6.11; N, 15.31.
Positive ion FAB-MS m/z: 447 [M+H]$^+$
Specific rotation $[\alpha]^{20}_D$=+28.47 (c=0.576 methanol)
Appearance: pale yellow powder

Example 38

N-n-butyl-4-{[(1S,2R)-2-(ethanimidoylamino)cyclohexyl]amino}-6-methylquinazolin-2-carboxamide dihydrochloride Elemental analysis value (as $C_{22}H_{32}N_6O/2HCl/1.2H_2O$)
Calculated (%) C, 53.81; H, 7.47; N, 17.11.
Found (%) C, 53.80; H, 7.31; N, 17.22.
Positive ion FAB-MS m/z: 397 [M+H]$^+$
Specific rotation $[\alpha]^{20}_D$=+96.42 (c=0.728 methanol)
Appearance: white powder

Example 39

N-n-butyl-6-methl-4-({(1S,2R)-2-[(2-methylpropanimidoyl)amino]cyclohexyl}amino)quinazolin-2-carboxamide dihydrochloride Elemental analysis value (as $C_{24}H_{36}N_6O/2HCl/0.8H_2O$)
Calculated (%) C, 56.31; H, 7.80; N, 16.42.
Found (%) C, 55.99; H, 7.37; N, 16.54.
Positive ion FAB-MS m/z: 425 [M+H]$^+$
Specific rotation $[\alpha]^{20}_D$=+1.20 (c=0.662 methanol)
Appearance: white powder

Example 40

N-n-butyl-4-[((1S,2R)-2-{[cyclohexyl(imino)methyl]amino}cyclohexyl)amino]-6-methylquinazolin-2-carboxamide dihydrochloride Elemental analysis value (as $C_{27}H_{40}N_6O/2HCl/1.2H_2O$)
Calculated (%) C, 57.99; H, 8.00; N, 15.03.
Found (%) C, 58.02; H, 7.72; N, 15.14.
Positive ion FAB-MS m/z: 465 [M+H]$^+$
Specific rotation $[\alpha]^{20}_D$=+1.50 (c=0.665 methanol)
Appearance: white powder

Example 41

N-(4-methoxyphenyl)-6-methyl-4-({(1S,2R)-2-[(2-phenylethan imidoyl)amino]cyclohexyl}amino)quinazolin-2-carboxamide dihydrochloride Elemental analysis value (as $C_{31}H_{34}N_6O_2/2HCl/0.8H_2O$)
Calculated (%) C, 61.04; H, 6.21; N, 13.78.
Found (%) C, 61.07; H, 6.00; N, 13.89.
Positive ion FAB-MS m/z: 523 [M+H]$^+$
Specific rotation $[\alpha]^{20}_D$=+79.81 (c=0.649 methanol)
Appearance: pale yellow powder

Example 42

N-n-butyl-6-methyl-4-[((1S,2R)-2-{[N-phenylethanimidoyl]amino}cyclohexyl)amino]quinazolin-2-carboxamide dihydrochloride Positive ion FAB-MS m/z: 473 [M+H]$^+$
Appearance: white powder

Example 43

N-(2,2-dimethylpropyl)-6-methyl-4-[((1S,2R)-2-{[N-methylethanimidoyl]amino}cyclohexyl)amino]quinazolin-2-carboxamide dihydrochloride Elemental analysis value (as $C_{24}H_{36}N_6O/2HCl/0.8H_2O$)
Calculated (%) C, 56.31; H, 7.80; N, 16.42.
Found (%) C, 56.44; H, 7.75; N, 16.21.
Positive ion FAB-MS m/z: 425 [M+H]$^+$
Specific rotation $[\alpha]^{20}_D$=+81.03 (c=0.501 methanol)
Appearance: white powder

Example 44

4-({(1S,2R)-2-[(3-hydroxypropanimidoyl)amino]cyclohexyl}amino)-N-isobutyl-6-methylquinazolin-2-carboxamide dihydrochloride Positive ion FAB-MS m/z: 427 [M+H]$^+$
Specific rotation $[\alpha]^{20}_D$=+102.72 (c=0.514 methanol)
Appearance: pale yellow powder

Example 45

N-(2,2-dimethylpropyl)-4-({(1S,2R)-2-[(3-hydroxypropanimidoyl)amino]cyclohexyl}amino)-6-methylquinazolin-2-carboxamide dihydrochloride Positive ion FAB-MS m/z: 441 [M+H]$^+$
Specific rotation $[\alpha]^{20}_D$=+58.24 (c=0.546 methanol)
Appearance: pale yellow powder

Example 46

4-({(1S,2R)-2-[(3-hydroxypropanimidoyl)amino]cyclohexyl}amino)-N-(trans-4-methoxycyclohexyl)-6-methylquinazolin-2-carboxamide dihydrochloride Positive ion FAB-MS m/z: 483 [M+H]$^+$
Specific rotation $[\alpha]^{20}_D$=+82.74 (c=0.539 methanol)
Appearance: white powder

Example 47

4-{[(1S,2R)-2-(ethanimidoylamino)cyclohexyl]amino}-6-fluoro-N-(trans-4-methoxycyclohexyl)quinazolin-2-carboxamide dihydrochloride Elemental analysis value (as $C_{24}H_{33}FN_6O_2/2HCl/2H_2O$)
Calculated (%) C, 50.97; H, 6.95; N, 14.86.
Found (%) C, 51.07; H, 6.79; N, 15.07.
Positive ion FAB-MS m/z: 457 [M+H]$^+$
Specific rotation $[\alpha]^{20}_D$=+48.29 (c=0.468 methanol)
Appearance: white powder

Example 48

6-fluoro-N-(trans-4-methoxycyclohexyl)-4-({(1S,2R)-2-[(2-m ethoxyethanimidoyl)amino]cyclohexyl}amino)quinazolin-2-carboxamide dihydrochloride Elemental analysis value (as $C_{25}H_{35}FN_6O_3/2HCl/1.7H_2O$)
Calculated (%) C, 50.88; H, 6.90; N, 14.24.
Found (%) C, 50.97; H, 6.59; N, 14.20.

Positive ion FAB-MS m/z: 487 [M+H]$^+$
Specific rotation [α]$^{20}_D$=+69.09 (c=0.605 methanol)
Appearance: white powder

Example 49

4-{[(1S,2R)-2-(ethanimidoylamino)cyclohexyl]
amino}-6-methyl-N-[2-(methylthio)ethyl]quinazo-
lin-2-carboxamide dihydrochloride Positive ion FAB-MS m/z: 415 [M+H]$^+$
Specific rotation [α]$^{20}_D$=+90.97 (c=0.565 methanol)
Appearance: white powder

Example 50

4-({(1S,2R)-2-[(2-methoxyethanimidoyl)amino]
cyclohexyl}amino)-6-methyl-N-[2-(methylthio)
ethyl]quinazolin-2-carboxamide dihydrochloride Positive ion FAB-MS m/z: 445 [M+H]$^+$
Specific rotation [α]$^{20}_D$=+105.81 (c=0.550 methanol)
Appearance: white powder

Example 51

4-{[(1S,2R)-2-(ethanimidoylamino)cyclohexyl]
amino}-N-(2-methoxy-1,1-dimethylethyl)-6-meth-
ylquinazolin-2-carboxamide dihydrochloride Elemental analysis value (as $C_{23}H_{34}N_6O_2$/2HCl/2H$_2$O)
Calculated (%) C, 51.59; H, 7.53; N, 15.69.
Found (%) C, 51.53; H, 7.23; N, 15.63.
Positive ion FAB-MS m/z: 427 [M+H]$^+$
Specific rotation [α]$^{20}_D$=+90.94 (c=0.530 methanol)
Appearance: pale yellow powder

Example 52

N-(2-methoxy-1,1-dimethylethyl)-4-({(1S,2R)-2-[(2-
methoxyethanimidoyl)amino]cyclohexyl}amino)-6-
methylquinazolin-2-carboxamide dihydrochloride Elemental analysis value (as $C_{24}H_{36}FN_6O_3$/2HCl/1.8H$_2$O)
Calculated (%) C, 51.30; H, 7.46; N, 14.96.
Found (%) C, 51.38; H, 7.18; N, 15.16
Positive ion FAB-MS m/z: 457 [M+H]$^+$
Specific rotation [α]$^{20}_D$=+107.93 (c=0.580 methanol)
Appearance: white powder

Example 53

4-{[(1S,2R)-2-(ethanimidoylamino)cyclohexyl]
amino}-N-isobutyl-6-methoxyquinazolin-2-carboxa-
mide dihydrochloride Elemental analysis value (as $C_{22}H_{32}N_6O_2$/2HCl/2.8H$_2$O)
Calculated (%) C, 49.31; H, 7.45; N, 15.68.
Found (%) C, 49.27; H, 7.10; N, 15.33.
Positive ion FAB-MS m/z: 413 [M+H]$^+$
Specific rotation [α]$^{20}_D$=+123.21 (c=0.560 methanol)
Appearance: pale yellow powder

Example 54

N-isobutyl-6-methoxy-4-({(1S,2R)-2-[(2-methoxy-
ethanimidoyl)amino]cyclohexyl}amino)quinazolin-
2-carboxamide dihydrochloride Positive ion FAB-MS m/z: 443 [M+H]$^+$
Specific rotation [α]$^{20}_D$=+130.87 (c=0.570 methanol)
Appearance: white powder

Example 55

4-({(1S,2R)-2-[(3-hydroxypropanimidoyl)amino]
cyclohexyl}amino)-N-(2-methoxy-1,1-dimethyl-
ethyl)-6-methylquinazolin-2-carboxamide dihydro-
chloride Elemental analysis value (as $C_{24}H_{36}N_6O_3$/2HCl/2.4H$_2$O)
Calculated (%) C, 50.33; H, 7.53; N, 14.67.
Found (%) C, 50.25; H, 7.30; N, 14.74.
Positive ion FAB-MS m/z: 457 [M+H]$^+$
Specific rotation [α]$^{20}_D$=+91.69 (c=0.530 methanol)
Appearance: pale yellow powder

Example 56

4-{[(1S,2R)-2-(ethanimidoylamino)cyclohexyl]
amino}-6-methyl-[3-(methylthio)propyl]quinazolin-
2-carboxamide dihydrochloride Elemental analysis value (as $C_{22}H_{32}N_6OS$/2HCl/2.2H$_2$O)
Calculated (%) C, 48.83; H, 7.15; N, 15.53.
Found (%) C, 48.77; H, 6.76; N, 15.23.
Positive ion FAB-MS m/z: 429 [M+H]$^+$
Specific rotation [α]$^{20}_D$=+81.55 (c=0.645-methanol)
Appearance: pale yellow powder

Example 57

4-({(1S,2R)-2-[(3-hydroxypropanimidoyl)amino]
cyclohexyl}amino)-6-methyl-N-(2,2,2-trifluoroethyl)
quinazolin-2-carboxamide dihydrochloride Positive ion FAB-MS m/z: 453 [M+H]$^+$
Specific rotation [α]$^{20}_D$=+109.54 (c=0.555 methanol)
Appearance: pale yellow powder

Example 58

4-({(1S,2R)-2-[(3-hydroxypropanimidoyl)amino]
cyclohexyl}amino)-N-isopropyl-6-methylquinazolin-
2-carboxamide dihydrochloride Positive ion FAB-MS m/z: 413 [M+H]$^+$
Specific rotation [α]$^{20}_D$=+108.07 (c=0.570 methanol)
Appearance: pale yellow powder

Example 59

4-({(1S,2R)-2-[(3-hydroxypropanimidoyl)amino]
cyclohexyl}amino)-N-(3-methoxypropyl)-6-meth-
ylquinazolin-2-carboxamide dihydrochloride Elemental analysis value (as $C_{23}H_{34}N_6O_3$/2HCl/3.4H$_2$O)
Calculated (%) C, 47.90; H, 7.48; N, 14.57.
Found (%) C, 48.24; H, 7.34; N, 14.22.
Positive ion FAB-MS m/z: 443 [M+H]$^+$ Specific rotation $[\alpha]^{20}_D$=+89.92 (c=0.685 methanol)
Appearance: pale yellow powder

Example 60

4-({(1S,2R)-2-[(2-hydroxy-2-methylpropanimidoyl)amino]cyclohexyl}amino)-N-isobutyl-6-methylquinazolin-2-carboxamide dihydrochloride Positive ion FAB-MS m/z: 441 [M+H]$^+$
Specific rotation $[\alpha]^{20}_D$=+27.49 (c=0.560 methanol)
Appearance: white powder

Example 61

N-(2-ethoxyethyl)-4-({(1S,2R)-2-[(3-hydroxypropanimidoyl)amino]cyclohexyl}amino)-6-methylquinazolin-2-carboxamide dihydrochloride Elemental analysis value (as $C_{23}H_{34}N_6O_3$/2HCl/3.4H$_2$O)
Calculated (%) C, 47.90; H, 7.48; N, 14.57.
Found (%) C, 48.07; H, 7.13; N, 14.21.
Positive ion FAB-MS m/z: 443 [M+H]$^+$
Specific rotation $[\alpha]^{20}_D$=+94.54 (c=0.605 methanol)
Appearance: pale yellow powder

Example 62

4-{[(1S,2R)-2-(n-butanimidoylamino)cyclohexyl]amino}-N-(3-methoxypropyl)-6-methylquinazolin-2-carboxamide dihydrochloride Elemental analysis value (as $C_{24}H_{36}N_6O_2$/2HCl/3.4H$_2$O)
Calculated (%) C, 50.15; H, 7.86; N, 14.62.
Found (%) C, 50.17; H, 7.48; N, 14.60.
Positive ion FAB-MS m/z: 441 [M+H]$^+$
Specific rotation $[\alpha]^{20}_D$=+97.57 (c=0.660 methanol)
Appearance: pale yellow powder

Example 63

N-(3-methoxypropyl)-6-methyl-4-({(1S,2R)-2-[(2-methylpropanimidoyl)amino]cyclohexyl}amino)quinazolin-2-carboxamide dihydrochloride Positive ion FAB-MS m/z: 441 [M+H]$^+$
Specific rotation $[\alpha]^{20}_D$=+61.88 (c=0.585 methanol)
Appearance: white powder

Example 64

4-({(1R,2S)-2-[(3-hydroxypropanimidoyl)amino]cyclohexyl}amino)-N-isopropyl-6-methylquinazolin-2-carboxamide dihydrochloride Positive ion FAB-MS m/z: 413 [M+H]$^+$
Specific rotation $[\alpha]^{20}_D$=−113.42 (c=0.760 methanol)
Appearance: pale yellow powder

Example 65

4-({(1S,2R)-2-[(2-hydroxy-2-methylpropanimidoyl)amino]cyclohexyl}amino)-N-isopropyl-6-methylquinazolin-2-carboxamide dihydrochloride Positive ion FAB-MS m/z: 427 [M+H]$^+$
Specific rotation $[\alpha]^{20}_D$=+13.23 (c=0.665 methanol)
Appearance: pale yellow powder

Example 66

4-({(1S,2R)-2-[(2-hydroxy-2-methylpropanimidoyl)amino]cyclohexyl}amino)-N-(3-methoxypropyl)-6-methylquinazolin-2-carboxamide dihydrochloride Positive ion FAB-MS m/z: 457 [M+H]$^+$
Specific rotation $[\alpha]^{20}_D$=+21.65 (c=0.665 methanol)
Appearance: pale yellow powder

Example 67

4-({(1S,2R)-2-[(2-hydroxy-2-methylpropanimidoyl)amino]cyclohexyl}amino)-N-(2-methoxyethyl)-6-methylquinazolin-2-carb oxamide dihydrochloride Elemental analysis value (as $C_{23}H_{34}N_6O_3$/2HCl/H$_2$O)
Calculated (%) C, 51.78; H, 7.18; N, 15.75.
Found (%) C, 51.79; H, 6.86; N, 15.83.
Positive ion FAB-MS m/z: 443 [M+H]$^+$
Specific rotation $[\alpha]^{20}_D$=+4.44 (c=0.495 methanol)
Appearance: white powder

Example 68

6-chloro-N-cycloheptyl-4-{[(1S,2R)-2-(ethanimidoylamino)cyclohexyl]amino}quinazolin-2-carboxamide dihydrochloride Elemental analysis value (as $C_{24}H_{33}ClN_6O$/2HCl/2H$_2$O)
Calculated (%) C, 50.93; H, 6.95; N, 14.85.
Found (%) C, 50.58; H, 6.86; N, 14.48.
Positive ion FAB-MS m/z: 457 [M+H]$^+$
Specific rotation $[\alpha]^{20}_D$=+99.35 (c=0.465 methanol)
Appearance: white powder

Example 69

6-chloro-N-cycloheptyl-4-[((1S,2R)-2-{[N-hydroxyethanimidoyl]amino}cyclohexyl)amino]quinazolin-2-carboxamide dihydrochloride Elemental analysis value (as $C_{24}H_{33}N_6O_2Cl$/2HCl/1.5H$_2$O)
Calculated (%) C, 50.31; H, 6.68; N, 14.67.
Found (%) C, 50.71; H, 6.85; N, 14.49.
Positive ion FAB-MS m/z: 473 [M+H]$^+$
Specific rotation $[\alpha]^{20}_D$=+3.99 (c=0.501 methanol)
Appearance: white powder

Example 70

N-isobutyl-4-({(1S,2R)-2-[(2-methoxyethanimidoyl)amino]cyclohexyl}amino)-6-methylquinazolin-2-carboxamide dihydrochloride Elemental analysis value (as $C_{23}H_{34}N_6O_2$/2HCl/2.5H$_2$O)
Calculated (%) C, 50.73; H, 7.59; N, 15.43.
Found (%) C, 50.81; H, 7.54; N, 15.59.
Positive ion FAB-MS m/z: 427 [M+H]$^+$
Specific rotation $[\alpha]^{20}_D$=+106.99 (c=0.529 methanol)
Appearance: white powder

Example 71

6-chloro-4-({(1S,2R)-2-[(2-methoxyethanimidoyl)amino]cyclohexyl}amino) quinazolin-2-carboxamide dihydrochloride Elemental analysis value (as $C_{18}H_{23}N_6O_2Cl/2HCl/3H_2O$)
Calculated (%) C, 41.75; H, 6.03; N, 16.23.
Found (%) C, 41.85; H, 5.84; N, 16.22.
Positive ion FAB-MS m/z: 391 [M+H]$^+$
Specific rotation $[\alpha]^{20}_D$=+154.05 (c=0.518 methanol)
Appearance: white powder

Example 72

6-chloro-N-methoxy-4-({(1S,2R)-2-[(2-methoxyethanimidoyl)amino]cyclohexyl}amino)quinazolin-2-carboxamide dihydrochloride Elemental analysis value (as $C_{19}H_{25}N_6O_3Cl/2HCl/2.5H_2O$)
Calculated (%) C, 42.35; H, 5.99; N, 15.60.
Found (%) C, 42.46; H, 6.41; N, 15.36.
Positive ion FAB-MS m/z: 421 [M+H]$^+$
Specific rotation $[\alpha]^{20}_D$=+21.20 (c=0.547 methanol)
Appearance: white powder

Example 73

N-n-butyl-6-chloro-4-({(1S,2R)-2-[(2-methoxyethanimidoyl)amino]cyclohexyl}amino)quinazolin-2-carboxamide dihydrochloride Elemental analysis value (as $C_{22}H_{31}N_6O_2Cl/2HCl/1.5H_2O$)
Calculated (%) C, 48.31; H, 6.63; N, 15.37.
Found (%) C, 48.56; H, 6.49; N, 15.41.
Positive ion FAB-MS m/z: 447 [M+H]$^+$
Specific rotation $[\alpha]^{20}_D$=+111.52 (c=0.538 methanol)
Appearance: white powder

Example 74

N-(2,2-dimethylpropyl)-4-{[(1S,2R)-2-(ethanimidoylamino)cyclohexyl]amino}-6-methylquinazolin-2-carboxamide dihydrochloride Elemental analysis value (as $C_{23}H_{34}N_6O/2HCl/1.6H_2O$)
Calculated (%) C, 53.92; H, 7.71; N, 16.40.
Found (%) C, 54.31; H, 7.55; N, 15.98.
Positive ion FAB-MS m/z: 411 [M+H]$^+$
Specific rotation $[\alpha]^{20}_D$=+88.65 (c=0.467 methanol)
Appearance: white powder

Example 75

4-{[(1S,2R)-2-(ethanimidoylamino)cyclohexyl]amino}-N-isobutyl-6-methylquinazolin-2-carboxamide dihydrochloride Elemental analysis value (as $C_{22}H_{32}N_6O/2HCl/0.8H_2O$)
Calculated (%) C, 54.61; H, 7.42; N, 17.37.
Found (%) C, 54.85; H, 7.39; N, 17.00.
Positive ion FAB-MS m/z: 397 [M+H]$^+$
Specific rotation $[\alpha]^{20}_D$=+91.96 (c=0.523 methanol)
Appearance: pale brown powder

Example 76

4-{[(1S,2R)-2-(ethanimidoylamino)cyclohexyl]amino}-6-methyl-N-(2,2,2-trifluoroethyl)quinazolin-2-carboxamide dihydrochloride Elemental analysis value (as $C_{20}H_{25}N_6OF_3/2HCl/0.5H_2O$)
Calculated (%) C, 47.63; H, 5.60; N, 16.66.
Found (%) C, 47.76; H, 5.74; N, 16.56.
Positive ion FAB-MS m/z: 423 [M+H]$^+$
Specific rotation $[\alpha]^{20}_D$=+96.59 (c=0.528 methanol)
Appearance: white powder

Example 77

N-(cyclopentylmethyl)-4-({(1S,2R)-2-[(2-methoxyethanimidoyl)amino]cyclohexyl}amino)-6-methylquinazolin-2-carboxamide dihydrochloride Elemental analysis value (as $C_{25}H_{36}N_6O_2/2HCl/0.7H_2O$)
Calculated (%) C, 55.61; H, 7.39; N, 15.56.
Found (%) C, 55.72; H, 7.17; N, 15.58.
Positive ion FAB-MS m/z: 453 [M+H]$^+$
Specific rotation $[\alpha]^{20}_D$=+101.58 (c=0.443 methanol)
Appearance: white powder

Example 78

N-(cyclopentyl)-4-({(1S,2R)-2-[(2-methoxyethanimidoyl)amino]cyclohexyl}amino)-6-methylquinazolin-2-carboxamide dihydrochloride Elemental analysis value (as $C_{24}H_{34}N_6O_3/2HCl/0.7H_2O$)
Calculated (%) C, 55.00; H, 7.19; N, 16.04.
Found (%) C, 55.14; H, 7.22; N, 15.78.
Positive ion FAB-MS m/z: 439 [M+H]$^+$
Specific rotation $[\alpha]^{20}_D$=+110.19 (c=0.559 methanol)
Appearance: white powder

Example 79

N-(1,1-dimethylpropyl)-4-({(1S,2R)-2-[(2-methoxyethanimidoyl)amino]cyclohexyl}amino)-6-methylquinazolin-2-carboxamide dihydrochloride Positive ion FAB-MS m/z: 441 [M+H]$^+$
Specific rotation $[\alpha]^{20}_D$=+96.57 (c=0.497 methanol)
Appearance: white powder

Example 80

N-(2,2-dimethylpropyl)-4-{[(1S,2R)-2-(2-ethanimidoylamino)cyclohexyl]amino}-6-fluoroquinazolin-2-carboxamide dihydrochloride Elemental analysis value (as $C_{22}H_{31}N_6OF/2HCl/0.8H_2O$)
Calculated (%) C, 52.65; H, 6.95; N, 16.75.
Found (%) C, 52.85; H, 7.13; N, 16.53.
Positive ion FAB-MS m/z: 415 [M+H]$^+$
Specific rotation $[\alpha]^{20}_D$=+47.88 (c=0.497 methanol)
Appearance: white powder

Example 81

4-{[(1S,2R)-2-(2-ethanimidoylamino)cyclohexyl]amino}-6-fluoro-N-(3-methoxy-2,2-dimethylpropyl)quinazolin-2-carboxamide dihydrochloride Positive ion FAB-MS m/z: 445 [M+H]$^+$
Specific rotation $[\alpha]^{20}_D$=+43.24 (c=0.481 methanol)
Appearance: white powder

Example 82

4-{[(1S,2R)-2-(ethanimidoylamino)cyclohexyl]amino}-N-(2-isopropoxyethyl)-6-methylquinazolin-2-carboxamide dihydrochloride Elemental analysis value (as $C_{23}H_{34}N_6O_2$/2HCl/1.6H$_2$O)
Calculated (%) C, 52.29; H, 7.48; N, 15.91.
Found (%) C, 52.07; H, 7.36; N, 15.89.
Positive ion FAB-MS m/z: 427 [M+H]$^+$
Specific rotation $[\alpha]^{20}_D$=+92.65 (c=0.490 methanol)
Appearance: white powder

Example 83

4-[((1S,2R)-2-{[N-hydroxyethanimidoyl]amino}cyclohexyl)amino]-N-isobutyl-6-methylquinazolin-2-carboxamide dihydrochloride Elemental analysis value (as $C_{22}H_{32}N_6O_2$/2HCl/H$_2$O)
Calculated (%) C, 52.48; H, 7.21; N, 16.69.
Found (%) C, 52.71; H, 7.31; N, 16.64.
Positive ion FAB-MS m/z: 413 [M+H]$^+$
Specific rotation $[\alpha]^{20}_D$=+3.23 (c=0.556 methanol)
Appearance: white powder

Example 84

N-(2-isopropoxyethyl)-4-({(1S,2R)-2-[(2-methoxy-2-methylpropanimidoyl)amino]cyclohexyl}amino)-6-methylquinazolin-2-carboxamide dihydrochloride Elemental analysis value (as $C_{26}H_{40}N_6O_3$/2HCl/H$_2$O)
Calculated (%) C, 54.26; H, 7.71; N, 14.60.
Found (%) C, 54.48; H, 7.61; N, 14.71.
Positive ion FAB-MS m/z: 485 [M+H]$^+$
Specific rotation $[\alpha]^{20}_D$=+10.88 (c=0.551 methanol)
Appearance: white powder

Example 85

N-(2-isopropoxyethyl)-4-({(1S,2R)-2-[(2-methoxyethanimidoyl)amino]cyclohexyl}amino)-6-methylquinazolin-2-carboxamide dihydrochloride Elemental analysis value (as $C_{24}H_{36}N_6O_3$/2HCl/1.5H$_2$O)
Calculated (%) C, 53.00; H, 7.34; N, 15.45.
Found (%) C, 53.05; H, 7.50; N, 15.37.
Positive ion FAB-MS m/z: 457 [M+H]$^+$
Specific rotation $[\alpha]^{20}_D$=+119.91 (c=0.487 methanol)
Appearance: white powder

Example 86

4-{[(1S,2R)-2-(ethanimidoylamino)cyclohexyl]amino}-N-(3-isopropoxypropyl)-6-methylquinazolin-2-carboxamide dihydrochloride Elemental analysis value (as $C_{24}H_{36}N_6O_2$/2HCl/1.5H$_2$O)
Calculated (%) C, 53.33; H, 7.65; N, 15.55.
Found (%) C, 53.46; H, 7.49; N, 15.50.
Positive ion FAB-MS m/z: 441 [M+H]$^+$
Specific rotation $[\alpha]^{20}_D$=+91.49 (c=0.529 methanol)
Appearance: white powder

Example 87

N-(3-isopropoxypropyl)-4-({(1S,2R)-2-[(2-methoxyethanimidoyl)amino]cyclohexyl}amino)-6-methylquinazolin-2-carboxamide dihydrochloride Elemental analysis value (as $C_{25}H_{38}N_6O_3$/2HCl/2H$_2$O)
Calculated (%) C, 51.81; H, 7.65; N, 14.50.
Found (%) C, 51.47; H, 7.30; N, 14.65.
Positive ion FAB-MS m/z: 471 [M+H]$^+$
Specific rotation $[\alpha]^{20}_D$=+100.40 (c=0.500 methanol)
Appearance: white powder

Example 88

4-{[(1S,2R)-2-(ethanimidoylamino)cyclohexyl]amino}-N-methoxy-6-methylquinazolin-2-carboxamide dihydrochloride Positive ion FAB-MS m/z: 371 [M+H]$^+$
Specific rotation $[\alpha]^{20}_D$=+116.79 (c=0.500 methanol)
Appearance: white powder

Example 89

N-methoxy-4-({(1S,2R)-2-[(2-methoxyethanimidoyl)amino]cyclohexyl}amino)-6-methylquinazolin-2-carboxamide dihydrochloride Positive ion FAB-MS m/z: 401 [M+H]$^+$
Specific rotation $[\alpha]^{20}_D$=+105.19 (c=0.500 methanol)
Appearance: white powder

Example 90

6-chloro-N-cycloheptyl-4-({(1S,2R)-2-[(2-methoxyethanimidoyl)amino]cyclohexyl}amino)quinazolin-2-carboxamide dihydrochloride Elemental analysis value (as $C_{25}H_{35}N_6O_2Cl$/2HCl/1.4H$_2$O)
Calculated (%) C, 51.31; H, 6.86; N, 14.36.
Found (%) C, 51.30; H, 6.71; N, 14.20.
Positive ion FAB-MS m/z: 487 [M+H]$^+$
Specific rotation $[\alpha]^{20}_D$=+107.38 (c=0.501 methanol)
Appearance: white powder

Example 91

4-({(1S,2R)-2-[(2-methoxyethanimidoyl)amino]cyclohexyl}amino)-N-(2-methoxyethyl)-6-methylquinazolin-2-carboxamide dihydrochloride Positive ion FAB-MS m/z: 429 [M+H]$^+$
Specific rotation $[\alpha]^{20}_D$=+114.85 (c=0.505 methanol)
Appearance: white powder

Example 92

4-{[(1S,2R)-2-(ethanimidoylamino)cyclohexyl]amino}-N-(3-methoxypropyl)-6-methylquinazolin-2-carboxamide dihydrochloride Positive ion FAB-MS m/z: 413 [M+H]$^+$
Specific rotation $[\alpha]^{20}_D$=+96.40 (c=0.500 methanol)
Appearance: white powder

Example 93

4-({(1S,2R)-2-[(2-methoxyethanimidoyl)amino]cyclohexyl}amino)-N-(3-methoxypropyl)-6-methylquinazolin-2-carboxamide dihydrochloride Elemental analysis value (as $C_{23}H_{34}N_6O_3/2HCl/2.5H_2O$)
Calculated (%) C, 49.29; H, 7.37; N, 14.99.
Found (%) C, 49.15; H, 7.37; N, 14.93.
Positive ion FAB-MS m/z: 443 [M+H]$^+$
Specific rotation $[\alpha]^{20}_D$=+107.57 (c=0.515 methanol)
Appearance: white powder

Example 94

4-{[(1S,2R)-2-(ethanimidoylamino)cyclohexyl]amino}-N-(2-ethoxyethyl)-6-methylquinazolin-2-carboxamide dihydrochloride Elemental analysis value (as $C_{22}H_{32}N_6O_2/2HCl/2.6H_2O$)
Calculated (%) C, 49.64; H, 7.42; N, 15.79.
Found (%) C, 49.27; H, 7.03; N, 15.60.
Positive ion FAB-MS m/z: 413 [M+H]$^+$
Specific rotation $[\alpha]^{20}_D$=+105.74 (c=0.505 methanol)
Appearance: white powder

Example 95

N-(2-ethoxyethyl)-4-({(1S,2R)-2-[(2-methoxyethanimidoyl)amino]cyclohexyl}amino)-6-methylquinazolin-2-carboxamide dihydrochloride Elemental analysis value (as $C_{23}H_{34}N_6O_3/2HCl/1.3H_2O$)
Calculated (%) C, 51.26; H, 7.22; N, 15.59.
Found (%) C, 51.20; H, 7.06; N, 15.55.
Positive ion FAB-MS m/z: 443 [M+H]$^+$
Specific rotation $[\alpha]^{20}_D$=+101.38 (c=0.505 methanol)
Appearance: white powder

Example 96

4-{[(1S,2R)-2-(ethanimidoylamino)cyclohexyl]amino}-N-(3-methoxy-2,2-dimethylpropyl)-6-methylquinazolin-2-carboxamide dihydrochloride Elemental analysis value (as $C_{24}H_{36}N_6O_2/2HCl/1.9H_2O$)
Calculated (%) C, 52.63; H, 7.69; N, 15.34.
Found (%) C, 52.46; H, 7.39; N, 14.98.
Positive ion FAB-MS m/z: 441 [M+H]$^+$
Specific rotation $[\alpha]^{20}_D$=+83.07 (c=0.520 methanol)
Appearance: white powder

Example 97

N-(3-methoxy-2,2-dimethylpropyl)-4-({(1S,2R)-2-[(2-methoxy ethanimidoyl)amino]cyclohexyl}amino)-6-methylquinazolin-2-carboxamide dihydrochloride Elemental analysis value (as $C_{25}H_{38}N_6O_3/2HCl/2.5H_2O$)
Calculated (%) C, 51.02; H, 7.71; N, 14.28.
Found (%) C, 50.84; H, 7.32; N, 14.18.
Positive ion FAB-MS m/z: 471 [M+H]$^+$
Specific rotation $[\alpha]^{20}_D$=+95.68 (c=0.510 methanol)
Appearance: white powder

Example 98

4-{[(1S,2R)-2-(ethanimidoylamino)cyclohexyl]amino}-N-(2-furylmethyl)-6-methylquinazolin-2-carboxamide dihydrochloride Elemental analysis value (as $C_{23}H_{28}N_6O_2/2HCl/3H_2O$)
Calculated (%) C, 50.46; H, 6.63; N, 15.35.
Found (%) C, 50.61; H, 6.24; N, 15.36.
Positive ion FAB-MS m/z: 421 [M+H]$^+$
Specific rotation $[\alpha]^{20}_D$=+100.00 (c=0.510 methanol)
Appearance: white powder

Example 99

4-{[(1S,2R)-2-(ethanimidoylamino)cyclohexyl]amino}-N-(trans-4-hydroxycyclohexyl)-6-methylquinazolin-2-carboxamide dihydrochloride Elemental analysis value (as $C_{24}H_{34}N_6O_2/2HCl/3.6H_2O$)
Calculated (%) C, 50.02; H, 7.55; N, 14.58.
Found (%) C, 50.35; H, 7.22; N, 14.21.
Positive ion FAB-MS m/z: 439 [M+H]$^+$
Specific rotation $[\alpha]^{20}_D$=+70.58 (c=0.510 methanol)
Appearance: white powder

Example 100

N-(trans-4-hydroxycyclohexyl)-4-({(1S,2R)-2-[(2-methoxyethanimidoyl)amino]cyclohexyl}amino)-6-methylquinazolin-2-carboxamide dihydrochloride Positive ion FAB-MS m/z: 469 [M+H]$^+$
Specific rotation $[\alpha]^{20}_D$=+103.59 (c=0.500 methanol)
Appearance: white powder

Example 101

4-{[(1S,2R)-2-(ethanimidoylamino)cyclohexyl]amino}-N-isopropyl-6-methylquinazolin-2-carboxamide dihydrochloride Positive ion FAB-MS m/z: 383 [M+H]$^+$
Specific rotation $[\alpha]^{20}_D$=+107.32 (c=0.505 methanol)
Appearance: white powder

Example 102

N-isopropyl-4-({(1S,2R)-2-[(2-methoxyethanimidoyl)amino]cyclohexyl}amino)-6-methylquinazolin-2-carboxamide dihydrochloride Elemental analysis value (as $C_{22}H_{32}N_6O_2/2HCl/2H_2O$)
Calculated (%) C, 50.67; H, 7.34; N, 16.12.
Found (%) C, 50.94; H, 7.15; N, 16.38.
Positive ion FAB-MS m/z: 413 [M+H]$^+$
Specific rotation $[\alpha]^{20}_D$=+127.05 (c=0.510 methanol)
Appearance: white powder

Example 103

4-{[(1S,2R)-2-(ethanimidoylamino)cyclohexyl]amino}-N-(2-fluoroethyl)-6-methylquinazolin-2-carboxamide dihydrochloride Elemental analysis value (as $C_{20}H_{27}N_6OF/2HCl/2.5H_2O$)
Calculated (%) C, 47.62; H, 6.79; N, 16.66.

Found (%) C, 47.59; H, 6.56; N, 16.44.
Positive ion FAB-MS m/z: 387 [M+H]$^+$
Specific rotation $[\alpha]^{20}_D$=+114.79 (c=0.500 methanol)
Appearance: pale brown powder

Example 104

4-{[(1S,2R)-2-(3,4-dihydro-2H-pyrrol-5-ylamino)cyclohexyl]amino}-N-(3-methoxypropyl)-6-methylquinazolin-2-carboxamide dihydrochloride Elemental analysis value (as $C_{24}H_{34}N_6O_2$/2HCl/1.1H$_2$O)
Calculated (%) C, 54.26; H, 7.25; N, 15.82.
Found (%) C, 54.27; H, 7.57; N, 15.58.
Positive ion FAB-MS m/z: 439 [M+H]$^+$
Specific rotation $[\alpha]^{20}_D$=+83.61 (c=0.476 methanol)
Appearance: white powder

Example 105

4-{[(1S,2R)-2-(3,4-dihydro-2H-pyrrol-5-ylamino)cyclohexyl]amino}-N-(2-methoxyethyl)-6-methylquinazolin-2-carboxamide dihydrochloride Positive ion FAB-MS m/z: 425 [M+H]$^+$
Specific rotation $[\alpha]^{20}_D$=+79.21 (c=0.510 methanol)
Appearance: white powder

Example 106

N-(cyclopropylmethyl)-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{24}H_{32}N_6O$/2HCl/1.4H$_2$O)
Calculated (%) C, 55.57; H, 7.15; N, 16.20.
Found (%) C, 55.53; H, 7.00; N, 16.13.
Positive ion FAB-MS m/z: 421 [M+H]$^+$
Specific rotation $[\alpha]^{20}_D$=+90.67 (c=0.536 methanol)
Appearance: white powder

Example 107

4-{[(1S,2R)-2-(3,4-dihydro-2H-pyrrol-5-ylamino)cyclohexyl]amino}-N-(2-ethylbutyl)-6-methylquinazolin-2-carboxamide dihydrochloride Elemental analysis value (as $C_{26}H_{38}N_6O$/2HCl/0.9H$_2$O)
Calculated (%) C, 57.86; H, 7.81; N, 15.57.
Found (%) C, 57.81; H, 7.90; N, 15.34.
Positive ion FAB-MS m/z: 451 [M+H]$^+$
Specific rotation $[\alpha]^{20}_D$=+81.48 (c=0.540 methanol)
Appearance: white powder

Example 108

N-(cyclohexylmethyl)-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{27}H_{38}N_6O$/2HCl/1.4H$_2$O)
Calculated (%) C, 57.83; H, 7.69; N, 14.99.
Found (%) C, 58.09; H, 7.74; N, 14.70.
Positive ion FAB-MS m/z: 463 [M+H]$^+$
Specific rotation $[\alpha]^{20}_D$=+78.36 (c=0.513 methanol)
Appearance: white powder

Example 109

4-{[(1S,2R)-2-(3,4-dihydro-2H-pyrrol-5-ylamino)cyclohexyl]amino}-N-(2,2-dimethylpropyl)-6-methylquinazolin-2-carboxamide dihydrochloride Elemental analysis value (as $C_{25}H_{36}N_6O$/2HCl/1.8H$_2$O)
Calculated (%) C, 55.41; H, 7.74; N, 15.51.
Found (%) C, 55.41; H, 7.78; N, 15.51.
Positive ion FAB-MS m/z: 437 [M+H]$^+$
Specific rotation $[\alpha]^{20}_D$=+75.72 (c=0.486 methanol)
Appearance: white powder

Example 110

4-{[(1S,2R)-2-(3,4-dihydro-2H-pyrrol-5-ylamino)cyclohexyl]amino}-N-[(1R,2R)-2-methoxycyclohexyl]-6-methylquinazolin-2-carboxamide dihydrochloride Elemental analysis value (as $C_{27}H_{38}N_6O_2$/2HCl/2.1H$_2$O)
Calculated (%) C, 55.02; H, 7.56; N, 14.26.
Found (%) C, 55.08; H, 7.48; N, 14.23.
Positive ion FAB-MS m/z: 479 [M+H]$^+$
Specific rotation $[\alpha]^{20}_D$=+61.50 (c=0.517 methanol)
Appearance: white powder

Example 111

4-{[(1S,2R)-2-(3,4-dihydro-2H-pyrrol-5-ylamino)cyclohexyl]amino}-N-ethyl-6-methylquinazolin-2-carboxamide dihydrochloride Elemental analysis value (as $C_{22}H_{30}N_6O$/2HCl/2H$_2$O)
Calculated (%) C, 50.32; H, 7.37; N, 16.00.
Found (%) C, 50.40; H, 7.14; N, 15.65.
Positive ion FAB-MS m/z: 395 [M+H]$^+$
Specific rotation $[\alpha]^{20}_D$=+95.73 (c=0.539 methanol)
Appearance: white powder

Example 112

4-{[(1S,2R)-2-(3,4-dihydro-2H-pyrrol-5-ylamino)cyclohexyl]amino}-N-[1-(methoxymethyl)cyclohexyl]-6-methylquinazolin-2-carboxamide dihydrochloride Elemental analysis value (as $C_{28}H_{40}N_6O_2$/2HCl/1.7H$_2$O)
Calculated (%) C, 56.41; H, 7.68; N, 14.10.
Found (%) C, 56.45; H, 7.65; N, 13.84.
Positive ion FAB-MS m/z: 493 [M+H]$^+$
Specific rotation $[\alpha]^{20}_D$=+57.51 (c=0.532 methanol)
Appearance: white powder

Example 113

4-{[(1S,2R)-2-(3,4-dihydro-2H-pyrrol-5-ylamino)cyclohexyl]amino}-N-(2-ethylbutyl)-6-methoxyquinazolin-2-carboxamide dihydrochloride Elemental analysis value (as $C_{26}H_{38}N_6O_2$/2HCl/1.6H$_2$O)
Calculated (%) C, 54.94; H, 7.66; N, 14.79.
Found (%) C, 55.02; H, 7.30; N, 14.58.
Positive ion FAB-MS m/z: 467 [M+H]$^+$
Specific rotation $[\alpha]^{20}_D$=+114.98 (c=0.534 methanol)
Appearance: white powder

Example 114

4-{[(1S,2R)-2-(3,4-dihydro-2H-pyrrol-5-ylamino)cyclohexyl]amino}-N-[(1R)-1-(methoxymethyl)-2-methylpropyl]-6-methylquinazolin-2-carboxamide dihydrochloride Elemental analysis value (as $C_{26}H_{38}N_6O_2/2HCl/2.3H_2O$)
Calculated (%) C, 53.75; H, 7.74; N, 14.47.
Found (%) C, 53.65; H, 7.48; N, 14.52.
Positive ion FAB-MS m/z: 467 [M+H]$^+$
Specific rotation $[\alpha]^{20}_D$=+75.61 (c=0.529 methanol)
Appearance: white powder

Example 115

4-{[(1S,2R)-2-(3,4-dihydro-2H-pyrrol-5-ylamino)cyclohexyl]amino}-N-(2-ethylpropyl)-6-methylquinazolin-2-carboxamide dihydrochloride Elemental analysis value (as $C_{25}H_{36}N_6O/2HCl/1.2H_2O$)
Calculated (%) C, 56.53; H, 7.67; N, 15.82.
Found (%) C, 56.55; H, 7.62; N, 15.55.
Positive ion FAB-MS m/z: 437 [M+H]$^+$
Specific rotation $[\alpha]^{20}_D$=+91.09 (c=0.494 methanol)
Appearance: white powder

Example 116

4-{[(1S,2R)-2-(3,4-dihydro-2H-pyrrol-5-ylamino)cyclohexyl]amino}-N-(2,2-dimethylpropyl)-6-fluoroquinazolin-2-carboxamide dihydrochloride Elemental analysis value (as $C_{24}H_{33}N_6OF/2HCl/H_2O$)
Calculated (%) C, 54.24; H, 7.02; N, 15.81.
Found (%) C, 54.47; H, 6.71; N, 15.56.
Positive ion FAB-MS m/z: 441 [M+H]$^+$
Specific rotation $[\alpha]^{20}_D$=+41.26 (c=0.504 methanol)
Appearance: white powder

Example 117

4-{[(1S,2R)-2-(3,4-dihydro-2H-pyrrol-5-ylamino)cyclohexyl]amino}-6-fluoro-N-isobutylquinazolin-2-carboxamide dihydrochloride Elemental analysis value (as $C_{23}H_{31}N_6OF/2HCl/1.3H_2O$)
Calculated (%) C, 52.83; H, 6.86; N, 16.07.
Found (%) C, 52.88; H, 6.76; N, 15.74.
Positive ion FAB-MS m/z: 427 [M+H]$^+$
Specific rotation $[\alpha]^{20}_D$=+48.82 (c=0.512 methanol)
Appearance: white powder

Example 118

4-{[(1S,2R)-2-(3,4-dihydro-2H-pyrrol-5-ylamino)cyclohexyl]amino}-6-fluoro-N-(3-methoxy-2,2-dimethylpropyl)quinazolin-2-carboxamide dihydrochloride Elemental analysis value (as $C_{25}H_{35}N_6O_2F/2HCl/H_2O$)
Calculated (%) C, 53.48; H, 7.00; N, 14.97.
Found (%) C, 53.59; H, 6.98; N, 14.69.
Positive ion FAB-MS m/z: 471 [M+H]$^+$
Specific rotation $[\alpha]^{20}_D$=+33.88 (c=0.543 methanol)
Appearance: white powder

Example 119

4-{[(1S,2R)-2-(3,4-dihydro-2H-pyrrol-5-ylamino)cyclohexyl]amino}-N-[2-methoxy-1-(methoxymethyl)-1-methylethyl]-6-methylquinazolin-2-carboxamide dihydrochloride Elemental analysis value (as $C_{26}H_{38}N_6O_3/2HCl/1.9H_2O$)
Calculated (%) C, 52.95; H, 7.49; N, 14.25.
Found (%) C, 52.91; H, 7.36; N, 14.02.
Positive ion FAB-MS m/z: 483 [M+H]$^+$
Specific rotation $[\alpha]^{20}_D$=+69.64 (c=0.560 methanol)
Appearance: white powder

Example 120

4-{[(1S,2R)-2-(3,4-dihydro-2H-pyrrol-5-ylamino)cyclohexyl]amino}-N-(4-methoxyphenyl)-6-methylquinazolin-2-carboxamide dihydrochloride Elemental analysis value (as $C_{27}H_{32}N_6O_2/2HCl/2.7H_2O$)
Calculated (%) C, 54.58; H, 6.68; N, 14.14.
Found (%) C, 54.47; H, 7.02; N, 14.25.
Positive ion FAB-MS m/z: 473 [M+H]$^+$
Specific rotation $[\alpha]^{20}_D$=+34.84 (c=0.683 methanol)
Appearance: yellow powder

Example 121

N-n-butyl-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{24}H_{34}N_6O/2HCl/2H_2O$)
Calculated (%) C, 54.23; H, 7.59; N, 15.81.
Found (%) C, 54.36; H, 7.36; N, 15.62.
Positive ion FAB-MS m/z: 423 [M+H]$^+$
Specific rotation $[\alpha]^{20}_D$=+86.93 (c=0.773 methanol)
Appearance: white powder

Example 122

N-n-butyl-6-methyl-4-{[(1S,2R)-2-(3,4,5,6-tetrahydropyridin-2-ylamino)cyclohexyl]amino}quinazolin-2-carboxamide dihydrochloride Elemental analysis value (as $C_{25}H_{36}N_6O/2HCl/0.9H_2O$)
Calculated (%) C, 57.12; H, 7.63; N, 15.99.
Found (%) C, 57.25; H, 7.64; N, 15.79.
Positive ion FAB-MS m/z: 437 [M+H]$^+$
Specific rotation $[\alpha]^{20}_D$=+100.57 (c=0.696 methanol)
Appearance: white powder

Example 123

N-n-butyl-6-methyl-4-{[(1S,2R)-2-(3,4,5,6-tetrahydro-2H-azepin-7-ylamino)cyclohexyl]amino}quinazolin-2-carboxamide dihydrochloride Elemental analysis value (as $C_{26}H_{38}N_6O/2HCl/1.6H_2O$)
Calculated (%) C, 56.54; H, 7.88; N, 15.21.
Found (%) C, 56.53; H, 7.60; N, 15.28.
Positive ion FAB-MS m/z: 451 [M+H]$^+$
Specific rotation $[\alpha]^{20}_D$=+85.02 (c=0.741 methanol)
Appearance: white powder

Example 124

6-chloro-N-cycloheptyl-4-{[(1S,2R)-2-(3,4-dihydro-2H-pyrrol-5-ylamino)cyclohexyl]amino}quinazolin-2-carboxamide dihydrochloride Elemental analysis value (as $C_{26}H_{35}ClN_6O/2HCl/2H_2O$)
Calculated (%) C, 52.75; H, 6.98; N, 14.20.
Found (%) C, 52.97; H, 6.86; N, 14.37.
Positive ion FAB-MS m/z: 483 [M+H]$^+$
Specific rotation $[\alpha]^{20}_D$=+67.28 (c=0.535 methanol)
Appearance: white powder

Example 125

N-n-butyl-6-chloro-4-{[(1S,2R)-2-(3,4-dihydro-2H-pyrrol-5-ylamino)cyclohexyl]amino}quinazolin-2-carboxamide dihydrochloride Elemental analysis value (as $C_{23}H_{31}ClN_6O/2HCl/H_2O$)
Calculated (%) C, 51.84; H, 6.61; N, 15.74.
Found (%) C, 51.82; H, 6.74; N, 15.71.
Positive ion FAB-MS m/z: 443 [M+H]$^+$
Specific rotation $[\alpha]^{20}_D$=+88.64 (c=0.546 methanol)
Appearance: white powder

Example 126

N-cycloheptyl-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{27}H_{38}N_6O/2HCl/1.5H_2O$)
Calculated (%) C, 57.64; H, 7.70; N, 14.94.
Found (%) C, 57.52; H, 7.78; N, 14.90.
Positive ion FAB-MS m/z: 463 [M+H]$^+$
Specific rotation $[\alpha]^{20}_D$=+67.56 (c=0.447 methanol)
Appearance: white powder

Example 127

6-chloro-4-{[(1S,2R)-2-(3,4-dihydro-2H-pyrrol-5-ylamino)cyclohexyl]amino}quinazolin-2-carboxamide dihydrochloride Elemental analysis value (as $C_{19}H_{23}ClN_6O/2HCl/1.3H_2O$)
Calculated (%) C, 47.23; H, 5.76; N, 17.39.
Found (%) C, 47.21; H, 5.99; N, 17.20.
Positive ion FAB-MS m/z: 387 [M+H]$^+$
Specific rotation $[\alpha]^{20}_D$=+104.23 (c=0.520 methanol)
Appearance: white powder

Example 128

6-chloro-4-{[(1S,2R)-2-(3,4-dihydro-2H-pyrrol-5-ylamino)cyclohexyl]amino}-N-methoxyquinazolin-2-carboxamide dihydrochloride Elemental analysis value (as $C_{20}H_{25}ClN_6O_2/2HCl/1.3H_2O$)
Calculated (%) C, 46.80; H, 5.81; N, 16.37.
Found (%) C, 46.87; H, 5.55; N, 16.30.
Positive ion FAB-MS m/z: 417 [M+H]$^+$
Specific rotation $[\alpha]^{20}_D$=+53.81 (c=0.524 methanol)
Appearance: white powder

Example 129

4-{[(1S,2R)-2-(3,4-dihydro-2H-pyrrol-5-ylamino)cyclohexyl]amino}-N-(3-methoxy-2,2-dimethylpropyl)-6-methylquinazolin-2-carboxamide dihydrochloride Elemental analysis value (as $C_{26}H_{38}N_6O_2/2HCl/H_2O$)
Calculated (%) C, 56.01; H, 7.59; N, 15.07.
Found (%) C, 55.96; H, 7.85; N, 14.85.
Positive ion FAB-MS m/z: 467 [M+H]$^+$
Specific rotation $[\alpha]^{20}_D$=+71.08 (c=0.543 methanol)
Appearance: white powder

Example 130

4-{[(1S,2R)-2-(3,4-dihydro-2H-pyrrol-5-ylamino)cyclohexyl]amino}-N-isobutyl-6-methylquinazolin-2-carboxamide dihydrochloride Elemental analysis value (as $C_{24}H_{34}N_6O/2HCl/1.2H_2O$)
Calculated (%) C, 55.94; H, 7.47; N, 16.31.
Found (%) C, 55.89; H, 7.64; N, 16.24.
Positive ion FAB-MS m/z: 423 [M+H]$^+$
Specific rotation $[\alpha]^{20}_D$=+93.53 (c=0.464 methanol)
Appearance: white powder

Example 131

4-{[(1S,2R)-2-(3,4-dihydro-2H-pyrrol-5-ylamino)cyclohexyl]amino}-N-(2-isopropoxyethyl)-6-methylquinazolin-2-carboxamide dihydrochloride Elemental analysis value (as $C_{25}H_{36}N_6O_2/2HCl/1.6H_2O$)
Calculated (%) C, 54.17; H, 7.49; N, 15.16.
Found (%) C, 54.27; H, 7.39; N, 15.21.
Positive ion FAB-MS m/z: 453 [M+H]$^+$
Specific rotation $[\alpha]^{20}_D$=+95.25 (c=0.527 methanol)
Appearance: white powder

Example 132

4-{[(1S,2R)-2-(3,4-dihydro-2H-pyrrol-5-ylamino)cyclohexyl]amino}-6-methyl-N-[2-(methylthio)ethyl]quinazolin-2-carboxamide dihydrochloride Elemental analysis value (as $C_{23}H_{32}N_6OS/2HCl/1.3H_2O$)
Calculated (%) C, 51.45; H, 6.87; N, 15.65.
Found (%) C, 51.52; H, 6.96; N, 15.47.
Positive ion FAB-MS m/z: 441 [M+H]$^+$
Specific rotation $[\alpha]^{20}_D$=+88.30 (c=0.530 methanol)
Appearance: white powder

Example 133

4-{[(1S,2R)-2-(3,4-dihydro-2H-pyrrol-5-ylamino)cyclohexyl]amino}-N-(2-methoxy-1,1-dimethylethyl)-6-methylquinazolin-2-carboxamide dihydrochloride Positive ion FAB-MS m/z: 453 [M+H]$^+$
Specific rotation $[\alpha]^{20}_D$=+64.62 (c=0.489 methanol)
Appearance: white powder

Example 134

4-{[(1S,2R)-2-(3,4-dihydro-2H-pyrrol-5-ylamino)cyclohexyl]amino}-N-{[1-(methoxymethyl)cyclohexyl]methyl}-6-methylquinazolin-2-carboxamide dihydrochloride Elemental analysis value (as $C_{29}H_{42}N_6O_2/2HCl/1.4H_2O$)
Calculated (%) C, 57.59; H, 7.80; N, 13.89.
Found (%) C, 57.64; H, 7.79; N, 13.67.
Positive ion FAB-MS m/z: 507 [M+H]$^+$
Specific rotation $[\alpha]^{20}_D$=+54.23 (c=0.531 methanol)
Appearance: white powder

Example 135

4-{[(1S,2R)-2-(3,4-dihydro-2H-pyrrol-5-ylamino)cyclohexyl]amino}-6-methyl-N-(2-piperidin-1-yl-ethyl)quinazolin-2-carb oxamide trihydrochloride Elemental analysis value (as $C_{27}H_{39}N_7O/3HCl/2.1H_2O$)
Calculated (%) C, 51.90; H, 7.45; N, 15.69.
Found (%) C, 52.10; H, 7.77; N, 15.40.
Positive ion FAB-MS m/z: 478 [M+H]$^+$
Specific rotation $[\alpha]^{20}_D$=+111.91 (c=0.470 methanol)
Appearance: white powder

Example 136

N-cyclopentyl-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{25}H_{34}N_6O/2HCl/2.4H_2O$)
Calculated (%) C, 54.52; H, 7.47; N, 15.26.
Found (%) C, 54.64; H, 7.12; N, 15.07.
Positive ion FAB-MS m/z: 435 [M+H]$^+$
Specific rotation $[\alpha]^{20}_D$=+86.87 (c=0.541 methanol)
Appearance: white powder

Example 137

N-tert-butyl-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{24}H_{34}N_6O/2HCl/1.2H_2O$)
Calculated (%) C, 55.74; H, 7.48; N, 16.25.
Found (%) C, 55.81; H, 7.68; N, 16.00.
Positive ion FAB-MS m/z: 423 [M+H]$^+$
Specific rotation $[\alpha]^{20}_D$=+79.42 (c=0.491 methanol)
Appearance: white powder

Example 138

4-{[(1S,2R)-2-(3,4-dihydro-2H-pyrrol-5-ylamino)cyclohexyl]amino}-N-(trans-4-methoxycyclohexyl)-6-methylquinazolin-2-carboxamide dihydrochloride Elemental analysis value (as $C_{27}H_{38}N_6O_2/2HCl/1.5H_2O$)
Calculated (%) C, 56.05; H, 7.49; N, 14.53.
Found (%) C, 56.15; H, 7.56; N, 14.48.
Positive ion FAB-MS m/z: 479 [M+H]$^+$
Specific rotation $[\alpha]^{20}_D$=+77.12 (c=0.542 methanol)
Appearance: white powder

Example 139

4-{[(1S,2R)-2-(3,4-dihydro-2H-pyrrol-5-ylamino)cyclohexyl]amino}-6-methyl-N-(tetrahydro-2H-pyran-4-yl)quinazolin-2-carboxamide dihydrochloride Elemental analysis value (as $C_{25}H_{34}N_6O_2/2HCl/1.4H_2O$)
Calculated (%) C, 54.72; H, 7.13; N, 15.32.
Found (%) C, 55.01; H, 7.10; N, 14.93.
Positive ion FAB-MS m/z: 451 [M+H]$^+$
Specific rotation $[\alpha]^{20}_D$=+80.15 (c=0.519 methanol)
Appearance: white powder

Example 140

4-{[(1S,2R)-2-(3,4-dihydro-2H-pyrrol-5-ylamino)cyclohexyl]amino}-N-isopropyl-6-methylquinazolin-2-carboxamide dihydrochloride Elemental analysis value (as $C_{23}H_{32}N_6O/2HCl/1.3H_2O$)
Calculated (%) C, 54.72; H, 7.31; N, 16.65.
Found (%) C, 54.94; H, 7.45; N, 16.29.
Positive ion FAB-MS m/z: 409 [M+H]$^+$
Specific rotation $[\alpha]^{20}_D$=+96.16 (c=0.547 methanol)
Appearance: white powder

Example 141

4-{[(1S,2R)-2-(3,4-dihydro-2H-pyrrol-5-ylamino)cyclohexyl]amino}-N-(cis-4-methoxycyclohexyl)-6-methylquinazolin-2-carboxamide dihydrochloride Elemental analysis value (as $C_{27}H_{38}N_6O_2/2HCl/2.5H_2O$)
Calculated (%) C, 54.36; H, 7.60; N, 14.09.
Found (%) C, 54.39; H, 7.31; N, 13.99.
Positive ion FAB-MS m/z: 479 [M+H]$^+$
Specific rotation $[\alpha]^{20}_D$=+68.99 (c=0.516 methanol)
Appearance: white powder

Example 142

N-[(1-acetylpiperidin-4-yl)methyl]-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{28}H_{39}N_7O_2/2HCl/2.2H_2O$)
Calculated (%) C, 54.40; H, 7.40; N, 15.86.
Found (%) C, 54.73; H, 7.48; N, 15.48.
Positive ion FAB-MS m/z: 506 [M+H]$^+$
Specific rotation $[\alpha]^{20}_D$=+74.33 (c=0.487 methanol)
Appearance: white powder

Example 143

4-[((1S,2R)-2-{[(3R)-3-hydroxy-3,4-dihydro-2H-pyrrol-5-yl]amino}cyclohexyl)amino]-N-isobutyl-6-methylquinazolin-2-carboxamide dihydrochloride Elemental analysis value (as $C_{24}H_{34}N_6O_2/2HCl/0.4H_2O$)
Calculated (%) C, 55.57; H, 7.15; N, 16.20.
Found (%) C, 55.66; H, 7.39; N, 16.07.
Positive ion FAB-MS m/z: 439 [M+H]$^+$
Specific rotation $[\alpha]^{20}_D$=+109.62 (c=0.478 methanol)
Appearance: pale brown powder

Example 144

4-[((1S,2R)-2-{[(3S)-3-hydroxy-3,4-dihydro-2H-pyrrol-5-yl]amino}cyclohexyl)amino]-N-isobutyl-6-methylquinazolin-2-carboxamide dihydrochloride Elemental analysis value (as $C_{24}H_{34}N_6O_2/2HCl/0.9H_2O$)
Calculated (%) C, 54.63; H, 7.22; N, 15.93.
Found (%) C, 54.90; H, 7.15; N, 15.61.
Positive ion FAB-MS m/z: 439 [M+H]$^+$
Specific rotation $[\alpha]^{20}_D$=+51.83 (c=0.710 methanol)
Appearance: pale brown powder

Example 145

6-chloro-N-cycloheptyl-4-({(1S,2R)-2-[(2-oxo-3,4-dihydro-2H-pyrrol-5-yl)amino]cyclohexyl}amino)quinazolin-2-carboxamide dihydrochloride Elemental analysis value (as $C_{26}H_{33}N_6O_2Cl/2HCl/1.5H_2O$)
Calculated (%) C, 52.31; H, 6.42; N, 14.08.
Found (%) C, 52.38; H, 6.51; N, 14.11.
Positive ion FAB-MS m/z: 497 [M+H]$^+$
Specific rotation $[\alpha]^{20}_D$=+133.62 (c=0.464 methanol)
Appearance: white powder

Example 146

N-(tert-butoxy)-6-chloro-4-{[(1S,2R)-2-(3,4-dihydro-2H-pyrrol-5-ylamino)cyclohexyl]amino}quinazolin-2-carboxamide dihydrochloride Elemental analysis value (as $C_{23}H_{31}N_6O_2Cl/2HCl/H_2O$)
Calculated (%) C, 50.23; H, 6.42; N, 15.28.
Found (%) C, 49.97; H, 6.35; N, 14.99.
Positive ion FAB-MS m/z: 459 [M+H]$^+$
Specific rotation $[\alpha]^{20}_D$=+74.84 (c=0.473 methanol)
Appearance: white powder

Example 147

N-(cyclopentylmethyl)-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{26}H_{36}N_6O/2HCl/H_2O$)
Calculated (%) C, 55.65; H, 7.62; N, 14.98.
Found (%) C, 55.58; H, 7.24; N, 14.84.
Positive ion FAB-MS m/z: 449 [M+H]$^+$
Specific rotation $[\alpha]^{20}_D$=+51.66 (c=0.542 methanol)
Appearance: white powder

Example 148

4-{[(1S,2R)-2-(3,4-dihydro-2H-pyrrol-5-ylamino)cyclohexyl]amino}-6-methyl-N-[3-(methylthio)propyl]quinazolin-2-carboxamide dihydrochloride Elemental analysis value (as $C_{24}H_{34}N_6OS/2HCl/H_2O$)
Calculated (%) C, 52.84; H, 7.02; N, 15.40.
Found (%) C, 52.83; H, 7.11; N, 15.33.
Positive ion FAB-MS m/z: 455 [M+H]$^+$
Specific rotation $[\alpha]^{20}_D$=+82.04 (c=0.529 methanol)
Appearance: white powder

Example 149

4-{[(1S,2R)-2-(3,4-dihydro-2H-pyrrol-5-ylamino)cyclohexyl]amino}-N-(2-furylmethyl)-6-methylquinazolin-2-carboxamide dihydrochloride Elemental analysis value (as $C_{25}H_{30}N_6O_2/2HCl/H_2O$)
Calculated (%) C, 55.87; H, 6.38; N, 15.64.
Found (%) C, 56.09; H, 6.66; N, 15.26.
Positive ion FAB-MS m/z: 447 [M+H]$^+$
Specific rotation $[\alpha]^{20}_D$=+89.45 (c=0.474 methanol)
Appearance: white powder

Example 150

N-(tert-butoxy)-4-{[(1S,2R)-2-(3,4-dihydro-2H-pyrrol-5-ylamino)cyclohexyl]amino}-6-methylquinazolin-2-carboxamide dihydrochloride Elemental analysis value (as $C_{24}H_{34}N_6O_2/2HCl/0.7H_2O$)
Calculated (%) C, 55.00; H, 7.19; N, 16.04.
Found (%) C, 55.00; H, 7.15; N, 15.96.
Positive ion FAB-MS m/z: 439 [M+H]$^+$
Specific rotation $[\alpha]^{20}_D$=+85.48 (c=0.496 methanol)
Appearance: white powder

Example 151

4-{[(1S,2R)-2-(3,4-dihydro-2H-pyrrol-5-ylamino)cyclohexyl]amino}-6-methyl-N-(2,2,2-trifluoroethyl)quinazolin-2-carboxamide dihydrochloride Elemental analysis value (as $C_{22}H_{27}N_6OF_3/2HCl/0.7H_2O$)
Calculated (%) C, 49.48; H, 5.74; N, 15.74.
Found (%) C, 49.37; H, 5.72; N, 15.48.
Positive ion FAB-MS m/z: 449 [M+H]$^+$
Specific rotation $[\alpha]^{20}_D$=+104.62 (c=0.541 methanol)
Appearance: white powder

Example 152

4-{[(1S,2R)-2-(3,4-dihydro-2H-pyrrol-5-ylamino)cyclohexyl]amino}-N-(trans-4-hydroxycyclohexyl)-6-methylquinazolin-2-carboxamide dihydrochloride Positive ion FAB-MS m/z: 465 [M+H]$^+$
Specific rotation $[\alpha]^{20}_D$=+72.65 (c=0.490 methanol)
Appearance: white powder

Example 153

N-(4-methoxyphenyl)-6-methyl-4-{[(1S,2R)-2-(pyridin-2-ylamino)cyclohexyl]amino}quinazolin-2-carboxamide dihydrochloride Elemental analysis value (as $C_{28}H_{30}N_6O_2/2HCl/H_2O$)
Calculated (%) C, 58.64; H, 5.98; N, 14.65.
Found (%) C, 58.44; H, 5.90; N, 14.67.
Positive ion FAB-MS m/z: 482 [M+H]$^+$
Appearance: pale brown powder

Example 154

N-isobutyl-6-methyl-4-{[(1S,2R)-2-(pyridin-2-ylamino)cyclohexyl]amino}quinazolin-2-carboxamide dihydrochloride Elemental analysis value (as $C_{25}H_{32}N_6O/2HCl/1.5H_2O$)
Calculated (%) C, 56.39; H, 7.00; N, 15.78.

Found (%) C, 56.46; H, 6.74; N, 15.84.
Positive ion FAB-MS m/z: 432 [M+H]$^+$
Appearance: yellow powder

Example 155

6-chloro-4-[((1S,2R)-2-{[imino(phenyl)methyl]
amino}cyclohexyl)amino]-N-[2-(4-methoxyethyl)
ethyl]quinazolin-2-carboxamide dihydrochloride Elemental analysis value (as $C_{31}H_{33}N_6O_2Cl/2HCl/2.4H_2O$)
Calculated (%) C, 55.30; H, 5.96; N, 12.48.
Found (%) C, 55.26; H, 5.72; N, 12.25.
Positive ion FAB-MS m/z: 557 [M+H]$^+$
Specific rotation $[\alpha]^{20}_D$=+78.95 (c=0.537 methanol)
Appearance: pale brown powder

Example 156

6-chloro-N-(cyclopentylmethyl)-4-[((1S,2R)-2-{
[imino(phenyl)methyl]amino}cyclohexyl)amino]
quinazolin-2-carboxamide dihydrochloride Elemental analysis value (as $C_{28}H_{33}N_6OCl/2HCl/0.8H_2O$)
Calculated (%) C, 56.77; H, 6.23; N, 14.19.
Found (%) C, 56.81; H, 6.14; N, 13.91.
Positive ion FAB-MS m/z: 505 [M+H]$^+$
Specific rotation $[\alpha]^{20}_D$=+94.71 (c=0.549 methanol)
Appearance: white powder

Example 157

6-chloro-N-(3,3-dimethylbutyl)-4-[((1S,2R)-2-{
[imino(phenyl)methyl]amino}cyclohexyl)amino]
quinazolin-2-carboxamide dihydrochloride Elemental analysis value (as $C_{28}H_{35}N_6OCl/2HCl/0.8H_2O$)
Calculated (%) C, 56.58; H, 6.55; N, 14.14.
Found (%) C, 56.47; H, 6.48; N, 14.26.
Positive ion FAB-MS m/z: 507 [M+H]$^+$
Specific rotation $[\alpha]^{20}_D$=+103.51 (c=0.398 methanol)
Appearance: white powder

Example 158

6-chloro-N-(3-fluorobenzyl)-4-[((1S,2R)-2-{[imino
(phenyl)$_m$ethyl]amino}cyclohexyl)amino]quinazo-
lin-2-carboxamide dihydrochloride Elemental analysis value (as $C_{29}H_{28}N_6OClF/2HCl/1.5H_2O$)
Calculated (%) C, 55.20; H, 5.28; N, 13.32.
Found (%) C, 55.22; H, 5.21; N, 13.00.
Positive ion FAB-MS m/z: 531 [M+H]$^+$
Specific rotation $[\alpha]^{20}_D$=+91.81 (c=0.501 methanol)
Appearance: white powder

Example 159

4-[((1S,2R)-2-{[2-furyl(imino)methyl]
amino}cyclohexyl)amino]-N-(3-methoxypropyl)-6-
methylquinazolin-2-carboxamide dihydrochloride Elemental analysis value (as $C_{25}H_{32}N_6O_3/2HCl/0.9H_2O$)
Calculated (%) C, 54.23; H, 6.52; N, 15.18.
Found (%) C, 54.28; H, 6.50; N, 15.15.
Positive ion FAB-MS m/z: 465 [M+H]$^+$
Specific rotation $[\alpha]^{20}_D$=+76.07 (c=0.510 methanol)
Appearance: white powder

Example 160

4-[((1S,2R)-2-{[2-furyl(imino)methyl]
amino}cyclohexyl)amino]-N-(2-methoxyethyl)-6-
methylquinazolin-2-carboxamide dihydrochloride Elemental analysis value (as $C_{24}H_{30}N_6O_3/2HCl/1.2H_2O$)
Calculated (%) C, 52.89; H, 6.36; N, 15.42.
Found (%) C, 52.94; H, 6.28; N, 15.29.
Positive ion FAB-MS m/z: 451 [M+H]$^+$
Specific rotation $[\alpha]^{20}_D$=+104.31 (c=0.533 methanol)
Appearance: white powder

Example 161

N-(cyclohexylmethyl)-4-[((1S,2R)-2-{[imino(pyri-
din-2-yl)methyl]amino}cyclohexyl)amino]-6-meth-
ylquinazolin-2-carboxamide dihydrochloride Positive ion FAB-MS m/z: 476 [M+H]$^+$
Specific rotation $[\alpha]^{20}_D$=+53.58 (c=0.530 methanol)
Appearance: white powder

Example 162

4-[((1S,2R)-2-{[imino(pyridin-2-yl)methyl]
amino}cyclohexyl)amino]-N-isopropyl-6-meth-
ylquinazolin-2-carboxamide dihydrochloride Positive ion FAB-MS m/z: 446 [M+H]$^+$
Specific rotation $[\alpha]^{20}_D$=+93.55 (c=0.543 methanol)
Appearance: white powder

Example 163

N-(2-ethylbutyl)-4-[((1S,2R)-2-{[2-furyl(imino)me-
thyl]amino}cyclohexyl)amino]-6-methylquinazolin-
2-carboxamide dihydrochloride Elemental analysis value (as $C_{27}H_{36}N_6O_2/2HCl/1.5H_2O$)
Calculated (%) C, 56.25; H, 7.17; N, 14.58.
Found (%) C, 56.21; H, 6.96; N, 14.43.
Positive ion FAB-MS m/z: 477 [M+H]$^+$
Specific rotation $[\alpha]^{20}_D$=+58.41 (c=0.517 methanol)
Appearance: white powder

Example 164

N-(2-ethylbutyl)-4-[((1S,2R)-2-{[imino(pyridin-2-
yl)methyl]amino}cyclohexyl)amino]-6-meth-
ylquinazolin-2-carboxamide dihydrochloride Elemental analysis value (as $C_{28}H_{37}N_7O/2HCl/1.2H_2O$)
Calculated (%) C, 57.77; H, 7.17; N, 16.84.
Found (%) C, 57.88; H, 7.16; N, 16.54.
Positive ion FAB-MS m/z: 488 [M+H]$^+$
Specific rotation $[\alpha]^{20}_D$=+57.76 (c=0.554 methanol)
Appearance: white powder

Example 165

N-(cyclopropylmethyl)-4-[((1S,2R)-2-{[2-furyl(imino)methyl]amino}cyclohexyl)amino]-6-methylquinazolin-2-carboxamide dihydrochloride Elemental analysis value (as $C_{25}H_{30}N_6O_2/2HCl/1.2H_2O$)
Calculated (%) C, 55.49; H, 6.41; N, 15.53.
Found (%) C, 55.44; H, 6.34; N, 15.42.
Positive ion FAB-MS m/z: 447 [M+H]$^+$
Specific rotation $[\alpha]^{20}_D$=+72.26 (c=0.476 methanol)
Appearance: white powder

Example 166

4-[((1S,2R)-2-{[imino(pyridin-2-yl)methyl]amino}cyclohexyl)amino]-N-(3-methoxypropyl)-6-methylquinazolin-2-carboxamide dihydrochloride Positive ion FAB-MS m/z: 476 [M+H]$^+$
Specific rotation $[\alpha]^{20}_D$=+72.40 (c=0.511 methanol)
Appearance: white powder

Example 167

N-(2,2-dimethylpropyl)-4-[((1S,2R)-2-{[2-furyl(imino)methyl]amino}cyclohexyl)amino]-6-methylquinazolin-2-carboxamide dihydrochloride Elemental analysis value (as $C_{26}H_{34}N_6O_2/2HCl/0.9H_2O$)
Calculated (%) C, 56.60; H, 6.91; N, 15.23.
Found (%) C, 56.57; H, 6.74; N, 15.18.
Positive ion FAB-MS m/z: 463 [M+H]$^+$
Specific rotation $[\alpha]^{20}_D$=+67.63 (c=0.482 methanol)
Appearance: white powder

Example 168

4-[((1S,2R)-2-{[2-furyl(imino)methyl]amino}cyclohexyl)amino]-N-(3-methoxy-2,2-dimethylpropyl)-6-methylquinazolin-2-carboxamide dihydrochloride Elemental analysis value (as $C_{27}H_{36}N_6O_3/2HCl/1.4H_2O$)
Calculated (%) C, 54.90; H, 6.96; N, 14.23.
Found (%) C, 55.04; H, 6.90; N, 13.92.
Positive ion FAB-MS m/z: 493 [M+H]$^+$
Specific rotation $[\alpha]^{20}_D$=+58.92 (c=0.482 methanol)
Appearance: white powder

Example 169

4-[((1S,2R)-2-{[2-furyl(imino)methyl]amino}cyclohexyl)amino]-N-[1-(methoxymethyl)cyclohexyl]-6-methylquinazolin-2-carboxamide dihydrochloride Elemental analysis value (as $C_{29}H_{38}N_6O_3/2HCl/2H_2O$)
Calculated (%) C, 55.50; H, 7.07; N, 13.39.
Found (%) C, 55.53; H, 6.81; N, 13.14.
Positive ion FAB-MS m/z: 519 [M+H]$^+$
Specific rotation $[\alpha]^{20}_D$=+77.88 (c=0.416 methanol)
Appearance: white powder

Example 170

N-ethyl-4-[((1S,2R)-2-{[2-furyl(imino)methyl]amino}cyclohexyl)amino]-6-methylquinazolin-2-carboxamide dihydrochloride Elemental analysis value (as $C_{23}H_{28}N_6O_2/2HCl/2.7H_2O$)
Calculated (%) C, 50.96; H, 6.58; N, 15.50.
Found (%) C, 50.98; H, 6.18; N, 15.15.
Positive ion FAB-MS m/z: 421 [M+H]$^+$
Specific rotation $[\alpha]^{20}_D$=+86.40 (c=0.537 methanol)
Appearance: white powder

Example 171

4-[((1S,2R)-2-{[imino(phenyl)methyl]amino}cyclohexyl)amino]-N-(4-methoxyphenyl)-6-methylquinazolin-2-carboxamide dihydrochloride Elemental analysis value (as $C_{30}H_{32}N_6O_2/2HCl/2.6H_2O$)
Calculated (%) C, 57.34; H, 6.29; N, 13.37.
Found (%) C, 57.34; H, 6.15; N, 13.47.
Positive ion FAB-MS m/z: 509 [M+H]$^+$
Specific rotation $[\alpha]^{20}_D$=+12.54 (c=0.606 methanol)
Appearance: pale yellow powder

Example 172

N-n-butyl-4-[((1S,2R)-2-{[imino(phenyl)methyl]amino}cyclohexyl)amino]-6-methylquinazolin-2-carboxamide dihydrochloride Elemental analysis value (as $C_{27}H_{34}N_6O/2HCl/1.6H_2O$)
Calculated (%) C, 57.87; H, 7.05; N, 15.00.
Found (%) C, 57.80; H, 7.02; N, 14.82.
Positive ion FAB-MS m/z: 459 [M+H]$^+$
Specific rotation $[\alpha]^{20}_D$=+75.63 (c=0.788 methanol)
Appearance: white powder

Example 173

N-n-butyl-6-methyl-4-[((1S,2R)-2-{[(methylimino)(phenyl)methyl]amino}cyclohexyl)amino]quinazolin-2-carboxamide dihydrochloride Elemental analysis value (as $C_{28}H_{36}N_6O/2HCl/1.2H_2O$)
Calculated (%) C, 59.30; H, 7.18; N, 14.82.
Found (%) C, 59.22; H, 6.96; N, 14.94.
Positive ion FAB-MS m/z: 473 [M+H]$^+$
Specific rotation $[\alpha]^{20}_D$=+29.53 (c=0.684 methanol)
Appearance: white powder

Example 174

N-n-butyl-4-{[(1S,2R)-2-(1H-isoindol-3-ylamino)cyclohexyl]amino}-6-methylquinazolin-2-carboxamide dihydrochloride Elemental analysis value (as $C_{28}H_{34}N_6O/2HCl/1.2H_2O$)
Calculated (%) C, 59.51; H, 6.85; N, 14.87.
Found (%) C, 59.70; H, 6.76; N, 14.81.
Positive ion FAB-MS m/z: 471 [M+H]$^+$
Specific rotation $[\alpha]^{20}_D$=+46.63 (c=0.609 methanol)
Appearance: pale yellow powder

Example 175

N-n-butyl-4-[((1S,2R)-2-{[(hydroxyimino) (phenyl) methyl]amino}cyclohexyl)amino]-6-methylquinazolin-2-carboxamide dihydrochloride Elemental analysis value (as $C_{27}H_{34}N_6O_2/2HCl/0.8H_2O$)
Calculated (%) C, 57.71; H, 6.74; N, 14.96.
Found (%) C, 57.77; H, 6.63; N, 15.03.
Positive ion FAB-MS m/z: 475 [M+H]$^+$
Specific rotation $[\alpha]^{20}_D$=+3.13 (c=0.511 methanol)
Appearance: white powder

Example 176

4-[((1S,2R)-2-{[[2-(dimethylamino)phenyl](imino) methyl]amino}cyclohexyl)amino]-N-(4-methoxyphenyl)-6-methylquinazolin-2-carboxamide trihydrochloride Elemental analysis value (as $C_{32}H_{37}N_7O_2/3HCl/H_2O$)
Calculated (%) C, 56.60; H, 6.23; N, 14.44.
Found (%) C, 56.78; H, 6.24; N, 14.35.
Positive ion FAB-MS m/z: 552 [M+H]$^+$
Specific rotation $[\alpha]^{20}_D$=+21.93 (c=0.547 methanol)
Appearance: pale yellow powder

Example 177

4-[((1S,2R)-2-{[(3-fluorophenyl)(imino)methyl] amino}cyclohexyl)amino]-N-(4-methoxyphenyl)-6-methylquinazolin-2-carboxamide dihydrochloride Elemental analysis value (as $C_{30}H_{31}FN_6O_2/2HCl/0.8H_2O$)
Calculated (%) C, 58.69; H, 5.68; N, 13.69.
Found (%) C, 58.83; H, 5.55; N, 13.42.
Positive ion FAB-MS m/z: 527 [M+H]$^+$
Specific rotation $[\alpha]^{20}_D$=+12.78 (c=0.735 methanol)
Appearance: pale yellow powder

Example 178

4-[((1S,2R)-2-{[2-furyl(imino)methyl] amino}cyclohexyl)amino]-N-(4-methoxyphenyl)-6-methylquinazolin-2-carboxamide dihydrochloride Elemental analysis value (as $C_{28}H_{30}N_6O_3/2HCl/1.5H_2O$)
Calculated (%) C, 56.20; H, 5.89; N, 14.04.
Found (%) C, 56.22; H, 5.83; N, 13.82.
Positive ion FAB-MS m/z: 499 [M+H]$^+$
Specific rotation $[\alpha]^{20}_D$=+1.86 (c=0.642 methanol)
Appearance: pale yellow powder

Example 179

N-n-butyl-6-chloro-4-[((1S,2R)-2-{[imino(phenyl) methyl]amino}cyclohexyl)amino]quinazolin-2-carboxamide dihydrochloride Elemental analysis value (as $C_{26}H_{31}ClN_6O/2HCl/0.5H_2O$)
Calculated (%) C, 55.67; H, 6.11; N, 14.98.
Found (%) C, 55.68; H, 6.17; N, 14.86.
Positive ion FAB-MS m/z: 479 [M+H]$^+$
Specific rotation $[\alpha]^{20}_D$=+89.76 (c=0.684 methanol)
Appearance: white powder

Example 180

N-n-butyl-4-[((1S,2R)-2-{[imino(phenyl)methyl] amino}cyclohexyl)amino]-6-methoxyquinazolin-2-carboxamide dihydrochloride Elemental analysis value (as $C_{27}H_{34}N_6O_2/2HCl/1.25H_2O$)
Calculated (%) C, 56.89; H, 6.81; N, 14.74.
Found (%) C, 56.82; H, 6.65; N, 14.64.
Positive ion FAB-MS m/z: 475 [M+H]$^+$
Specific rotation $[\alpha]^{20}_D$=+108.39 (c=0.679 methanol)
Appearance: white powder

Example 181

4-[((1S,2S)-2-{[imino(phenyl)methyl] amino}cyclohexyl)amino]-N-(4-methoxyphenyl)-6-methylquinazolin-2-carboxamide dihydrochloride Elemental analysis value (as $C_{30}H_{32}N_6O_2/2HCl/1.2H_2O$)
Calculated (%) C, 59.74; H, 6.08; N, 13.93.
Found (%) C, 59.73; H, 5.99; N, 13.94.
Positive ion FAB-MS m/z: 509 [M+H]$^+$
Specific rotation $[\alpha]^{20}_D$=+40.36 (c=0.654 methanol)
Appearance: pale yellow powder

Example 182

6-chloro-N-cycloheptyl-4-[((1S,2R)-2-{[imino(phenyl)methyl]amino}cyclohexyl)amino]quinazolin-2-carboxamide dihydrochloride Elemental analysis value (as $C_{29}H_{35}ClN_6O/2HCl/1.2H_2O$)
Calculated (%) C, 56.76; H, 6.47; N, 13.70.
Found (%) C, 56.84; H, 6.31; N, 13.66.
Positive ion FAB-MS m/z: 519 [M+H]$^+$
Specific rotation $[\alpha]^{20}_D$=+100.55 (c=0.537 methanol)
Appearance: white powder

Example 183

N-cycloheptyl-4-[((1S,2R)-2-{[imino(phenyl)methyl]amino}cyclohexyl)amino]-6-methoxyquinazolin-2-carboxamide dihydrochloride Elemental analysis value (as $C_{30}H_{38}N_6O_2/2HCl/1.3H_2O$)
Calculated (%) C, 58.97; H, 7.03; N, 13.75.
Found (%) C, 58.95; H, 6.85; N, 13.76.
Positive ion FAB-MS m/z: 515 [M+H]$^+$
Specific rotation $[\alpha]^{20}_D$=+109.66 (c=0.538 methanol)
Appearance: white powder

Example 184

N-cycloheptyl-4-[((1S,2R)-2-{[imino(phenyl)methyl]amino}cyclohexyl)amino]-6-methylquinazolin-2-carboxamide dihydrochloride Elemental analysis value (as $C_{30}H_{38}N_6O/2HCl/2H_2O$)
Calculated (%) C, 59.30; H, 7.30; N, 13.83.
Found (%) C, 59.12; H, 7.03; N, 13.99.
Positive ion FAB-MS m/z: 499 [M+H]$^+$
Specific rotation $[\alpha]^{20}_D$=+85.09 (c=0.463 methanol)
Appearance: white powder

Example 185

6-chloro-N-cycloheptyl-4-[((1S,2R)-2-{[2-furyl(imino)methyl]amino}cyclohexyl)amino]quinazolin-2-carboxamide dihydrochloride Elemental analysis value (as $C_{27}H_{33}ClN_6O_2/2HCl/2.2H_2O$)
Calculated (%) C, 52.17; H, 6.39; N, 13.52.
Found (%) C, 52.17; H, 6.15; N, 13.70.
Positive ion FAB-MS m/z: 509 [M+H]$^+$
Specific rotation $[\alpha]^{20}_D$=+109.94 (c=0.573 methanol)
Appearance: white powder

Example 186

N-isobutyl-4-{[(1S,2R)-2-(1H-isoindol-3-ylamino)cyclohexyl]amino}-6-methylquinazolin-2-carboxamide dihydrochloride Elemental analysis value (as $C_{28}H_{34}N_6O/2HCl/1.5H_2O$)
Calculated (%) C, 58.94; H, 6.90; N, 14.73.
Found (%) C, 59.14; H, 6.88; N, 14.60.
Positive ion FAB-MS m/z: 471 [M+H]$^+$
Specific rotation $[\alpha]^{20}_D$=+68.82 (c=0.555 methanol)
Appearance: white powder

Example 187

N-cycloheptyl-4-{[(1S,2R)-2-(1H-isoindol-3-ylamino)cyclohexyl]amino}-6-methylquinazolin-2-carboxamide dihydrochloride Elemental analysis value (as $C_{31}H_{38}N_6O/2HCl/2H_2O$)
Calculated (%) C, 60.09; H, 7.16; N, 13.56.
Found (%) C, 59.88; H, 7.13; N, 13.58.
Positive ion FAB-MS m/z: 511 [M+H]$^+$
Specific rotation $[\alpha]^{20}_D$=+29.96 (c=0.534 methanol)
Appearance: pale yellow powder

Example 188

6-chloro-N-cycloheptyl-4-[((1S,2R)-2-{[imino(pyridin-2-yl)methyl]amino}cyclohexyl)amino]quinazolin-2-carboxamide dihydrochloride Elemental analysis value (as $C_{28}H_{34}ClN_7O/2HCl/2.2H_2O$)
Calculated (%) C, 53.16; H, 6.44; N, 15.50.
Found (%) C, 53.20; H, 6.59; N, 15.32.
Positive ion FAB-MS m/z: 520 [M+H]$^+$
Specific rotation $[\alpha]^{20}_D$=+93.92 (c=0.477 methanol)
Appearance: white powder

Example 189

N-n-butyl-4-[((1S,2R)-2-{[imino(pyridin-2-yl)methyl]amino}cyclohexyl)amino]-6-methylquinazolin-2-carboxamide dihydrochloride Elemental analysis value (as $C_{26}H_{33}N_7O/2HCl/2.5H_2O$)
Calculated (%) C, 54.07; H, 6.98; N, 16.98.
Found (%) C, 53.87; H, 7.36; N, 16.73.
Positive ion FAB-MS m/z: 460 [M+H]$^+$
Specific rotation $[\alpha]^{20}_D$=+75.62 (c=0.521 methanol)
Appearance: white powder

Example 190

4-[((1S,2R)-2-{[imino(pyridin-2-yl)methyl]amino}cyclohexyl)amino]-N-(3-methoxy-2,2-dimethylpropyl)-6-methylquinazolin-2-carboxamide dihydrochloride Elemental analysis value (as $C_{28}H_{37}N_7O_2/2HCl/1.6H_2O$)
Calculated (%) C, 55.55; H, 7.03; N, 16.20.
Found (%) C, 55.76; H, 6.77; N, 15.95.
Positive ion FAB-MS m/z: 504 [M+H]$^+$
Specific rotation $[\alpha]^{20}_D$=+49.33 (c=0.454 methanol)
Appearance: white powder

Example 191

N-ethyl-4-[((1S,2R)-2-{[imino(pyridin-2-yl)methyl]amino}cyclohexyl)amino]-6-methylquinazolin-2-carboxamide dihydrochloride Elemental analysis value (as $C_{24}H_{29}N_7O/2HCl/1.5H_2O$)
Calculated (%) C, 54.24; H, 6.45; N, 18.45.
Found (%) C, 54.14; H, 6.49; N, 18.28.
Positive ion FAB-MS m/z: 432 [M+H]$^+$
Specific rotation $[\alpha]^{20}_D$=+93.78 (c=0.499 methanol)
Appearance: white powder

Example 192

4-[((1S,2R)-2-{[imino(pyridin-2-yl)methyl]amino}cyclohexyl)amino]-N-(2-methoxy-1,1-dimethylethyl)-6-methylquinazolin-2-carboxamide trihydrochloride Elemental analysis value (as $C_{27}H_{35}N_7O_2/3HCl/1.4H_2O$)
Calculated (%) C, 51.95; H, 6.59; N, 15.71.
Found (%) C, 52.10; H, 6.62; N, 15.42.
Positive ion FAB-MS m/z: 490 [M+H]$^+$
Specific rotation $[\alpha]^{20}_D$=+88.29 (c=0.564 methanol)
Appearance: white powder

Example 193

4-[((1S,2R)-2-{[2-furyl(imino)methyl]amino}cyclohexyl)amino]-N-(trans-4-methoxycyclohexyl)-6-methylquinazolin-2-carboxamide dihydrochloride Elemental analysis value (as $C_{28}H_{36}N_6O_3/2HCl/H_2O$)
Calculated (%) C, 56.47; H, 6.77; N, 14.11.
Found (%) C, 56.46; H, 6.88; N, 14.11.
Positive ion FAB-MS m/z: 505 [M+H]$^+$
Specific rotation $[\alpha]^{20}_D$=+78.74 (c=0.508 methanol)
Appearance: white powder

Example 194

N-(2,2-dimethylpropyl)-4-[((1S,2R)-2-{[imino(1H-pyrrol-2-yl)methyl]amino}cyclohexyl)amino]-6-methylquinazolin-2-carboxamide dihydrochloride Elemental analysis value (as $C_{26}H_{35}N_7O/2HCl/0.75H_2O$)
Calculated (%) C, 56.98; H, 7.08; N, 17.89.
Found (%) C, 57.19; H, 6.85; N, 17.70.
Positive ion FAB-MS m/z: 462 [M+H]$^+$
Specific rotation $[\alpha]^{20}_D$=25.62 (c=0.484 methanol)
Appearance: white powder

Example 195

6-fluoro-4-[((1S,2R)-2-{[2-furyl(imino)methyl]amino}cyclohexyl)amino]-N-(trans-4-methoxycyclohexyl)quinazolin-2-carb oxamide dihydrochloride Elemental analysis value (as $C_{27}H_{33}FN_6O_3/2HCl/1.8H_2O$)
Calculated (%) C, 52.82; H, 6.34; N, 13.69.
Found (%) C, 52.94; H, 6.23; N, 13.72.
Positive ion FAB-MS m/z: 509 [M+H]$^+$
Specific rotation $[\alpha]^{20}_D$=+36.36 (c=0.495 methanol)
Appearance: white powder

Example 196

4-[((1S,2R)-2-{[3-furyl(imino)methyl]amino}cyclohexyl)amino]-N-(trans-4-methoxycyclohexyl)-6-methylquinazolin-2-carboxamide dihydrochloride Elemental analysis value (as $C_{28}H_{36}N_6O_3/2HCl/1.4H_2O$)
Calculated (%) C, 55.79; H, 6.82; N, 13.94.
Found (%) C, 55.94; H, 6.73; N, 13.69.
Positive ion FAB-MS m/z: 505 [M+H]$^+$
Specific rotation $[\alpha]^{20}_D$=+88.09 (c=0.563 methanol)
Appearance: white powder

Example 197

N-(4,4-difluorocyclohexyl)-4-[((1S,2R)-2-{[2-furyl(imino)methyl]amino}cyclohexyl)amino]-6-methylquinazolin-2-carboxamide dihydrochloride Positive ion FAB-MS m/z: 511 [M+H]$^+$
Specific rotation $[\alpha]^{20}_D$=+79.24 (c=0.530 methanol)
Appearance: white powder

Example 198

4-[((1S,2R)-2-{[imino(pyridin-2-yl)methyl]amino}cyclohexyl)amino]-N-(4-methoxyphenyl)-6-methylquinazolin-2-carboxamide trihydrochloride Positive ion FAB-MS m/z: 509 [M+H]$^+$
Specific rotation $[\alpha]^{20}_D$=−4.42 (c=0.995 methanol)
Appearance: golden yellow powder

Example 199

4-[((1S,2R)-2-{[imino(pyridin-3-yl)methyl]amino}cyclohexyl)amino]-N-(4-methoxyphenyl)-6-methylquinazolin-2-carboxamide trihydrochloride Elemental analysis value (as $C_{29}H_{31}N_7O_2/3HCl/1.5H_2O$)
Calculated (%) C, 53.92; H, 5.77; N, 15.18.
Found (%) C, 53.89; H, 5.80; N, 15.14.
Positive ion FAB-MS m/z: 509 [M+H]$^+$
Specific rotation $[\alpha]^{20}_D$=−23.50 (c=0.570 methanol)
Appearance: yellow powder

Example 200

4-[((1S,2R)-2-{[imino(pyridin-4-yl)methyl]amino}cyclohexyl)amino]-N-(4-methoxyphenyl)-6-methylquinazolin-2-carboxamide trihydrochloride Elemental analysis value (as $C_{29}H_{31}N_7O_2/3HCl/0.3H_2O$)
Calculated (%) C, 55.78; H, 5.59; N, 15.70.
Found (%) C, 55.76; H, 5.77; N, 15.74.
Positive ion FAB-MS m/z: 509 [M+H]$^+$
Specific rotation $[\alpha]^{20}_D$=−9.04 (c=1.105 methanol)
Appearance: yellow powder

Example 201

6-chloro-N-cycloheptyl-4-{[(1S,2R)-2-(quinazolin-4-ylamino)cyclohexyl]amino}quinazolin-2-carboxamide dihydrochloride Elemental analysis value (as $C_{30}H_{34}N_7OCl/2HCl/0.8H_2O$)
Calculated (%) C, 57.07; H, 6.00; N, 15.53.
Found (%) C, 57.06; H, 5.94; N, 15.32.
Positive ion FAB-MS m/z: 544 [M+H]$^+$
Specific rotation $[\alpha]^{20}_D$=+7.06 (c=0.764 methanol)
Appearance: white powder

Example 202

4-[((1S,2R)-2-{[imino(phenyl)methyl]amino}cyclohexyl)amino]-N-isobutyl-6-methylquinazolin-2-carboxamide dihydrochloride Elemental analysis value (as $C_{27}H_{34}N_6O/2HCl/2.2H_2O$)
Calculated (%) C, 56.78; H, 7.13; N, 14.71.
Found (%) C, 56.71; H, 6.82; N, 14.62.
Positive ion FAB-MS m/z: 459 [M+H]$^+$
Specific rotation $[\alpha]^{20}_D$=+72.00 (c=0.500 methanol)
Appearance: white powder

Example 203

6-chloro-N-cycloheptyl-4-[((1S,2R)-2-{[(3-fluorophenyl)(imino)methyl]amino}cyclohexyl)amino]quinazolin-2-carboxamide dihydrochloride Elemental analysis value (as $C_{29}H_{34}N_6OClF/2HCl/2.5H_2O$)
Calculated (%) C, 53.18; H, 6.31; N, 12.83.
Found (%) C, 53.40; H, 6.14; N, 12.70.
Positive ion FAB-MS m/z: 537 [M+H]$^+$
Specific rotation $[\alpha]^{20}_D$=+82.28 (c=0.559 methanol)
Appearance: white powder

Example 204

4-[((1S,2R)-2-{[imino(pyridin-2-yl)methyl]amino}cyclohexyl)amino]-N-(2-isopropoxyethyl)-6-methylquinazolin-2-carboxamide dihydrochloride Positive ion FAB-MS m/z: 490 [M+H]$^+$
Specific rotation $[\alpha]^{20}_D$=+107.86 (c=0.534 methanol)
Appearance: white powder

Example 205

4-[((1S,2R)-2-{[imino(pyridin-2-yl)methyl]amino}cyclohexyl)amino]-6-methyl-N-[2-(methylthio)ethyl]quinazolin-2-carboxamide dihydrochloride Positive ion FAB-MS m/z: 478 [M+H]$^+$
Specific rotation $[\alpha]^{20}_D$=+74.85 (c=0.521 methanol)
Appearance: white powder

Example 206

4-[((1S,2R)-2-{[imino(4-methoxyphenyl)methyl]amino}cyclohexyl)amino]-N-isobutyl-6-methylquinazolin-2-carboxamide dihydrochloride Elemental analysis value (as $C_{28}H_{36}N_6O_2/2HCl/H_2O$)
Calculated (%) C, 58.03; H, 6.96; N, 14.50.
Found (%) C, 58.05; H, 6.91; N, 14.59.
Positive ion FAB-MS m/z: 489 [M+H]$^+$
Specific rotation $[\alpha]^{20}{}_D$=+55.88 (c=0.476 methanol)
Appearance: white powder

Example 207

4-[((1S,2R)-2-{[imino(phenyl)methyl]amino}cyclohexyl)amino]-N-(3-methoxypropyl)-6-methylquinazolin-2-carboxamide dihydrochloride Elemental analysis value (as $C_{27}H_{34}N_6O_2/2HCl/2.5H_2O$)
Calculated (%) C, 54.73; H, 6.97; N, 14.18.
Found (%) C, 54.71; H, 6.60; N, 14.21.
Positive ion FAB-MS m/z: 475 [M+H]$^+$
Specific rotation $[\alpha]^{20}{}_D$=+73.66 (c=0.505 methanol)
Appearance: pale brown powder

Example 208

4-[((1S,2R)-2-{[amino(methoxyimino)methyl]amino}cyclohexyl)amino]-N-(2-methoxyethyl)-6-methylquinazolin-2-carboxamide dihydrochloride Step 1: 4-{[(1S,2R)-2-(cyanoamino)cyclohexyl]amino}-N-(2-methoxyethyl)-6-methylquinazolin-2-carboxamide In an argon atmosphere, to a solution of 3.30 g of 4-{[(1S,2R)-2-aminocyclohexyl]amino}-N-(2-methoxyethyl)-6-methylquinazolin-2-carboxamide in 80 ml of tetrahydrofuran, 1.54 ml of triethylamine and 978 mg of cyanogen bromide were sequentially added at −20° C., and the mixture was stirred at the same temperature for 0.5 hour. Water was added to the reaction solution, and the mixture was subjected to an extraction with ethyl acetate. The organic layer was washed with water and saturated brine and dried over magnesium sulfate. The solvent was distilled off, and the residue was purified by silica gel column chromatography (chloroform:methanol=50:1), whereby 1.96 g of a desired compound was obtained as a pale yellow crystal.

Step 2: 4-[((1S,2R)-2-{[amino(methoxyimino)methyl]amino}cyclohexyl)amino]-N-(2-methoxyethyl)-6-methylquinazolin-2-carboxamide To a solution of 1.96 g of 4-{[(1S,2R)-2-(cyanoamino)cyclohexyl]amino}-N-(2-methoxyethyl)-6-methylquinazolin-2-carboxamide and 8.56 g of methoxyamine hydrochloride in 80 ml of ethanol, 10.86 g of sodium carbonate was added and the mixture was heated at reflux for 1 hour. The reaction solution was added to 400 ml of ice water, and the deposited substance was collected by filtration. After the collected deposited substance was washed with water, it was dried under reduced pressure. The obtained powder was washed with a mixed solution of (chloroform:diisopropyl alcohol=1:1), whereby 1.71 g of a desired compound was obtained as a white powder.

Elemental analysis value (as $C_{21}H_{31}N_7O_3$)
Calculated (%) C, 58.72; H, 7.27; N, 22.83.
Found (%) C, 58.48; H, 7.17; N, 22.76.
Positive ion FAB-MS m/z: 430 [M+H]$^+$
Appearance: white powder Step 3: 4-[((1S,2R)-2-{[amino(methoxyimino)methyl]amino}cyclohexyl)amino]-N-(2-methoxyethyl)-6-methylquinazolin-2-carboxamide dihydrochloride 1.71 g of 4-[((1S,2R)-2-{[amino(methoxyimino)methyl]amino}cyclohexyl)amino]-N-(2-methoxyethyl)-6-methyl quinazolin-2-carboxamide was suspended in 20 ml of ethyl acetate, and 5 ml of a 4 N hydrogen chloride-ethyl acetate solution was added thereto, and the mixture was stirred for 15 minutes. To the reaction solution, 40 ml of diethyl ether was added, and the resulting deposited substance was collected by filtration, washed with diethyl ether and dried under reduced pressure, whereby 2.01 g of a desired compound was obtained as a white powder.

Positive ion FAB-MS m/z: 430 [M+H]$^+$
Specific rotation $[\alpha]^{20}{}_D$=+56.80 (c=0.500 methanol)

In the same manner as in Example 208, the following compounds of Examples 209 to 247, 249 and 250 were produced.

Example 209

4-[((1S,2R)-2-{[amino(methoxyimino)methyl]amino}cyclohexyl)amino]-N-(4-methoxyphenyl)-6-methylquinazolin-2-carboxamide dihydrochloride Elemental analysis value (as $C_{25}H_{31}N_7O_3/2HCl/0.6H_2O$)
Calculated (%) C, 53.50; H, 6.14; N, 17.48.
Found (%) C, 53.81; H, 6.11; N, 17.14.
Positive ion FAB-MS m/z: 478 [M+H]$^+$
Specific rotation $[\alpha]^{20}{}_D$=−20.23 (c=0.771 methanol)
Appearance: yellow powder

Example 210

4-[((1S,2R)-2-{[amino(hydroxyimino)methyl]amino}cyclohexyl)amino]-N-(4-methoxyphenyl)-6-methylquinazolin-2-carboxamide dihydrochloride Elemental analysis value (as $C_{24}H_{29}N_7O_3/2HCl/H_2O$)
Calculated (%) C, 51.99; H, 6.00; N, 17.68.
Found (%) C, 52.23; H, 6.07; N, 17.55.
Positive ion FAB-MS m/z: 464 [M+H]$^+$
Specific rotation $[\alpha]^{20}{}_D$=−34.15 (c=0.650 methanol)
Appearance: pale yellow powder

Example 211

4-[((1S,2R)-2-{[amino(methoxyimino)methyl]amino}cyclohexyl)amino]-N-isobutyl-6-methylquinazolin-2-carboxamide dihydrochloride Elemental analysis value (as $C_{22}H_{33}N_7O_2/2HCl/2.5H_2O$)
Calculated (%) C, 48.44; H, 7.39; N, 17.97.
Found (%) C, 48.59; H, 7.05; N, 17.88.
Positive ion FAB-MS m/z: 428 [M+H]$^+$
Specific rotation $[\alpha]^{20}{}_D$=+45.71 (c=0.525 methanol)
Appearance: white powder

Example 212

4-[((1S,2R)-2-{[amino(hydroxyimino)methyl]amino}cyclohexyl)amino]-N-isobutyl-6-methylquinazolin-2-carboxamide dihydrochloride Positive ion FAB-MS m/z: 414 [M+H]$^+$
Specific rotation $[\alpha]^{20}_D$=+33.55 (c=0.590 methanol)
Appearance: white powder

Example 213

4-[((1S,2R)-2-{[amino(methoxyimino)methyl]amino}cyclohexyl)amino]-6-methyl-N-(n-propyl)quinazolin-2-carboxamide dihydrochloride Elemental analysis value (as $C_{21}H_{31}N_7O_2$/2HCl/1.8H$_2$O)
Calculated (%) C, 48.61; H, 7.11; N, 18.90.
Found (%) C, 48.32; H, 6.71; N, 18.60.
Positive ion FAB-MS m/z: 414 [M+H]$^+$
Specific rotation $[\alpha]^{20}_D$=+48.84 (c=0.520 methanol)
Appearance: white powder

Example 214

4-[((1S,2R)-2-{[amino(methoxyimino)methyl]amino}cyclohexyl)amino]-N-(cyclopropylmethyl)-6-methylquinazolin-2-carboxamide dihydrochloride Positive ion FAB-MS m/z: 426 [M+H]$^+$
Specific rotation $[\alpha]^{20}_D$=+46.72 (c=0.535 methanol)
Appearance: white powder

Example 215

4-[((1S,2R)-2-{[amino(methoxyimino)methyl]amino}cyclohexyl)amino]-N-(2-hydroxyethyl)-6-methylquinazolin-2-carboxamide dihydrochloride Elemental analysis value (as $C_{20}H_{29}N_7O_3$/2HCl/3H$_2$O)
Calculated (%) C, 44.28; H, 6.87; N, 18.07.
Found (%) C, 44.59; H, 6.48; N, 18.14.
Positive ion FAB-MS m/z: 416 [M+H]$^+$
Specific rotation $[\alpha]^{20}_D$=+56.32 (c=0.625 methanol)
Appearance: white powder

Example 216

4-[((1S,2R)-2-{[amino(methoxyimino)methyl]amino}cyclohexyl)amino]-N-isopropyl-6-methylquinazolin-2-carboxamide dihydrochloride Elemental analysis value (as $C_{21}H_{31}N_7O_2$/2HCl/2H$_2$O)
Calculated (%) C, 48.28; H, 7.14; N, 18.77.
Found (%) C, 48.52; H, 6.79; N, 18.72.
Positive ion FAB-MS m/z: 414 [M+H]$^+$
Specific rotation $[\alpha]^{20}_D$=+43.61 (c=0.720 methanol)
Appearance: white powder

Example 217

4-[((1S,2R)-2-{[amino(methoxyimino)methyl]amino}cyclohexyl)amino]-N-cyclopropyl-6-methylquinazolin-2-carboxamide dihydrochloride Positive ion FAB-MS m/z: 412 [M+H]$^+$
Specific rotation $[\alpha]^{20}_D$=+49.39 (c=0.575 methanol)
Appearance: white powder

Example 218

4-[((1S,2R)-2-{[amino(methoxyimino)methyl]amino}cyclohexyl)amino]-N-cyclobutyl-6-methylquinazolin-2-carboxamide dihydrochloride Elemental analysis value (as $C_{22}H_{31}N_7O_2$/2HCl/1.6H$_2$O)
Calculated (%) C, 50.11; H, 6.92; N, 18.59.
Found (%) C, 50.19; H, 6.69; N, 18.55.
Positive ion FAB-MS m/z: 426 [M+H]$^+$
Specific rotation $[\alpha]^{20}_D$=+35.10 (c=0.490 methanol)
Appearance: white powder

Example 219

4-[((1S,2R)-2-{[amino(methoxyimino)methyl]amino}cyclohexyl)amino]-6-methyl-N-(2,2,2-trifluoroethyl)quinazolin-2-carboxamide dihydrochloride Positive ion FAB-MS m/z: 454 [M+H]$^+$
Specific rotation $[\alpha]^{20}_D$=+56.92 (c=0.520 methanol)
Appearance: white powder

Example 220

4-[((1S,2R)-2-{[amino(methoxyimino)methyl]amino}cyclohexyl)amino]-N-ethyl-N,6-dimethylquinazolin-2-carboxamide dihydrochloride Elemental analysis value (as $C_{21}H_{31}N_7O_2$/2HCl/2.3H$_2$O)
Calculated (%) C, 47.78; H, 7.18; N, 18.57.
Found (%) C, 47.80; H, 6.74; N, 18.53.
Positive ion FAB-MS m/z: 414 [M+H]$^+$
Specific rotation $[\alpha]^{20}_D$=+37.14 (c=0.490 methanol)
Appearance: white powder

Example 221

4-[((1S,2R)-2-{[imino(1,2-oxazinan-2-yl)methyl]amino}cyclohexyl)amino]-N-(4-methoxyphenyl)-6-methylquinazolin-2-carboxamide dihydrochloride Elemental analysis value (as $C_{28}H_{35}N_7O_3$/2HCl/0.8H$_2$O)
Calculated (%) C, 55.59; H, 6.43; N, 16.21.
Found (%) C, 55.89; H, 6.66; N, 15.87.
Positive ion FAB-MS m/z: 518 [M+H]$^+$
Specific rotation $[\alpha]^{20}_D$=−14.90 (c=0.510 methanol)
Appearance: yellow powder

Example 222

6-chloro-N-cycloheptyl-4-[((1S,2R)-2-{[imino(1,2-oxazinan-2-yl)methyl]amino}cyclohexyl)amino]quinazolin-2-carboxamide dihydrochloride Elemental analysis value (as $C_{27}H_{38}N_7O_2Cl$/2HCl/2.2H$_2$O)
Calculated (%) C, 50.62; H, 6.99; N, 15.30.
Found (%) C, 50.45; H, 6.59; N, 15.19.
Positive ion FAB-MS m/z: 528 [M+H]$^+$
Specific rotation $[\alpha]^{20}_D$=+57.73 (c=0.485 methanol)
Appearance: white powder

Example 223

4-[((1S,2R)-2-{[imino(1,2-oxazinan-2-yl)methyl]amino}cyclo hexyl)amino]-N-isobutyl-6-methylquinazolin-2-carboxamide dihydrochloride Elemental analysis value (as $C_{25}H_{37}N_7O_2/2HCl/H_2O$)
Calculated (%) C, 53.76; H, 7.40; N, 17.55.
Found (%) C, 53.51; H, 7.20; N, 17.26.
Positive ion FAB-MS m/z: 468 [M+H]$^+$
Specific rotation $[\alpha]^{20}_D$=+56.76 (c=0.532 methanol)
Appearance: white powder

Example 224

N-cycloheptyl-4-[((1S,2R)-2-{[imino(1,2-oxazinan-2-yl)meth yl]amino}cyclohexyl)amino]-6-methylquinazolin-2-carboxamide dihydrochloride Elemental analysis value (as $C_{28}H_{41}N_7O_2/2HCl/1.5H_2O$)
Calculated (%) C, 55.35; H, 7.63; N, 16.14.
Found (%) C, 55.67; H, 7.73; N, 15.92.
Positive ion FAB-MS m/z: 508 [M+H]$^+$
Specific rotation $[\alpha]^{20}_D$=+52.47 (c=0.404 methanol)
Appearance: white powder

Example 225

6-chloro-N-cycloheptyl-4-[((1S,2R)-2-{[imino(isoxazolidin-2-yl)methyl]amino}cyclohexyl)amino]quinazolin-2-carboxamide dihydrochloride Elemental analysis value (as $C_{26}H_{36}N_7O_2Cl/2HCl/2.5H_2O$)
Calculated (%) C, 49.41; H, 6.86; N, 15.51.
Found (%) C, 49.18; H, 6.86; N, 15.41.
Positive ion FAB-MS m/z: 514 [M+H]$^+$
Specific rotation $[\alpha]^{20}_D$=+76.82 (c=0.492 methanol)
Appearance: white powder

Example 226

4-[((1S,2R)-2-{[amino(methoxyimino)methyl]amino}cyclohexyl)amino]-6-chloro-N-cycloheptylquinazolin-2-carboxamide dihydrochloride Elemental analysis value (as $C_{24}H_{34}N_7O_2Cl/2HCl/H_2O$)
Calculated (%) C, 49.79; H, 6.62; N, 16.93.
Found (%) C, 49.66; H, 6.54; N, 17.12.
Positive ion FAB-MS m/z: 488 [M+H]$^+$
Specific rotation $[\alpha]^{20}_D$=+54.20 (c=0.424 methanol)
Appearance: white powder

Example 227

6-chloro-N-cycloheptyl-4-{[(1S,2R)-2-({imino[methoxy(methyl)amino]methyl}amino)cyclohexyl]amino}quinazolin-2-carboxamide dihydrochloride Elemental analysis value (as $C_{25}H_{36}N_7O_2Cl/2HCl/2.5H_2O$)
Calculated (%) C, 48.43; H, 6.99; N, 15.81.
Found (%) C, 48.28; H, 6.60; N, 15.97.
Positive ion FAB-MS m/z: 502 [M+H]$^+$
Specific rotation $[\alpha]^{20}_D$=+78.83 (c=0.515 methanol)
Appearance: white powder

Example 228

N-(2,2-dimethylpropyl)-4-[((1S,2R)-2-{[imino(isoxazolidin-2-yl)methyl]amino}cyclohexyl)amino]-6-methylquinazolin-2-carboxamide dihydrochloride Positive ion FAB-MS m/z: 468 [M+H]$^+$
Specific rotation $[\alpha]^{20}_D$=+50.28 (c=0.533 methanol)
Appearance: white powder

Example 229

4-[((1S,2R)-2-{[imino(isoxazolidin-2-yl)methyl]amino}cyclo hexyl)amino]-6-methyl-N-[3-(methylthio)propyl]quinazolin-2-carboxamide dihydrochloride Elemental analysis value (as $C_{24}H_{35}N_7O_2S/2HCl/H_2O$)
Calculated (%) C, 49.99; H, 6.82; N, 17.00.
Found (%) C, 50.05; H, 6.72; N, 16.87.
Positive ion FAB-MS m/z: 486 [M+H]$^+$
Specific rotation $[\alpha]^{20}_D$=+56.42 (c=0.514 methanol)
Appearance: white powder

Example 230

4-[((1S,2R)-2-{[imino(isoxazolidin-2-yl)methyl]amino}cyclo hexyl)amino]-N-(3-methoxy-2,2-dimethylpropyl)-6-methylquinazolin-2-carboxamide dihydrochloride Elemental analysis value (as $C_{26}H_{39}N_7O_3/2HCl/H_2O$)
Calculated (%) C, 53.06; H, 7.36; N, 16.66.
Found (%) C, 53.44; H, 7.13; N, 16.52.
Positive ion FAB-MS m/z: 498 [M+H]$^+$
Specific rotation $[\alpha]^{20}_D$=+48.19 (c=0.527 methanol)
Appearance: pale yellow powder

Example 231

4-[((1S,2R)-2-{[imino(isoxazolidin-2-yl)methyl]amino}cyclohexyl)amino]-6-methyl-N-(tetrahydro-2H-pyran-4-yl)quinazolin-2-carboxamide dihydrochloride Elemental analysis value (as $C_{25}H_{35}N_7O_3/2HCl/2.4H_2O$)
Calculated (%) C, 50.23; H, 7.05; N, 16.40.
Found (%) C, 50.29; H, 6.88; N, 16.39.
Positive ion FAB-MS m/z: 482 [M+H]$^+$
Specific rotation $[\alpha]^{20}_D$=+62.18 (c=0.550 methanol)
Appearance: white powder

Example 232

4-[((1S,2R)-2-{[imino(isoxazolidin-2-yl)methyl]amino}cyclo hexyl)amino]-N-(trans-4-methoxycyclohexyl)-6-methylquinazolin-2-carboxamide dihydrochloride Elemental analysis value (as $C_{27}H_{39}N_7O_3/2HCl/2H_2O$)
Calculated (%) C, 52.42; H, 7.33; N, 15.85.
Found (%) C, 52.13; H, 7.19; N, 15.69.
Positive ion FAB-MS m/z: 510 [M+H]$^+$
Specific rotation $[\alpha]^{20}_D$=+61.67 (c=0.548 methanol)
Appearance: white powder

Example 233

N-(2-ethylbutyl)-4-[((1S,2R)-2-{[imino(isoxazolidin-2-yl)$_m$ethyl]amino}cyclohexyl)amino]-6-methylquinazoline-2-carboxamide dihydrochloride Elemental analysis value (as $C_{26}H_{39}N_7O_2/2HCl/H_2O$)
Calculated (%) C, 54.54; H, 7.57; N, 17.12.
Found (%) C, 54.49; H, 7.38; N, 16.91.
Positive ion FAB-MS m/z: 482 [M+H]$^+$
Specific rotation $[\alpha]^{20}_D$=+52.57 (c=0.563 methanol)
Appearance: white powder

Example 234

N-(2,2-dimethylpropyl)-4-{[(1S,2R)-2-({imino[methoxy(methyl)amino]methyl}amino)cyclohexyl]amino}-6-methylquinazolin-2-carboxamide dihydrochloride Elemental analysis value (as $C_{24}H_{37}N_7O_2/2HCl/0.5H_2O$)
Calculated (%) C, 53.63; H, 7.50; N, 18.24.
Found (%) C, 53.63; H, 7.56; N, 17.89.
Positive ion FAB-MS m/z: 456 [M+H]$^+$
Specific rotation $[\alpha]^{20}_D$=+64.07 (c=0.518 methanol)
Appearance: white powder

Example 235

4-[((1S,2R)-2-{[imino(isoxazolidin-2-yl)methyl]amino}cyclo hexyl)amino]-N-isobutyl-6-methylquinazolin-2-carboxamide dihydrochloride Elemental analysis value (as $C_{24}H_{35}N_7O_2/2HCl/1.2H_2O$)
Calculated (%) C, 52.59; H, 7.25; N, 17.89.
Found (%) C, 52.55; H, 7.13; N, 17.59.
Positive ion FAB-MS m/z: 454 [M+H]$^+$
Specific rotation $[\alpha]^{20}_D$=+59.96 (c=0.507 methanol)
Appearance: white powder

Example 236

4-{[(1S,2R)-2-({imino[methoxy(methyl)amino]methyl}amino)cyclohexyl]amino}-N-isobutyl-6-methylquinazolin-2-carboxamide dihydrochloride Elemental analysis value (as $C_{23}H_{35}N_7O_2/2HCl/0.7H_2O$)
Calculated (%) C, 52.41; H, 7.34; N, 18.60.
Found (%) C, 52.44; H, 7.22; N, 18.26.
Positive ion FAB-MS m/z: 442 [M+H]$^+$
Specific rotation $[\alpha]^{20}_D$=+73.00 (c=0.526 methanol)
Appearance: white powder

Example 237

4-{[(1S,2R)-2-({imino[methoxy(methyl)amino]methyl}amino)cyclohexyl]amino}-N-(trans-4-methoxycyclohexyl)-6-methylquinazolin-2-carboxamide dihydrochloride Elemental analysis value (as $C_{26}H_{39}N_7O_3/2HCl/H_2O$)
Calculated (%) C, 53.06; H, 7.36; N, 16.66.
Found (%) C, 53.34; H, 7.17; N, 16.40.
Positive ion FAB-MS m/z: 498 [M+H]$^+$
Specific rotation $[\alpha]^{20}_D$=+70.16 (c=0.496 methanol)
Appearance: white powder

Example 238

4-{[(1S,2R)-2-({imino[methoxy(methyl)amino]methyl}amino)cyclohexyl]amino}-N-(3-methoxypropyl)-6-methylquinazolin-2-carboxamide dihydrochloride Elemental analysis value (as $C_{23}H_{35}N_7O_3/2HCl/2H_2O$)
Calculated (%) C, 48.76; H, 7.29; N, 17.31.
Found (%) C, 48.38; H, 6.89; N, 17.14.
Positive ion FAB-MS m/z: 458 [M+H]$^+$
Specific rotation $[\alpha]^{20}_D$=+66.80 (c=0.500 methanol)
Appearance: white powder

Example 239

4-[((1S,2R)-2-{[amino(methoxyimino)methyl]amino}cyclohexyl)amino]-N-(3-methoxypropyl)-6-methylquinazolin-2-carboxamide dihydrochloride Elemental analysis value (as $C_{22}H_{33}N_7O_3/2HCl/2.2H_2O$)
Calculated (%) C, 47.36; H, 7.15; N, 17.57.
Found (%) C, 47.19; H, 6.76; N, 17.50.
Positive ion FAB-MS m/z: 444 [M+H]$^+$
Specific rotation $[\alpha]^{20}_D$=+47.45 (c=0.510 methanol)
Appearance: white powder

Example 240

4-[((1S,2R)-2-{[amino(hydroxyimino)methyl]amino}cyclohexyl)amino]-N-(3-methoxypropyl)-6-methylquinazolin-2-carboxamide dihydrochloride Positive ion FAB-MS m/z: 430 [M+H]$^+$
Specific rotation $[\alpha]^{20}_D$=+31.28 (c=0.505 methanol)
Appearance: white powder

Example 241

4-[((1S,2R)-2-{[amino(methoxyimino)methyl]amino}cyclohexyl)amino]-N-(2-ethoxyethyl)-6-methylquinazolin-2-carboxamide dihydrochloride Elemental analysis value (as $C_{23}H_{33}N_7O_3/2HCl/2H_2O$)
Calculated (%) C, 47.83; H, 7.11; N, 17.75.
Found (%) C, 47.59; H, 6.94; N, 17.72.
Positive ion FAB-MS m/z: 444 [M+H]$^+$
Specific rotation $[\alpha]^{20}_D$=+57.20 (c=0.500 methanol)
Appearance: white powder

Example 242

4-[((1R,2S)-2-{[amino(methoxyimino)methyl]amino}cyclohexyl)amino]-N-(2-methoxyethyl)-6-methylquinazolin-2-carboxamide dihydrochloride Positive ion FAB-MS m/z: 430 [M+H]$^+$
Specific rotation $[\alpha]^{20}_D$=−53.09 (c=0.550 methanol)
Appearance: white powder

Example 243

4-[((1S,2R)-2-{[amino(ethoxyimino)methyl]amino}cyclohexyl)amino]-N-(2-methoxyethyl)-6-methylquinazolin-2-carboxamide dihydrochloride Positive ion FAB-MS m/z: 444 [M+H]$^+$
Specific rotation $[\alpha]^{20}_D$=+55.04 (c=0.505 methanol)
Appearance: white powder

Example 244

4-[((1S,2R)-2-{[amino(propoxyimino)methyl]amino}cyclohexyl)amino]-N-(2-methoxyethyl)-6-methylquinazolin-2-carboxamide dihydrochloride Elemental analysis value (as $C_{23}H_{35}N_7O_3/2HCl/3.3H_2O$)
Calculated (%) C, 49.23; H, 7.26; N, 17.47.
Found (%) C, 48.97; H, 6.88; N, 17.48.
Positive ion FAB-MS m/z: 458 [M+H]$^+$
Specific rotation $[\alpha]^{20}_D$=+50.29 (c=0.505 methanol)
Appearance: white powder

Example 245

4-{[(1S,2R)-2-({amino[(2-methoxyethoxy)imino]methyl}amino)cyclohexyl]amino}-N-(2-methoxyethyl)-6-methylquinazolin-2-carboxamide dihydrochloride Elemental analysis value (as $C_{23}H_{35}N_7O_4/2HCl/2.4H_2O$)
Calculated (%) C, 46.84; H, 7.14; N, 16.63.
Found (%) C, 46.82; H, 6.82; N, 16.50.
Positive ion FAB-MS m/z: 474 [M+H]$^+$
Specific rotation $[\alpha]^{20}_D$=+48.40 (c=0.500 methanol)
Appearance: white powder

Example 246

4-{[(1S,2R)-2-({amino[(2-fluoroethoxy)imino]methyl}amino)cyclohexyl]amino}-N-(2-methoxyethyl)-6-methylquinazolin-2-carboxamide dihydrochloride Elemental analysis value (as $C_{22}H_{32}N_7O_3F/2HCl/2H_2O$)
Calculated (%) C, 46.32; H, 6.71; N, 17.19.
Found (%) C, 46.32; H, 6.36; N, 17.09.
Positive ion FAB-MS m/z: 462 [M+H]$^+$
Specific rotation $[\alpha]^{20}_D$=+47.76 (c=0.515 methanol)
Appearance: white powder

Example 247

4-({(1S,2R)-2-[(amino{[2-(methylthio)ethoxy]imino}methyl)amino]cyclohexyl}amino)-N-(2-methoxyethyl)-6-methylquinazolin-2-carboxamide dihydrochloride Elemental analysis value (as $C_{23}H_{35}N_7O_3S/2HCl/2H_2O$)
Calculated (%) C, 46.15; H, 6.90; N, 16.38.
Found (%) C, 46.05; H, 6.73; N, 16.26.
Positive ion FAB-MS m/z: 490 [M+H]$^+$
Specific rotation $[\alpha]^{20}_D$=+39.19 (c=0.500 methanol)
Appearance: white powder

Example 248

4-[((1S,2R)-2-{[amino(methoxyimino)methyl]amino}cyclohexyl)amino]-N-(2-methoxyethyl)-6-methylquinazolin-2-carboxamide 1/2 sulfate 300 mg of 4-[((1S,2R)-2-{[amino(methoxyimino)methyl]amino}cyclohexyl)amino]-N-(2-methoxyethyl)-6-methylquinazolin-2-carboxamide was suspended in 9 ml of methanol, and 35.4 mg of concentrated sulfuric acid was added thereto. After the mixture was stirred for 15 minutes, 75 ml of diisopropyl ether was added thereto. The deposited substance was collected by filtration, washed with diisopropyl ether and dried under reduced pressure, whereby 314 mg of a desired compound was obtained as a white powder.

Elemental analysis value (as $C_{21}H_{31}N_7O_3/0.5H_2SO_4/1.5H_2O$)
Calculated (%) C, 49.89; H, 6.98; N, 19.39.
Found (%) C, 49.78; H, 6.61; N, 19.18.
Positive ion FAB-MS m/z: 430 [M+H]$^+$
Specific rotation $[\alpha]^{20}_D$=−27.63 (c=0.550 methanol)

Example 249

4-[((1S,2R)-2-{[amino(methoxyimino)methyl]amino}cyclohexyl)amino]-6-methylquinazolin-2-carboxamide dihydrochloride Positive ion FAB-MS m/z: 372 [M+H]$^+$
Specific rotation $[\alpha]^{20}_D$=+57.20 (c=0.465 methanol)
Appearance: white powder

Example 250

4-[((1S,2R)-2-{[amino(methoxyimino)methyl]amino}cyclohexyl)amino]-N-methoxy-6-methylquinazolin-2-carboxamide dihydrochloride Elemental analysis value (as $C_{19}H_{27}N_7O_3/2HCl/0.8H_2O$)
Calculated (%) C, 46.69; H, 6.31; N, 20.06.
Found (%) C, 46.95; H, 6.27; N, 19.87.
Positive ion FAB-MS m/z: 402 [M+H]$^+$
Specific rotation $[\alpha]^{20}_D$=+8.80 (c=0.500 methanol)
Appearance: white powder

Test Example 1

Test for Skin Sensitization in Guinea Pigs (Adjuvant and Patch Test Method)

The dorsal area of male Hartley guinea pigs (n=5) at the age of 7 weeks was shaved with an electric shaver, and on the following day, primary sensitization was initiated. In the primary sensitization, emulsified complete Freund's adjuvant was intradermally administered at a dose of 0.1 ml only at the initial time, and an adhesive plaster for a patch test spread with 0.1 g of an ointment containing a test compound at 1%, was applied in an occluded state to the site where the adjuvant was intradermally administered. As a base of the ointment, petrolatum containing sorbitan sesquioleate (a surfactant) at 1% was used. At 24 hours after the adhesive plaster for a patch test was applied, the adhesive plaster was removed, and the application site was cleaned by wiping. The procedure of this primary sensitization was performed once daily and continued for a total of 3 days. On 7 days after the initial application of the primary sensitization, secondary sensitization was performed. The site subjected to the primary sensitization was shaved, and an ointment containing sodium lauryl sulfate at 10% was applied thereto in an open state. After 24 hours, the application site was cleaned by wiping, and a lint cloth spread with 0.2 g of the ointment containing a test compound at 1% was applied, thereto in an occluded state. At 48 hours after the lint cloth was applied, the cloth was removed, and the application site was cleaned by wiping. Challenge was performed on 13 days after initiation of the secondary sensitization. The dorsal area and flank area were shaved, and 0.01 g of the ointment containing a test compound at 1% was applied to the challenge site and left for about 24 hours. At about 24 hours and 48 hours after the challenge, observation of the skin surface was performed, and the presence or absence of sensitizing was determined. The determination was carried out by scoring according to the evaluation criteria (see Table 1) of the Draize method (1959).

In this connection, as a positive control, 1-chloro-2,4-dinitrobenzene (DNCB) (sensitization: 1%, challenge: 0.1%) was used. As the test compound, the compounds of Example 58 and Example 248 were used. As a comparative control, 4-[((1S,2R)-2-{[amino(imino)methyl]amino}cyclohexyl)amino]-N-isobutyl-6-methylquinazoline-2-carboxamide dihydrochloride described in Example 383 in Patent document 1 (sensitization: 0.1%, induction: 1%) was used.

TABLE 1

| | Erythema |
|---|---|
| 0 | No erythema |
| 1 | Very slight erythema (barely perceptible) |
| 2 | Well-defined erythema |
| 3 | Moderate to severe erythema |
| 4 | Severe erythema to slight eschar formation (injuries in depth) |

| | Edema |
|---|---|
| 0 | No edema |
| 1 | Very slight edema (barely perceptible) |
| 2 | Slight edema (edges of area well defined by definite raising) |
| 3 | Moderate edema (raised approximately 1 mm) |
| 4 | Severe edema (raised 1 mm or more and extending beyond the area of exposure) |

As a result, sensitizing was not observed in the test compounds. However, in the positive control of DNCB, severe erythema (score 3 in 3/5 cases, score 2 in 1/5 cases, and score 1 in 1/5 cases) and slight edema (score 1 in 3/5 cases, and score 0 in 2/5 cases) were observed. Further, in the comparative control compound, edema was not observed in all the cases, while well-defined erythema (score 2) was observed in 2/5 cases.

Accordingly, it is evident that the inventive compounds which do not show sensitizing are very useful not only for external preparations but also for medicaments of other dosage forms.

Test Example 2

Test for Primary Skin Irritation in Rabbits

The dorsal area of female Kbs: JW rabbits (n=3 to 32) at the age of 20 weeks was shaved with an electric shaver, and on the following day, an adhesive plaster for a patch test spread with 0.1 g of an ointment containing a test compound was applied (administered) to the dorsal skin. As a base of the ointment, petrolatum containing sorbitan sesquioleate (a surfactant) at 5% was used. At 24 hours after administration, the adhesive plaster for a patch test was removed, and the application site was cleaned by wiping. Then, erythema and edema formation at the application site was observed. The determination of irritation was carried out by scoring according to the evaluation criteria (Table 1) of the Draize method (1959) used in Test example 1. The mean value of the sum of erythema and edema scores was used as a simple primary skin irritation index.

As comparative control compounds, the following compounds which are structurally similar to the inventive compound were used: 4-[((1S,2R)-2-{[amino(imino)methyl]amino}cyclohexyl)amino]-N-isobutyl-6-methylquinazoline-2-carboxamide dihydrochloride (hereinafter referred to as Comparative control A) described in Example 383 in WO 03/091224; 4-[((1S,2R)-2-{[amino(imino)methyl]amino}cyclohexyl)amino]-6-methyl-N-neopentyl quinazoline-2-carboxamide dihydrochloride (hereinafter referred to as Comparative control B) described in Example 29 in WO 03/091224; 4-[((1S,2R)-2-{[amino(imino)methyl]amino}cyclohexyl)amino]-N-(2-ethoxy ethyl)-6-methylquinazoline-2-carboxamide dihydrochloride (hereinafter referred to as Comparative control C) described in Example 372 in WO 03/091224; 4-[((1S,2R)-2-{[amino(imino)methyl]amino}cyclohexyl)amino]-N-(3-methoxypropyl)-6-methylquinazoline-2-carboxamide dihydrochloride (hereinafter referred to as Comparative control D) described in Example 346 in WO 03/091224; 4-[((1S,2R)-2-{[amino(imino)methyl]amino}cyclohexyl)amino]-N-isopropyl-6-methylquinazoline-2-carboxamide dihydrochloride (hereinafter referred to as Comparative control E) described in Example 388 in WO 03/091224; and 4-[((1S,2R)-2-{[amino(imino)methyl]amino}cyclohexyl)amino]-N-(2-methoxyethyl)-6-methylquinazoline-2-carboxamide dihydrochloride (hereinafter referred to as Comparative control F) described in Example 48 in WO 03/091224.

To be more specific, the compound of Comparative control A is different from the compounds of Examples 211, 212, 236 and 60 according to the present invention only in the substituent at the 4-position; the compound of Comparative control B is different from the compound of Example 19 according to the present invention only in the substituent at the 4-position; the compound of Comparative control C is different from the compounds of Examples 94, 95 and 61 according to the present invention only in the substituent at the 4-position; the compound of Comparative control D is different from the compounds of Examples 239, 240, 92, 59, 35 and 93 according to the present invention only in the substituent at the 4-position; the compound of Comparative control E is different from the compounds of Examples 101 and 58 according to the present invention only in the substituent at the 4-position; the compound of Comparative control F is different from the compounds of Examples 208, 1 and 91 according to the present invention only in the substituent at the 4-position; and all other moieties have the same structures. The results are shown in Table 2.

TABLE 2

| Test compound or comparative control compound | Concentration (%) | Simple primary skin irritation index |
|---|---|---|
| Comparative control A | 3.0 | 1.8 |
| Example 211 | 3.0 | 1.5 |
| Example 212 | 3.0 | 0.8 |
| Example 236 | 3.0 | 1.6 |
| Example 60 | 3.0 | 1.0 |
| Comparative control B | 3.0 | 2.4 |
| Example 19 | 3.0 | 0.4 |
| Comparative control C | 3.0 | 2.3 |
| Example 94 | 3.0 | 1.0 |
| Example 95 | 3.0 | 0.7 |
| Example 61 | 3.0 | 0.4 |
| Comparative control D | 3.0 | 2.0 |
| Example 239 | 3.0 | 1.0 |
| Example 240 | 3.0 | 1.0 |
| Example 92 | 3.0 | 0.0 |
| Example 59 | 3.0 | 0.2 |
| Example 35 | 3.0 | 1.5 |
| Example 93 | 3.0 | 0.2 |
| Comparative control E | 3.0 | 3.6 |
| Example 101 | 3.0 | 2.6 |
| Example 58 | 3.0 | 0.4 |
| Comparative control F | 3.0 | 2.2 |
| Example 208 | 3.0 | 0.2 |

TABLE 2-continued

| Test compound or comparative control compound | Concentration (%) | Simple primary skin irritation index |
|---|---|---|
| Example 248 | 3.0 | 0.8 |
| Example 1 | 3.0 | 0.3 |
| Example 91 | 3.0 | 0.5 |

As shown in Table 2, substitution of the guanidino group in the side chain at the 4-position of a quinazoline derivative with such substituents as those in the inventive compounds markedly reduced the primary skin irritation. Accordingly, it is evident that the inventive compounds are extremely useful as an external preparation with less skin irritation.

Test Example 3

Effect on Scratching Behavior Induced by Serotonin Application in Mice

To the cervical and dorsal area of male ICR mice (n=3 to 6) at the age of 4 to 6 weeks, 100 µl of a solution obtained by dissolving serotonin hydrochloride in ethanol at 0.1% (hereinafter referred to as serotonin) was applied, and the number of scratching behavior at the application site with the hind legs occurring immediately after the application was counted for 15 minutes after administration with a counter. Administration of a test compound was carried out by skin application, intravenous administration or oral administration. In the case of skin application, the test compound that was dissolved in ethanol was applied in an amount of 100 µl concurrently with serotonin. In the case of intravenous administration, the test compound that was dissolved in physiological saline was administered at a dose of 10 ml/kg at 5 minutes prior to the serotonin application. In the case of oral administration, the test compound that was dissolved in distilled water was administered at a dose of 10 ml/kg at 20 minutes prior to the serotonin application. The control group of each administration route was given the respective solvent, and the values of scratching behavior were compared between the control group and the test compound group.

The results obtained by skin application of the test compound are shown in Table 3; the results obtained by intravenous administration of the test compound are shown in Table 4; and the results obtained by oral administration of the test compound are shown in Table 5.

TABLE 3

| Test compound | Concentration (%) | Average number of scratching behavior | Standard error | Average number of scratching behavior in control group |
|---|---|---|---|---|
| Example 211 | 0.1 | 73.0 | 9.7 | 134.8 |
| Example 212 | 0.1 | 49.8 | 7.8 | 180.3 |
| Example 19 | 0.1 | 69.2 | 9.8 | 164.6 |
| Example 239 | 0.1 | 55.8 | 13.9 | 134.8 |
| Example 240 | 0.1 | 65.3 | 7.1 | 111.3 |
| Example 92 | 0.1 | 76.3 | 11.7 | 138.3 |
| Example 59 | 0.1 | 57.8 | 9.3 | 131.0 |
| Example 35 | 0.1 | 69.0 | 5.3 | 168.8 |
| Example 101 | 0.1 | 56.8 | 7.5 | 137.0 |
| Example 58 | 0.1 | 55.5 | 6.8 | 131.0 |
| Example 208 | 0.1 | 81.0 | 15.2 | 211.2 |
| Example 1 | 0.1 | 57.8 | 6.6 | 101.8 |
| Example 91 | 0.1 | 70.5 | 11.6 | 166.5 |

TABLE 4

| Test compound | Dose mg/kg | Average number of scratching behavior | Standard error | Average number of scratching behavior in control group |
|---|---|---|---|---|
| Example 60 | 3 | 64.0 | 8.5 | 156.3 |
| Example 208 | 3 | 53.8 | 14.3 | 158.8 |

TABLE 5

| Test compound | Dose mg/kg | Average number of scratching behavior | Standard error | Average number of scratching behavior in control group |
|---|---|---|---|---|
| Example 239 | 30 | 88.6 | 9.6 | 148.8 |
| Example 240 | 30 | 95.2 | 6.2 | 229.2 |
| Example 92 | 30 | 141.0 | 12.4 | 229.2 |

As shown in Tables 3 to 5, the inventive compounds significantly suppressed scratching behavior at the cervical and dorsal area induced by serotonin application. From these results, it is evident that the use of inventive compounds as an external preparation, a preparation for intravenous administration or a preparation for oral administration are useful for itching caused by various pruritic diseases.

Test Example 4

Effect on Spontaneous Scratching Behavior Induced by Disruption of the Horny Layer Barrier in Mice The cervical and dorsal area of male ICR mice at the age of 5 weeks was shaved under ether anesthesia, and the horny layer barrier was disrupted by applying a solution mixture of acetone and ether in a ratio of 1:1 to the shaved site and then applying distilled water twice a day for consecutive days (for 10 days). Spontaneous scratching behavior at the vicinity of the shaved site induced by disruption of the horny layer barrier was observed before and after the application of a test drug each for 30 minutes using a video system under an unmanned condition and a change (%) in the number of scratching behavior was measured. As the test drug, an ointment containing a test compound was used, and 50 mg in terms of the ointment was applied to the area around the shaved site. In this connection, in a control group, a petrolatum ointment containing sorbitan sesquioleate (a surfactant) used as a base of the ointment in an amount of 1% was used. The results are shown in Table 6.

TABLE 6

| Test compound | Concentration (%) | Ratio of change (%) | Standard error |
|---|---|---|---|
| Control group | — | 100.9 | 16.9 |
| Example 60 | 0.1 | 55.2 | 5.7 |
| Example 94 | 0.1 | 43.9 | 10.2 |
| Example 61 | 0.1 | 51.7 | 14.8 |
| Example 239 | 0.1 | 47.9 | 11.3 |
| Example 240 | 0.1 | 54.5 | 11.7 |
| Example 92 | 1.0 | 55.9 | 12.4 |
| Example 35 | 0.1 | 60.4 | 8.0 |
| Example 58 | 0.1 | 67.7 | 15.5 |
| Example 208 | 0.1 | 41.6 | 10.7 |

As shown in Table 6, the inventive compounds significantly suppressed spontaneous scratching behavior induced by disruption of the horny layer barrier. From these results, it is evident that the use of inventive compounds as an ointment external preparation is also effective in the treatment of itching caused by xeroderma or atopic dermatitis, itching accompanying dialysis and other itching.

Test Example 5

Acute Toxicity Test in Mice

Male ICR mice at the age of 4 to 6 weeks were used. The inventive compound was intravenously administered at a dose of 10 ml/kg from the tail vein, and then, the behavior thereof was observed for 2 hours. The results are shown in Table 7.

TABLE 7

| Test compound | Concentration (mg/kg) | Change in behavior |
|---|---|---|
| Example 211 | 10 | No obvious change |
| Example 212 | 10 | No obvious change |
| Example 60 | 5 | No obvious change |
| Example 239 | 10 | No obvious change |
| Example 240 | 10 | No obvious change |
| Example 92 | 10 | No obvious change |
| Example 101 | 10 | No obvious change |
| Example 58 | 10 | No obvious change |
| Example 208 | 20 | No obvious change |
| Example 1 | 10 | No obvious change |

As shown in Table 7, changes in symptoms such as sedation were not observed at all in mice to which the test compound was administered. Accordingly, the toxicity of the inventive compound is extremely low, and the compound can be used safely as a pharmaceutical.

Preparation Example 1

100 g of the inventive compound of Example 1, 292 g of D-mannitol, 120 g of corn starch and 28 g of low-substituted hydroxypropyl cellulose are placed in a fluidized bed granulation dryer (STREA; manufactured by PAUREC) and granulated with spraying a certain amount of an aqueous 5% hydroxypropyl cellulose solution. After drying and then milling with a grinding/milling machine (COMIL; manufactured by PAULEC), a certain amount of magnesium stearate is mixed therewith in a mixer (BOHRE container mixer Model MC20; manufactured by KOTOBUKI-GIKEN), and the mixture is molded into tablets with a diameter of 7 mm and a weight of 140 mg per tablet with a rotary tablet compacting machine (CORRECT 12HUK; manufactured by KIKUSUI), whereby a tablet containing 25 mg of the inventive compound is obtained.

Preparation Example 2

75 g of the inventive compound of Example 1, 180 g of lactose, 75 g of corn starch and 18 g of carmellose calcium are placed in a stirring granulator (vertical granulator model VG-01), and a certain amount of an aqueous 5% hydroxypropylmethyl cellulose solution is added thereto and the mixture is granulated and dried by a fluidized bed granulation dryer (STREA; manufactured by PAUREC) and then milled by a grinding/milling machine (COMIL; manufactured by PAULEC). 120 mg of the milled material is filled into a No. 3 capsule using a capsule filling machine (capsule filler; SHIONOGI QUALICAPS), whereby a capsule containing 25 mg of the inventive compound is obtained.

Preparation Example 3

2.5 g of the inventive compound of Example 1 and 4.5 g of sodium chloride are weighed, and 450 ml of water for injection is added thereto and the mixture is stirred and dissolved, and then adjusted to pH 6.5 with 0.1 mol/l hydrochloric acid or 0.1 mol/l sodium hydroxide. Then water for injection is added to make the total volume 500 ml. The solution thus prepared is filtered under pressure through a membrane filter (pore size: 0.22 μm). Then 5.3 ml of the filtrate is aseptically filled into a sterilized 5 ml brown ampoule, whereby an injection formulation containing 25 mg of the inventive compound is obtained. The procedure from the preparation through the filling is performed in an aseptic manner.

Preparation Example 4

99.75 g of WITEPSOL H-15 (manufactured by HIRTH) is dissolved at 45° C. and 0.25 g of the inventive compound of Example 1 is added thereto and dispersed therein by stirring. The resulting dispersion is infused into a 1 g suppository mold while paying attention to preventing deposition at a high temperature, solidified and taken out from the mold, whereby a suppository containing 25 mg of the inventive compound is obtained.

Preparation Example 5

0.5 g of the inventive compound of Example 1, 5.2 g of sodium dihydrogen phosphate, 11.9 g of sodium monohydrogen phosphate, 2.5 g of sodium chloride and 0.3 g of benzalkonium chloride are weighed, and 950 ml of purified water is added thereto, and the mixture is stirred and dissolved. Then purified water is added to make the total volume 1000 ml. The solution thus prepared is filtered under pressure through a membrane filter (pore size: 0.2 μm). Then, 5 ml of the filtrate is filled aseptically to a sterilized 5 ml eye drop bottle, whereby an eye drop (5 ml) containing 0.5 mg/ml of the inventive compound is obtained. The procedure from the preparation through the filling is performed in an aseptic manner.

Preparation Example 6

80 g of olive oil, 15 g of cetyl alcohol and 15 g of stearyl alcohol are weighed, and the mixture is stirred and dissolved while heating to 70° C. on a water bath (oil phase). Separately, 1 g of the inventive compound of Example 1, 10 g of Polysolvate 80, 5 g of sodium lauryl sulfate, 0.25 g of methyl parahydroxybenzoate, 0.15 g of propyl parahydroxybenzoate and 880 g of purified water are weighed, and the mixture is stirred and dissolved while heating to 70° C. on a water bath (aqueous phase). The oil phase and the aqueous phase are placed in a vacuum emulsifying apparatus and then the mixture is emulsified while stirring at a high speed in a homomixer at 70° C. under vacuum. Then, the resulting emulsion is water-cooled to 35° C. while stirring at a low speed. Then 50 ml of the resulting emulsion is filled into a 50 ml container for lotion, whereby a lotion (50 ml) containing 1.0 mg/ml of the inventive compound is obtained.

Preparation Example 7

250 g of white petrolatum, 250 g of stearyl alcohol and 40 g of polyoxyethylene hydrogenated castor oil 60 are weighed, and the mixture is stirred and dissolved while heating to 70° C. on a water bath (oil phase). Separately, 1 g of the inventive compound of Example 1, 120 g of propylene glycol, 0.25 g of methyl parahydroxybenzoate, 0.15 g of propyl parahydroxybenzoate and 340 g of purified water are weighed, and the mixture is stirred and dissolved while heating to 70° C. on a water bath (aqueous phase). The oil phase and the aqueous phase are placed in a vacuum stirring and mixing apparatus and then the mixture is emulsified while stirring at 70° C. under vacuum. An ointment obtained by cooling the resulting emulsion and slowly stirring until the emulsion is solidified is filled into a 10 g ointment bottle or a 10 g ointment tube, whereby an ointment containing 1.0 mg/g of the inventive compound is obtained.

Preparation Example 8

110 g of gelatin, 25 g of polyvinyl alcohol and 10 g of methylcellulose are weighed and mixed to obtain a mixed powder. Then, 13 g of glycerin is added thereto, and the powder is dispersed therein using a small-sized mixer. Then, 100 g of purified water is added thereto, and the mixture is dissolved therein while heating to 60° C. Further, 85 g of kaolin is added thereto and dispersed therein at 60° C. A dispersion separately obtained by mixing 20 g of glycerin with 5 g of sodium polyacrylate is added thereto, and dissolved and dispersed therein at 60° C. Then 15 g of polybutene is added thereto and dispersed therein at 60° C. To the dispersion, 0.5 g of the inventive compound of Example 1 is added and dispersed therein at 50° C. thereby obtaining a paste. Then, the paste is spread over a support (nonwoven fabric) (100 g/700 cm$^2$), and then the coated support is covered with a liner made of a polyethylene film (50 μm) and cut, whereby an adhesive preparation is obtained. The inventive compound is contained in an amount of 1 mg in 7 cm$^2$ of the adhesive preparation.

INDUSTRIAL APPLICABILITY

As described above, the inventive compound has an action of strongly suppressing scratching behavior, less skin irritation and no skin sensitization, and hence, it is extremely useful as an external preparation. Further, the inventive compound has an action of suppressing scratching behavior not only by application to the skin, but also by intravenous administration, subcutaneous administration and oral administration, and therefore, it is extremely useful as a medicament in other dosage forms.

The invention claimed is:

1. A quinazoline derivative represented by the following general formula [1] or a pharmaceutically acceptable salt thereof:

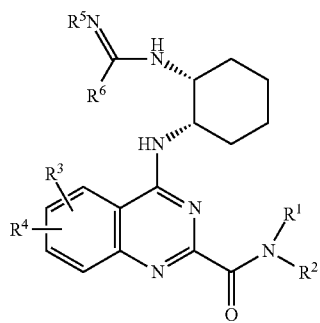

wherein $R^1$ represents hydrogen or alkyl;
$R^2$ represents hydrogen, alkoxy, tetrahydropyranyl, phenyl, cycloalkyl, (cycloalkyl)alkyl or alkyl, wherein the alkoxy, tetrahydropyranyl, phenyl, cycloalkyl, (cycloalkyl)alkyl, and alkyl groups are optionally substituted with one to three groups selected from the group consisting of alkoxy, halogen, alkoxyalkyl, hydroxy, alkylthio, a 5- to 10-membered aromatic heterocyclic group containing one to three heteroatoms selected from a nitrogen atom, an oxygen atom, and a sulfur atom, a 5- to 7-membered saturated aliphatic heterocyclic group optionally substituted with acyl and contains one to three nitrogen atoms, and phenyl optionally substituted with halogen or alkoxy;
$R^3$ and $R^4$ are the same or different and each represents hydrogen, alkyl, alkoxy, or halogen; and
$R^5$ and $R^6$ represent any one of the following groups:
(i) $R^5$ is combined with $R^6$ to represent alkylene, wherein the alkylene group is optionally substituted with hydroxy or oxo, and the alkylyene is optionally condensed with a benzene ring;
(ii) $R^5$ is selected from the group consisting of hydrogen, hydroxy, alkyl, phenyl, an alkoxy, wherein the alkyl, phenyl and alkoxy is optionally substituted with one to three groups selected from the group consisting of alkoxy, alkylthio and halogen; and
$R^6$ is selected from the group consisting of alkyl, cycloalkyl, phenyl, and a 5- to 10-membered aromatic heterocyclic group containing one to three heteroatoms selected from the group consisting of a nitrogen atom, an oxygen atom and a sulfur atom, wherein the alkyl, cycloalkyl, phenyl, and aromatic heterocyclic group is optionally substituted with one to three groups selected from the group consisting of alkoxy, hydroxy, phenyl, pyridyl, furyl, halogen, and N,N-dialkylamino.

2. The quinazoline derivative or pharmaceutically acceptable salt thereof according to claim 1, wherein
$R^5$ is selected from the group consisting of hydrogen, alkyl, phenyl, and alkoxy; and
$R^6$ is selected from the group consisting of alkyl, cycloalkyl, phenyl, and a 5- to 10-membered aromatic heterocyclic group containing one to three heteroatoms selected from the group consisting of a nitrogen atom, an oxygen atom and a sulfur atom, wherein the alkyl, cycloalkyl, phenyl, and aromatic heterocyclic groups are optionally substituted with one to three groups selected from the group consisting of alkoxy, hydroxy, phenyl, pyridyl, furyl, halogen and N,N-dialkylamino; or
$R^5$ is combined with $R^6$ to represent alkylene, wherein the alkylene group is optionally substituted with hydroxy or oxo, and is optionally condensed with a benzene ring.

3. The quinazoline derivative or pharmaceutically acceptable salt thereof according to claim 2, wherein
$R^2$ represents hydrogen, alkoxy, tetrahydropyranyl, phenyl, cycloalkyl, (cycloalkyl)alkyl, or alkyl, wherein the phenyl is optionally substituted with an alkoxy, wherein the cycloalkyl is optionally substituted with one to three groups selected from the group consisting of halogen, alkoxy, alkoxyalkyl and hydroxy, and wherein the (cycloalkyl) alkyl is optionally substituted with one to three groups selected from the group consisting of alkoxyalkyl, and hydroxy;
$R^5$ is selected from the group consisting of hydrogen, alkyl, phenyl and alkoxy; and
$R^6$ represents alkyl, cycloalkyl, phenyl, or a 5- to 10-membered aromatic heterocyclic group containing one to three heteroatoms selected from the group consisting of a nitrogen atom, an oxygen atom and a sulfur atom, and wherein the alkyl is optionally substituted with one to three groups selected from alkoxy, hydroxy, N,N-dialkylamino, phenyl, pyridyl and furyl and wherein the phenyl is optionally substituted with one to three groups selected from alkoxy, halogen and N,N-dialkylamino; or $R^5$ is combined with $R^6$ to represent alkylene, wherein the alkylene group is optionally substituted with hydroxy or oxo, and is optionally condensed with a benzene ring.

4. The quinazoline derivative or pharmaceutically acceptable salt thereof according to claim 1, which is selected from the group consisting of:

- 4-{([1S,2R)-2-(ethanimidoylamino)cyclohexyl]amino}-N-(2-methoxyethyl)-6-methylquinazolin-2-carboxamide,
- N-(2,2-dimethylpropyl)-4-([{(1S,2R)-2-[(2-methoxy-2-methylpropanimidoyl)amino]cyclohexyl}amino]-6-methylquinazolin-2-carboxamide,
- 4-({(1S,2R)-2-[(3-methoxypropanimidoyl)amino]cyclohexyl}amino)-N-(3-methoxypropyl)-6-methylquinazolin-2-carboxamide,
- 4-({(1S,2R)-2-[(3-hydroxypropanimidoyl)amino]cyclohexyl}amino)-N-isopropyl-6-methylquinazolin-2-carboxamide,
- 4-({(1S,2R)-2-[(3-hydroxypropanimidoyl)amino]cyclohexyl}amino)-N-(3-methoxypropyl)-6-methylquinazolin-2-carboxamide,
- 4-({(1S,2R)-2-[(2-hydroxy-2-methylpropanimidoyl)amino]cyclohexyl}amino)-N-isobutyl-6-methylquinazolin-2-carboxamide,
- N-(2-ethoxyethyl)-4-({(1S,2R)-2-[(3-hydroxy propanimidoyl)amino]cyclohexyl}amino)-6-methylquinazolin-2-carboxamide,
- 4-({(1S,2R)-2-[(2-hydroxy-2-methylpropanimidoyl)amino]cyclohexyl}amino)-N-isopropyl-6-methylquinazolin-2-carboxamide,
- 4-({(1S,2R)-2-[(2-hydroxy-2-methylpropanimidoyl)amino]cyclohexyl}amino)-N-(2-methoxyethyl)-6-methylquinazolin-2-carboxamide,
- 4-({(1S,2R)-2-[(2-methoxyethanimidoyl)amino]cyclohexyl}amino)-N-(2-methoxyethyl)-6-methylquinazolin-2-carboxamide,
- 4-{[(1S,2R)-2-(ethanimidoylamino)cyclohexyl]amino}-N-(3-methoxypropyl)-6-methylquinazolin-2-carboxamide,
- 4-({(1S,2R)-2-[(2-methoxyethanimidoyl)amino]cyclohexyl}amino)-N-(3-methoxypropyl)-6-methylquinazolin-2-carboxamide,
- 4-{[(1S,2R)-2-(ethanimidoylamino)cyclohexyl]amino}-N-(2-ethoxyethyl)-6-methylquinazolin-2-carboxamide,
- N-(2-ethoxyethyl)-4-({(1S,2R)-2-[(2-methoxy ethanimidoyl)amino]cyclohexyl}amino)-6-methylquinazolin-2-carboxamide, and
- 4-{[(1S,2R)-2-(ethanimidoylamino)cyclohexyl]amino}-N-isopropyl-6-methylquinazolin-2-carboxamide.

5. A pharmaceutical composition comprising a quinazoline derivative or a pharmaceutically acceptable salt thereof according to claim 1 as an active ingredient and optionally one or more pharmaceutically acceptable carriers.

6. A method for suppressing itching comprising administering to a subject in need thereof an effective amount of a pharmaceutical composition according to claim 5.

* * * * *